US012291557B2

(12) United States Patent
Corey

(10) Patent No.: US 12,291,557 B2
(45) Date of Patent: May 6, 2025

(54) CHIMERIC TIM4 RECEPTORS AND USES THEREOF

(71) Applicant: CERO THERAPEUTICS HOLDINGS, INC., South San Francisco, CA (US)

(72) Inventor: Daniel Mark Corey, Menlo Park, CA (US)

(73) Assignee: CERO THERAPEUTICS HOLDINGS, INC., South San Francisco, CA (US)

( * ) Notice: Subject to any disclaimer, the term of this patent is extended or adjusted under 35 U.S.C. 154(b) by 1079 days.

(21) Appl. No.: 17/040,317

(22) PCT Filed: Mar. 27, 2019

(86) PCT No.: PCT/US2019/024435
§ 371 (c)(1),
(2) Date: Sep. 22, 2020

(87) PCT Pub. No.: WO2019/191334
PCT Pub. Date: Oct. 3, 2019

(65) Prior Publication Data
US 2021/0087251 A1    Mar. 25, 2021

Related U.S. Application Data

(60) Provisional application No. 62/649,491, filed on Mar. 28, 2018.

(51) Int. Cl.
| C07K 14/705 | (2006.01) |
| A61K 40/11 | (2025.01) |
| A61K 40/31 | (2025.01) |
| A61K 40/32 | (2025.01) |
| A61K 40/42 | (2025.01) |
| A61K 45/06 | (2006.01) |
| C07K 16/28 | (2006.01) |
| C12N 5/0783 | (2010.01) |

(52) U.S. Cl.
CPC ............ *C07K 14/705* (2013.01); *A61K 40/11* (2025.01); *A61K 40/31* (2025.01); *A61K 40/32* (2025.01); *A61K 40/4257* (2025.01); *A61K 45/06* (2013.01); *C07K 16/2818* (2013.01); *C12N 5/0636* (2013.01); *C07K 2319/02* (2013.01); *C07K 2319/03* (2013.01)

(58) Field of Classification Search
None
See application file for complete search history.

(56) References Cited

U.S. PATENT DOCUMENTS

| 5,019,368 A | 5/1991 | Epstein et al. |
| 5,641,863 A | 6/1997 | Schreiber et al. |
| 5,641,875 A | 6/1997 | Schreiber et al. |
| 5,776,910 A | 7/1998 | Schreiber et al. |
| 5,821,071 A | 10/1998 | Schreiber et al. |
| 6,068,983 A | 5/2000 | Schreiber et al. |
| 6,475,997 B1 | 11/2002 | Schreiber et al. |
| 6,630,313 B2 | 10/2003 | Fadok et al. |
| 8,119,772 B2 | 2/2012 | Yang et al. |
| 8,496,938 B2 | 7/2013 | Smith et al. |
| 8,956,616 B2 | 2/2015 | Thorpe et al. |
| 10,093,717 B2 | 10/2018 | Li et al. |
| 10,125,193 B2* | 11/2018 | Cooper ............. A61K 39/4611 |
| 10,793,641 B2* | 10/2020 | Wang ............... C07K 14/70517 |
| 10,980,836 B1 | 4/2021 | Getts et al. |
| 11,655,282 B2 | 5/2023 | Corey |
| 11,708,423 B2 | 7/2023 | Corey |
| 2003/0072743 A1 | 4/2003 | Albert et al. |
| 2003/0095962 A1 | 5/2003 | Ueda et al. |
| 2003/0124114 A1 | 7/2003 | McIntire et al. |
| 2003/0130218 A1 | 7/2003 | Schreiber et al. |
| 2006/0002940 A1 | 1/2006 | Stevenson |
| 2006/0257359 A1 | 11/2006 | Francois et al. |
| 2007/0258897 A1 | 11/2007 | Devitt et al. |
| 2008/0213216 A1 | 9/2008 | Schreiber et al. |
| 2011/0165649 A1 | 7/2011 | Tyler et al. |
| 2013/0071414 A1 | 3/2013 | Dotti et al. |
| 2014/0162290 A1 | 6/2014 | Watanabe et al. |
| 2015/0023986 A1 | 1/2015 | Jones et al. |
| 2017/0058024 A1 | 3/2017 | West et al. |
| 2017/0151281 A1 | 6/2017 | Wagner et al. |
| 2017/0166622 A1 | 6/2017 | Baeuerle et al. |
| 2017/0166657 A1 | 6/2017 | O'Neill et al. |
| 2017/0209492 A1 | 7/2017 | June et al. |
| 2018/0186855 A1 | 7/2018 | Rosenthal |

(Continued)

FOREIGN PATENT DOCUMENTS

| WO | WO 0168709 A1 | 9/2001 |
| WO | WO 0185207 A2 | 11/2001 |

(Continued)

OTHER PUBLICATIONS

Chen, Thomas T., et al. "TIM-2 is expressed on B cells and in liver and kidney and is a receptor for H-ferritin endocytosis." The Journal of experimental medicine 202.7 (2005): 955-965. (Year: 2005).*
Park, Daeho, Amelia Hochreiter-Hufford, and Kodi S. Ravichandran. "The phosphatidylserine receptor TIM-4 does not mediate direct signaling." Current biology 19.4 (2009): 346-351. (Year: 2009).*
Genbank Accession No. NP_612388 (2006) (Year: 2006).*
Genbank Accession No. NP_848874 (2009) (Year: 2009).*
Aderem, "Phagocytosis and the Inflammatory Response," JID 187(Suppl 2):S340-S345, 2003.

(Continued)

*Primary Examiner* — Robert J Yamasaki
(74) *Attorney, Agent, or Firm* — Fox Rothschild LLP

(57) ABSTRACT

The present disclosure relates to chimeric Tim4 receptors, host cells modified to include chimeric Tim4 receptor molecules, and methods of making and using such receptor molecules and modified cells.

11 Claims, No Drawings

Specification includes a Sequence Listing.

(56) References Cited

U.S. PATENT DOCUMENTS

| | | |
|---|---|---|
| 2018/0186878 A1 | 7/2018 | Rosenthal |
| 2018/0244748 A1 | 8/2018 | Gill et al. |
| 2018/0291089 A1 | 10/2018 | Epstein et al. |
| 2018/0319862 A1 | 11/2018 | Thompson et al. |
| 2018/0334653 A1 | 11/2018 | O'Neill |
| 2020/0002402 A1 | 1/2020 | Emtage et al. |
| 2020/0239592 A1 | 7/2020 | Vale et al. |
| 2020/0308305 A1 | 10/2020 | Corey |
| 2021/0015865 A1 | 1/2021 | Corey |
| 2021/0023135 A1 | 1/2021 | Corey |
| 2021/0024607 A1 | 1/2021 | Corey et al. |
| 2021/0253696 A1 | 8/2021 | Corey et al. |
| 2022/0098273 A1 | 3/2022 | Corey |

FOREIGN PATENT DOCUMENTS

| | | |
|---|---|---|
| WO | WO 2005019429 A2 | 3/2005 |
| WO | WO 2005090573 A2 | 9/2005 |
| WO | WO 2005097211 A2 | 10/2005 |
| WO | WO 2013074916 A1 | 5/2013 |
| WO | WO 2013192294 A1 | 12/2013 |
| WO | WO 2014031687 A1 | 2/2014 |
| WO | WO 2014059173 A2 | 4/2014 |
| WO | WO 2014153114 A1 | 9/2014 |
| WO | WO 2015066262 A1 | 5/2015 |
| WO | WO 2015123642 A1 | 8/2015 |
| WO | WO 2015184228 A1 | 12/2015 |
| WO | WO 2016019300 A1 | 2/2016 |
| WO | WO 2016044605 A1 | 3/2016 |
| WO | WO 2016126608 A1 | 8/2016 |
| WO | WO 2017019848 A1 | 2/2017 |
| WO | WO 2017025944 A2 | 2/2017 |
| WO | WO 2017083700 A1 | 5/2017 |
| WO | WO 2017205747 A1 | 11/2017 |
| WO | WO 2017219916 A1 | 12/2017 |
| WO | WO 2018031419 A1 | 2/2018 |
| WO | WO 2018064076 A1 | 4/2018 |
| WO | WO 2018132695 A1 | 7/2018 |
| WO | WO 2018212770 A1 | 11/2018 |
| WO | WO 2018220224 A1 | 12/2018 |
| WO | WO 2019067328 A1 | 4/2019 |
| WO | WO 2019079529 A1 | 4/2019 |
| WO | WO 2019086512 A1 | 5/2019 |
| WO | WO 2019091478 A1 | 5/2019 |
| WO | WO 2019157440 A1 | 8/2019 |
| WO | WO 2019191332 A1 | 10/2019 |
| WO | WO 2019191339 A1 | 10/2019 |
| WO | WO 2019191340 A1 | 10/2019 |
| WO | WO 2020223550 A1 | 11/2020 |
| WO | WO 2021067875 A1 | 4/2021 |
| WO | WO 2022036265 A1 | 2/2022 |
| WO | WO 2022036285 A1 | 2/2022 |
| WO | WO 2022036287 A1 | 2/2022 |
| WO | WO 2023010097 A1 | 2/2023 |

OTHER PUBLICATIONS

Agaugue et al., "224. Development of Safer & Optimized CAR-T Cells Using Lentiviral Vectors," Mol. Ther. 23(Suppl. 1):S88, May 2015.

Aggen et al., "Single-chain V(alpha)V(beta) T-cell receptors function without mispairing with endogenous TCR chains," Gene Therapy 19:365-374, 2012.

Albert et al., "αvβ5 integrin recruits the CrkII-Dock180-Rac1 complex for phagocytosis of apoptotic cells," Nature Cell Biology 2:899-905, Dec. 2000.

Altman et al., "Phenotypic Analysis of Antigen-Specific T Lymphocytes," Science 274:94-96, 1996.

Arandjelovic et al., "Phagocytosis of apoptotic cells in homeostasis," Nat. Immunol. 16(9):907-917, Sep. 2015.

Belzile et al., "Antibody targeting of phosphatidylserine for the detection and immunotherapy of cancer," Immuno Targets and Therapy, (7) pp. 1-14, 2018.

Blackburn et al., "Coregulation of CD8+ T cell exhaustion by multiple inhibitory receptors during chronic viral infection," Nature Immunology 10(1):29-37, Jan. 2009.

Blasius et al., "Intracellular Toll-like Receptors," Immunity 32:305-315, Mar. 26, 2010. (11 pages).

Burns et al., "A high molecular weight-melanoma associated antigen-specific chimeric antigen receptor redirects lymphocytes to target human melanomas," Cancer Res. 70(8):3027-3033, Apr. 15, 2010.

Castellano et al., "Membrane recruitment of Rac1 triggers phagocytosis," Journal of Cell Science 113:2955-2961, 2000.

Chen et al., "Fusion Protein Linkers: Property, Design and Functionality," Adv. Drug Deliv. Rev. 65(10):1357-1369, Oct. 15, 2013.

Chen et al., "TIM-2 is expressed on B cells and in liver and kidney and is a receptor for H-ferritin endocytosis," JEM 202(7):955-965, Oct. 2005. (11 pages).

Colman, "Effects of amino acid sequence changes on antibody-antigen interactions," Research in Immunology 145(1):33-36, 1994.

Cordoba et al., "The large ectodomains of CD45 and CD148 regulate their segregation from and inhibition of ligated T-cell receptor," Blood 121(21):4295-4302, 2013.

Delgado Tascón et al., "The granulocyte orphan receptor CEACAM4 is able to trigger phagocytosis of bacteria," Journal of Leukocyte Biology 97:521-531, Mar. 2015.

Dillon et al., "Annexin V Binds to Viable B Cells and Colocalizes with a Marker of Lipid Rafts upon B Cell Receptor Activation," The Journal of Immunology 164:1322-1332, 2000.

Dolezal et al., "ScFv multimers of the anti-neuraminidase antibody NC10: shortening of the linker in single-chain Fv fragment assembled in V(L) to V(H) orientation drives the formation of dimers, trimers, tetramers and higher molecular mass multimers," Protein Engineering 13(8):565-574, 2000.

Duclos et al., "Rab5 regulates the kiss and run fusion between phagosomes and endosomes and the acquisition of phagosome leishmanicidal properties in RAW 264.7 macrophages," Journal of Cell Science 113:3531-3541, 2000.

Engels et al., "Retroviral Vectors for High-Level Transgene Expression in T Lymphocytes," Human Gene Therapy 14:1155-1168, Aug. 2003.

Fesnak et al., "Engineered T Cells: The Promise and Challenges of Cancer Immunotherapy," Nature Reviews Cancer 16(9):566-581, Sep. 2016.

Frecha et al., "Advances in the Field of Lentivector-based Transduction of T and B Lymphocytes for Gene Therapy," Molecular Therapy 18(10):1748-1757, Oct. 2010.

Gerber et al., "Tumor-specific targeting by Bavituximab, a phosphatidylserine-targeting monoclonal antibody with vascular targeting and immune modulating properties, in lung cancer xenografts," Am. J. Nucl. Med. Mol. Imaging 5(5):493-503, 2015.

Green et al., "Mitochondria and Apoptosis," Science 281(5381):1309-1312, Aug. 1998.

Greenberg et al., "Clustered syk tyrosine kinase domains trigger phagocytosis," Proc. Natl. Acad. Sci. USA 93:1103-1107, Feb. 1996.

Greenberg, "Programmed cell death: A way of life for plants," Proc. Natl. Acad. Sci. USA 93:12094-12097, Oct. 1996.

Guest et al., "The Role of Extracellular Spacer Regions in the Optimal Design of Chimeric Immune Receptors: Evaluation of Four Different scFvs and Antigens," Journal of Immunotherapy 28(3):203-211, May/Jun. 2005.

Hanayama et al., "Identification of a factor that links apoptotic cells to phagocytes," Nature 417:182-187, May 2002.

Hartt Meyers et al., "TIM-4 is the ligand for TIM-1, and the TIM-1-TIM-4 interaction regulates T cell proliferation," Nat. Immunol. 6(5):455-464, May 2005.

Hayashi et al., "The innate immune response to bacterial flagellin is mediated by Toll-like receptor 5," Nature, 410(6832), Apr. 2001, pp. 1099-1103.

Hochreiter-Hufford et al., "Clearing the Dead: Apoptotic Cell Sensing, Recognition, Engulfment, and Digestion," Cold Spring Harb Perspect Biol 5:a008748, 2013. (21 pages).

(56) References Cited

OTHER PUBLICATIONS

Hudecek et al., "Receptor Affinity and Extracellular Domain Modifications Affect Tumor Recognition by ROR1-Specific Chimeric Antigen Receptor T Cells," Clin. Cancer Res. 19(12):3153-31564, 2013.
Hudecek et al., "The Nonsignaling Extracellular Spacer Domain of Chimeric Antigen Receptors is Decisive for In Vivo Antitumor Activity," Cancer Immunol. Res. 3(2):125-135, Feb. 2015.
Hull et al., "The Mononuclear Phagocyte System in Homeostasis and Disease: A Role for Heme Oxygenase-1," Antioxidants & Redox Signaling 20(11):1770-1788, 2014.
International Search Report and Written Opinion, mailed Aug. 19, 2019, for International Application No. PCT/US2019/024441, 13 pages.
International Search Report and Written Opinion, mailed Feb. 6, 2018, for International Application No. PCT/US2017/53553, 13 pages.
International Search Report and Written Opinion, mailed Jun. 28, 2019, for International Application No. PCT/US2019/024442, 12 pages.
International Search Report and Written Opinion, mailed Jun. 7, 2019, for International Application No. PCT/US2019/024433, 13 pages.
International Search Report and Written Opinion, mailed Mar. 25, 2019, for International Application No. PCT/US2018/052297, 10 pages.
International Search Report and Written Opinion, mailed May 29, 2019, for International Application No. PCT/US2019/024435, 12 pages.
Jones et al., "Lentiviral Vector Design for Optimal T Cell Receptor Gene Expression in the Transduction of Peripheral Blood Lymphocytes and Tumor-Infiltrating Lymphocytes," Human Gene Therapy 20:630-640, Jun. 2009.
June, "Adoptive T cell therapy for cancer in the clinic," The Journal of Clinical Investigation 117(6): 1466-1476, Jun. 2007.
Kao et al., "Systematic Comparison of the EF-1 Alpha Short (EFS) and Viral Promoters for Gene Modification of Human Primary Cells for Clinical Applications," Blood 124(21):3497, Dec. 6, 2014. (3 pages).
Khogeer et al., "Antiphosphatidylserine antibodies as diagnostic indicators of antiphospholipid syndrome," Lupus 24:186-190, 2015.
Kitchen et al., "Engineering Antigen-Specific T Cells from Genetically Modified Human Hematopoietic Stem Cells in Immunodeficient Mice," PLoS One 4(12):e8208, Dec. 2009.
Kobayashi et al., "TIM-1 and TIM-4 Glycoproteins Bind Phosphatidylserine and Mediate Uptake of Apoptotic Cells," Immunity 27:927-940, Dec. 2007.
Kochenderfer et al., "Construction and Pre-clinical Evaluation of an Anti-CD19 Chimeric Antigen Receptor," J. Immunother. 32(7):689-702, 2009.
Krisky et al., "Development of herpes simplex virus replication-defective multigene vectors for combination gene therapy applications," Gene Therapy 5:1517-1530, 1998.
Kruskal et al., "Phagocytic Chimeric Receptors Require Both Transmembrane and Cytoplasmic Domains from the Mannose Receptor," J. Exp. Med. 176:1673-1680, Dec. 1992.
Kuchroo et al., "The TIM Gene Family: Emerging Roles in Immunity and Disease," Nature Reviews. Immunology 3, No. 6 (May 30, 2003): 454-62, https://doi.org/10.1038/nri1111.
Luo et al., "Development of genetically engineered CD4+ and CD8+ T cells expressing TCRs specific for a M. tuberculosis 38-kDa antigen," Journal of Molecular Medicine 89:903-913, 2011.
Meyers et al. "TIM-4 is the Ligand for TIM-1, and the TIM-1-TIM-4 Interaction Regulates T Cell Proliferation." Nature Immunology 6, No. 5 (Mar. 27, 2005): 455-64. https://doi.org/10.1038/ni1185.
Miksa et al., "A novel method to determine the engulfment of apoptotic cells by macrophages using pHrodo succinimidyl ester," J Immunol Methods 342:71-77, 2009.

Misyurin, "Structure and Functions of Main Apoptosis Receptors and Ligands," Russian Journal of Biotherapy 14(2):23-30, 2015.
Miyanishi et al., "Identification of Tim4 as a phosphatidylserine receptor," Nature 450:435-439, Nov. 2007.
Moller-Tank et al., "Characterizing Functional Domains for TIM-Mediated Enveloped Virus Entry", J. Virology, Jun. 2014, 88(12): 6702-6713).
Morgan et al., "Cancer Regression in Patients After Transfer of Genetically Engineered Lymphocytes," Science 314(5796):126-129, Oct. 2006.
Morrissey et al., "Chimeric antigen receptors that trigger phagocytosis," eLife, 2018. (21 pages).
Muller et al., "Spliceosomal Peptide P140 for Immunotherapy of Systemic Lupus Erythematosus: Results of an Early Phase II Clinical Trial," Arthritis & Rheumatism 58(12):3873-3883, Dec. 2008.
Nakaya, "Research on Molecular Mechanisms of Engulfment of Apoptotic Cells", The Pharmaceutical Society of Japan 135(8):949-954, 2015.
Nishi et al., "Systematic characterization of deubiquitylating enzymes for roles in maintaining genome integrity," Nat Cell Biol. 16(10):1016-8, Oct. 2014. (27 pages).
Nishi et al., "Tim4- and MerTK-Mediated Engulfment of Apoptotic Cells by Mouse Resident Peritoneal Macrophages," Molecular and Cellular Biology 34(8):1512-1520, Apr. 2014.
Ohtsuka et al. "NFAMI, an immunoreceptor tyrosine-based activation motif-bearing molecule that regulates B cell development and signaling." Proc. Nat. Acad. Sci. 101: 8126-8131, 2004.
Ortiz, et al. "The evolutionary history of the CD209 (Dc-Sign) family in humans and non-human primates," Genes and Immunity, Jun. 2008, 2008(9), pp. 483-492.
Park et al., "The Phosphatidylserine Receptor TIM-4 Does Not Mediate Direct Signaling," Current Biology 19:346-351, Feb. 2009. (6 pages).
Penberthy et al., "Apoptotic cell recognition receptors and scavenger receptors," Immunological Reviews 269:44-59, 2016.
Pfeifer et al., "Gene Therapy: Promises and Problems," Annu. Rev. Genomics Hum. Genet. 2:177-211, 2001.
Qin, et al. "Prelinical Development of Bivalent Chimeric Antigen Receptors Targeting Both CD19 and CD22," Molecular Therapy: Oncolytics, vol. 11, Dec. 2018, pp. 127-137.
Ravichandran "Find-me and eat-me signals in apoptotic cell clearance: progress and conundrums, " J. Exp. Med. 207(9):1807-1817, 2017.
Rodriguez-Manzanet et al., "TIM-4 Expressed on APCs Induces T Cell Expansion and Survival," The Journal of Immunology 180, No. 7 (Apr. 1, 2008): 4706-13, https://doi.org/10.4049/jimmunol.180.7.4706.
Rossi et al., "Genetic therapies against HIV," Nat. Biotechnol. 25(12):1444-1454, Dec. 2007.
Sánchez-Fueyo et al., "Tim-3 Inhibits T Helper Type 1-mediated Auto- and Alloimmune Responses and Promotes Immunological Tolerance," Nature Immunology 4, No. 11 (Oct. 12, 2003): 1093-1101, https://doi.org/10.1038/ni987.
Sato et al., "Enhancement of Fcy Receptor-Mediated Phagocytosis by Transforming Mutants of Cbl1," The Journal of Immunology 163(11):6123-6131, 1999.
Schmitt et al., "T Cell Receptor Gene Therapy for Cancer," Human Gene Therapy 20:1240-1248, 2009.
Schutters et al., "Phosphatidylserine targeting for diagnosis and treatment of human diseases," Apoptosis 15:1072-1082, 2010.
Srivastava et al., "Engineering CAR-T Cells: Design Concepts," Trends Immunol. 36(8):494-502, 2015.
Stone et al., "A novel T cell receptor single-chain signaling complex mediates antigen-specific T cell activity and tumor control," Cancer Immunol. Immunother. 63(11 ): 1163-1176, Nov. 2014 (NIH Public Access Author Manuscript, available in PMC Nov. 1, 2015). (23 pages).
Takeshi, et al., "Regulation of Immunity by Toll-like Receptor Functions: Their Physiological and Pathological Roles," Journal of Gifu Dental Society, 2011?vol. 37?pp. 138-158.

(56) References Cited

OTHER PUBLICATIONS

Vallabhapurapu et al., "Variation in human cancer cell external phosphatidylserine is regulated by flippase activity and intracellular calcium," Oncotarget 6(33):34375-34388, 2015.

Verhoeyen et al., "Chapter 8: Lentiviral Vector Gene Transfer into Human T Cells," Methods Mol. Biol. 506:97-114, 2009.

Wälchli et al., "A Practical Approach to T-Cell Receptor Cloning and Expression," PLoS One 6(11):e27930, 2011. (11 pages).

Walseng et al., "A TCR-based Chimeric Antigen Receptor," Scientific Reports 7: 10713, 2017. (10 pages).

Wang et al., "A transgene-encoded cell surface polypeptide for selection, in vivo tracking, and ablation of engineered cells," Blood 118(5):1255-1263, Aug. 2011.

Williamson et al., "Abstract A165: Engineering approaches to uncover the mechanism of apoptotic cell clearance by a conserved signaling system," CRI-CIMT-EATI-AACR Inaugural International Cancer Immunotherapy Conference: Translating Science into Survival, New York, New York, Sep. 16-19, 2015. (6 pages).

Williamson et al., "Abstract PR15: Engineering phagocytic signaling," CRI-CIMT-EATI-AACR International Cancer Immunotherapy Conference: Translating Science into Survival, New York, New York, Sep. 25-28, 2016. (4 pages).

Williamson et al., "Cellular reconstitution of apoptotic cell clearance reveals a multi-step phosphorylation mechanism for Draper receptor triggering," bioRxiv: 1-48, 2017. (58 pages).

Williamson et al., "Spatial control of Draper receptor signaling initiates apoptotic cell engulfment," J. Cell Biol. 217(11):3977-3992, 2018.

Yang et al. "Calcineurin/nuclear factors of activated T cells (NFAT)-activating and immunoreceptor tyrosine-based activation motif (ITAM)-containing protein (CNAIP), a novel ITAM-containing protein that activates the calcineurin/NFAT-signaling pathway." J. Biol. Chem. 278: 16797-16801, 2003.

Yang et al., "Development of optimal bicistronic lentiviral vectors facilitates high-level TCR gene expression and robust tumor cell recognition," Gene Therapy 15:1411-1423, May 22, 2008. (13 pages).

Zaritskaya et al., "New flow cytometric assays for monitoring cell-mediated cytotoxicity," Expert Review of Vaccines 9(6):601-616, Jun. 2010. (26 pages).

Zhang et al., "Transduction of Human T Cells with a Novel T-Cell Receptor Confers Anti-HCV Reactivity," PLoS Pathogens 6(7):e1001018, Jul. 2010. (13 pages).

Zhao et al., "Primary Human Lymphocytes Transduced with NY-ESO-1 Antigen-Specific TCR Genes Recognize and Kill Diverse Human Tumor Cell Lines," J. Immunol. 174:(7):4415-4423, Apr. 2005. (25 pages).

\* cited by examiner

CHIMERIC TIM4 RECEPTORS AND USES THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is SeqList2-368779-40401.txt. The text file is 62,397, was created on May 29, 2024, and is being submitted electronically via EFS-Web.

BACKGROUND

Upon exposure to antigen, naïve antigen-specific CD8+ T cells undergo differentiation that promotes their clonal expansion and development into functional, effector T cells that can kill cells expressing the cognate antigen (e.g., tumor cells). Following antigen clearance, the majority of effector T cells undergo apoptosis, and a subset of the surviving effector T cells differentiate into memory T cells that can confer long-term protection against antigen re-exposure. However, prolonged antigen exposure may result in T cell exhaustion, enabling the persistence of tumor cells. T cell exhaustion refers to a dysfunctional state acquired by T cells experiencing persistent TCR stimulation characterized by upregulated expression of immune checkpoint molecules (e.g., PD-1, CTLA-4, Tim-3), impaired effector function, poor proliferation, and metabolic defects. Engineered T cells expressing chimeric antigen receptors (CARs) can also develop exhaustion.

DETAILED DESCRIPTION

In one aspect, the present disclosure provides chimeric T-cell immunoglobulin mucin protein 4 (Tim4) receptors. Chimeric Tim4 receptors of the present disclosure confer cytotoxic activity to chimeric Tim4 receptor-modified host cells, with the cytolytic activity being induced upon binding of the chimeric Tim4 receptor to its target antigen, phosphatidylserine. Embodiments of the chimeric Tim4 receptors described herein comprise a single chain chimeric protein, the single chain chimeric protein comprising: an extracellular domain comprising a Tim4 binding domain; an intracellular signaling domain comprising a first costimulatory signaling domain; and a transmembrane domain positioned between and connecting the extracellular domain and the intracellular signaling domain. In certain embodiments, the extracellular domain of the chimeric Tim4 receptors described herein optionally includes an extracellular spacer domain positioned between and connecting the binding domain and transmembrane domain.

In certain embodiments, cytotoxic chimeric Tim4 receptors may also be capable of costimulating T cells via a different signaling pathway than the "classical" T cell costimulation pathways (e.g., CD28). In addition to binding phosphatidylserine, Tim4 is also a ligand for Tim1, which is expressed on the surface of activated T cells. Tim4-induced Tim1 signaling has been found to costimulate T cell proliferation and survival (Hartt Meyers et al., 2005, Nat. Immunol. 6:455). Thus, in certain embodiments, cytotoxic chimeric Tim4 receptors may reduce or inhibit T cell exhaustion, or restore exhausted T cells by providing costimulatory signals via at least one signaling pathway. In certain embodiments, cytotoxic chimeric Tim4 receptors provide costimulatory signals via at least two distinct signaling pathways (e.g., via the selected costimulatory signaling domain in the cytotoxic chimeric Tim4 receptor and Tim1).

In certain embodiments, when expressed in a host cell, the chimeric Tim4 receptors of the present disclosure also confer engulfment activity to the host cell. For example, in certain such embodiments, binding of the chimeric Tim4 receptor expressed in a host cell to a phosphatidylserine target may induce both cytolytic and engulfment responses by the host cell. In particular embodiments of modified host cells described herein, the host cell does not naturally exhibit an engulfment phenotype prior to modification with the chimeric Tim4 receptor.

In another aspect, host cells modified with chimeric Tim4 receptors of the present disclosure can be used in methods for eliminating target cells bearing surface exposed phosphatidylserine, e.g., for the treatment of cancer. In normal, healthy cells phosphatidylserine is located in the inner leaflet of the plasma membrane. However, certain cellular events, such as damage, apoptosis, necrosis, and stress, activates a "scramblase" that quickly exposes phosphatidylserine on the cell surface, where it can bind to receptors such as Tim4. Endogenous tumor-specific effector T cells can induce exposure of phosphatidylserine on the outer membrane of targeted tumor cells during cytolysis. Furthermore, certain cancer therapies (e.g., chemotherapy, radiotherapy, CAR-T cells, etc.) can induce exposure of phosphatidylserine on targeted tumor cells or cells in the tumor microenvironment by inducing apoptosis, cellular stress, cellular damage, etc. Host cells expressing the presently disclosed chimeric Tim4 receptors may clear damaged, stressed, apoptotic, or necrotic tumor cells bearing surface exposed phosphatidylserine by inducing apoptosis in the tumor cells bearing surface exposed phosphatidylserine. In certain embodiments, host cells expressing chimeric Tim4 receptors disclosed herein clear damaged, stressed, apoptotic, or necrotic tumor cells bearing surface exposed phosphatidylserine by inducing apoptosis and by engulfment. Host cells comprising chimeric Tim4 receptors according to the present description may be administered to a subject alone, or in combination with one or more additional therapeutic agents, including for example CAR-T cells, TCRs, antibodies, radiation therapy, chemotherapies, small molecules, oncolytic viruses, electropulse therapy, etc.

In another aspect, host cells modified with chimeric Tim4 receptors of the present disclosure can be used in methods for enhancing an effector response (e.g., a tumor specific immune response). Embodiments of the chimeric Tim4 receptors of the present disclosure are capable of costimulating T cells via at least one costimulatory signaling pathway upon binding phosphatidylserine. In certain embodiments, the chimeric Tim4 receptors described herein provide costimulatory signals via at least two distinct signaling pathways. In certain embodiments, the enhanced effector response is enhanced T cell proliferation, cytokine production, cytotoxic activity, persistence, or any combination thereof. Host cells expressing chimeric Tim4 receptors according to the present description may be administered to a subject alone, or in combination with one or more additional therapeutic agents, including for example CAR-T cells, TCRs, antibodies, radiation therapy, chemotherapies, small molecules, oncolytic viruses, electropulse therapy, etc.

In another aspect, host cells modified with chimeric Tim4 receptors of the present disclosure can be used in methods for inhibiting or reducing immune cell exhaustion. In certain embodiments, immune cell exhaustion refers to T cell exhaustion, NK cell exhaustion, or both. Tumor cells may provide continuous antigen stimulation to immune cells, often in the absence of costimulatory ligands, which may result in immune cell exhaustion (e.g., reduced proliferative capacity, reduced effector function, and upregulation of immunosuppressive molecules). Cancer therapies, such as chemotherapy, radiotherapy, CAR-T cell therapy, etc., can also provide prolonged antigen stimulation in the absence of costimulatory signals or when the strength or duration of costimulatory signals is limited. Chimeric Tim4 receptors of the present disclosure are capable of costimulating immune cells via at least one costimulatory signaling domain upon binding phosphatidylserine. In certain embodiments, chimeric Tim4 receptors provide costimulatory signals via at least two distinct signaling pathways. Host cells expressing chimeric Tim4 receptors may be administered to a subject alone, or in combination with one or more additional therapeutic agents, including for example CAR-T cells, TCRs, antibodies, radiation therapy, chemotherapies, small molecules, oncolytic viruses, electropulse therapy, etc.

In another aspect, host cells modified with chimeric Tim4 receptors of the present disclosure can be used to enhance the effect of a therapeutic agent that induces cellular stress, damage, necrosis, or apoptosis. For example, certain therapeutic agents, such as chemotherapy, specific inhibitors of driver mutations associated with cancer (targeted therapy such as BRAF inhibitors, EGRF inhibitors, ALK/ROS1 kinase inhibitors), radiation therapy, UV light therapy, electropulse therapy, adoptive cellular immunotherapy (e.g., CAR-T cells, TCRs) and oncolytic viral therapy, can induce cell damage or death in tumor cells or diseased cells. Cells expressing a chimeric Tim4 receptor as presently described can bind to the phosphatidylserine moieties exposed on the outer leaflet of damaged or dying cells resulting from any one or more of such therapeutic agents and induce cytolysis or both cytolysis and engulfment of the targeted cells.

Prior to setting forth this disclosure in more detail, it may be helpful to an understanding thereof to provide definitions of certain terms to be used herein.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

Terms understood by those in the art of antibody technology are each given the meaning acquired in the art, unless expressly defined differently herein. The term "antibody" is used in the broadest sense and includes polyclonal and monoclonal antibodies. An "antibody" may refer to an intact antibody comprising at least two heavy (H) chains and two light (L) chains inter-connected by disulfide bonds, as well as an antigen-binding portion (or antigen-binding domain) of an intact antibody that has or retains the capacity to bind a target molecule. An antibody may be naturally occurring, recombinantly produced, genetically engineered, or modified forms of immunoglobulins, for example intrabodies, peptibodies, nanobodies, single domain antibodies, SMIPs, multispecific antibodies (e.g., bispecific antibodies, diabodies, triabodies, tetrabodies, tandem di-scFV, tandem tri-scFv, ADAPTIR). A monoclonal antibody or antigen-binding portion thereof may be non-human, chimeric, humanized, or human, preferably humanized or human. Immunoglobulin structure and function are reviewed, for example, in Harlow et al., Eds., Antibodies: A Laboratory Manual, Chapter 14 (Cold Spring Harbor Laboratory, Cold Spring Harbor, 1988). "Antigen-binding portion" or "antigen-binding domain" of an intact antibody is meant to encompass an "antibody fragment," which indicates a portion of an intact antibody and refers to the antigenic determining variable regions or complementary determining regions of an intact antibody. Examples of antibody fragments include, but are not limited to, Fab, Fab', F(ab')$_2$, and Fv fragments, Fab'-SH, F(ab')$_2$, diabodies, linear antibodies, scFv antibodies, VH, and multispecific antibodies formed from antibody fragments. A "Fab" (fragment antigen binding) is a portion of an antibody that binds to antigens and includes the variable region and CH1 of the heavy chain linked to the light chain via an inter-chain disulfide bond. An antibody may be of any class or subclass, including IgG and subclasses thereof (IgG$_1$, IgG$_2$, IgG$_3$, IgG$_4$), IgM, IgE, IgA, and IgD.

The term "variable region" or "variable domain" refers to the domain of an antibody heavy or light chain that is involved in binding of the antibody to antigen. The variable domains of the heavy chain and light chain (VH and VL, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007)). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The terms "complementarity determining region" and "CDR," which are synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (HCDR1, HCDR2, HCDR3) and three CDRs in each light chain variable region (LCDR1, LCDR2, LCDR3).

As used herein, the terms "binding domain", "binding region", and "binding moiety" refer to a molecule, such as a peptide, oligopeptide, polypeptide, or protein that possesses the ability to specifically and non-covalently bind, associate, unite, recognize, or combine with a target molecule (e.g., phosphatidylserine). A binding domain includes any naturally occurring, synthetic, semi-synthetic, or recombinantly produced binding partner for a biological molecule or other target of interest. In some embodiments, the binding domain is an antigen-binding domain, such as an antibody or functional binding domain or antigen-binding portion thereof. Exemplary binding domains include single chain antibody variable regions (e.g., domain antibodies, sFv, scFv, Fab), receptor ectodomains (e.g., Tim4), ligands (e.g., cytokines, chemokines), or synthetic polypeptides selected for the specific ability to bind to a biological molecule.

"T cell receptor" (TCR) refers to a molecule found on the surface of T cells (also referred to as T lymphocytes) that is generally responsible for recognizing antigens bound to major histocompatibility complex (MEW) molecules. The TCR is generally composed of a disulfide-linked heterodimer of the highly variable α and β chains (also known as TCRα and TCRβ, respectively) in most T cells. In a small subset of T cells, the TCR is made up of a heterodimer of γ and δ chains (also known as TCRγ and TCRδ, respectively). Each chain of the TCR is a member of the immunoglobulin superfamily and possesses one N-terminal immunoglobulin variable domain, one immunoglobulin constant domain, a transmembrane region, and a short cytoplasmic tail at the C-terminal end (see Janeway et al., *Immunobiology: The Immune System in Health and Disease*, 3$^{rd}$ Ed., Current Biology Publications, p. 4:33, 1997). TCRs of the present disclosure may be from various animal species, including human, mouse, rat, cat, dog, goat, horse, or other mammals. TCRs may be cell-bound (i.e., have a transmembrane region or domain) or in soluble form. TCRs include recombinantly produced, genetically engineered, fusion, or modified forms of TCRs, including for example, scTCRs, soluble TCRs, TCR fusion constructs (TRuC™; see, U.S. Patent Publication No. 2017/0166622).

The term "variable region" or "variable domain" of a TCR α-chain (Vα) and β-chain (Vβ), or Vγ and Vδ for γδ TCRs, are involved in binding of the TCR to antigen. The $V_\alpha$ and $V_\beta$ of a native TCR generally have similar structures, with each variable domain comprising four conserved FRs and three CDRs. The $V_\alpha$ domain is encoded by two separate DNA segments, the variable gene segment (V gene) and the joining gene segment (J gene); the $V_\beta$ domain is encoded by three separate DNA segments, the variable gene segment (V gene), the diversity gene segment (D gene), and the joining gene segment (J gene). A single $V_\alpha$ or $V_\beta$ domain may be sufficient to confer antigen-binding specificity. "Major histocompatibility complex molecule" (MEW molecule) refers to a glycoprotein that delivers a peptide antigen to a cell surface. MHC class I molecules are heterodimers composed of a membrane spanning α chain (with three α domains) and a non-covalently associated β2 microglobulin. MEW class II molecules are composed of two transmembrane glycoproteins, α and β, both of which span the membrane. Each chain has two domains. MEW class I molecules deliver peptides originating in the cytosol to the cell surface, where peptide:MHC complex is recognized by CD8$^+$ T cells. MHC class II molecules deliver peptides originating in the vesicular system to the cell surface, where they are recognized by CD4$^+$ T cells. An MEW molecule may be from various animal species, including human, mouse, rat, or other mammals.

"Chimeric antigen receptor" (CAR) refers to a chimeric protein comprising two or more distinct domains and can function as a receptor when expressed on the surface of a cell. CARs are generally composed of an extracellular domain comprising a binding domain that binds a target antigen, an optional extracellular spacer domain, a transmembrane domain, and an intracellular signaling domain (e.g., an immunoreceptor tyrosine-based activation motif (ITAM)-containing T cell activating motif, and optionally an intracellular costimulatory domain). In certain embodiments, an intracellular signaling domain of a CAR has an ITAM-containing T cell activating domain (e.g., CD3ζ) and an intracellular costimulatory domain (e.g., CD28). In certain embodiments, a CAR is synthesized as a single polypeptide chain or is encoded by a nucleic acid molecule as a single chain polypeptide.

A variety of assays are known for identifying binding domains of the present disclosure that specifically bind a particular target, as well as determining binding domain affinities, such as Western blot, ELISA, and BIACORE® analysis (see also, e.g., Scatchard et al., *Ann. N.Y. Acad. Sci.* 51:660, 1949; and U.S. Pat. Nos. 5,283,173, 5,468,614, or the equivalent). As used herein, "specifically binds" refers to an association or union of a binding domain, or a fusion protein thereof, to a target molecule with an affinity or $K_a$ (i.e., an equilibrium association constant of a particular binding interaction with units of 1/M) equal to or greater than $10^5$ M$^{-1}$, while not significantly associating or uniting with any other molecules or components in a sample.

The terms "antigen" and "Ag" refer to a molecule that is capable of inducing an immune response. The immune response that is induced may involve antibody production, the activation of specific immunologically-competent cells, or both. Macromolecules, including proteins, glycoproteins, and glycolipids, can serve as an antigen. Antigens can be derived from recombinant or genomic DNA. As contemplated herein, an antigen need not be encoded (i) solely by a full length nucleotide sequence of a gene or (ii) by a "gene" at all. An antigen can be generated or synthesized, or an antigen can be derived from a biological sample. Such a biological sample can include, but is not limited to, a tissue sample, a tumor sample, a cell, or a biological fluid.

The term "epitope" or "antigenic epitope" includes any molecule, structure, amino acid sequence or protein determinant within an antigen that is specifically bound by a cognate immune binding molecule, such as an antibody or fragment thereof (e.g., scFv), T cell receptor (TCR), chimeric Tim4 receptor, or other binding molecule, domain or protein. Epitopic determinants generally contain chemically active surface groupings of molecules, such as amino acids or sugar side chains, and can have specific three dimensional structural characteristics, as well as specific charge characteristics. An epitope may be a linear epitope or a conformational epitope.

As used herein, the term "Tim4" (T-cell immunoglobulin and mucin domain containing protein 4), also known as "TimD4", refers to a phosphatidylserine receptor that is typically expressed on antigen presenting cells, such as macrophages and dendritic cells. Tim4 mediates the phagocytosis of apoptotic, necrotic, damaged, injured, or stressed cells, which present phosphatidylserine (PtdSer) on the exofacial (outer) leaflet of the cell membrane. Tim4 is also capable of binding to Tim1 expressed on the surface of T cells and inducing proliferation and survival. In certain embodiments, Tim4 refers to human Tim4. An exemplary human Tim4 protein comprises an amino acid sequence of SEQ ID NO:1.

As used herein, the term "Tim4 binding domain" refers to the N-terminal immunoglobulin-fold domain of Tim4 that possesses a metal ion-dependent pocket that selectively binds PtdSer. An exemplary human Tim4 binding domain comprises an amino acid sequence of SEQ ID NO:2, and an exemplary mouse Tim4 binding domain comprises an amino acid sequence of SEQ ID NO:60. In certain embodiments, the Tim4 binding domain does not include a signal peptide.

As used herein, an "effector domain" is an intracellular portion of a fusion protein or receptor that can directly or indirectly promote a biological or physiological response in a cell expressing the effector domain when receiving the appropriate signal. In certain embodiments, an effector domain is part of a protein or protein complex that receives a signal when bound, or it binds directly to a target molecule, which triggers a signal from the effector domain. An effector domain may directly promote a cellular response when it contains one or more signaling domains or motifs, such as an immunoreceptor tyrosine-based activation motif (ITAM).

In other embodiments, an effector domain will indirectly promote a cellular response by associating with one or more other proteins that directly promote a cellular response.

As used herein, a "costimulatory signaling domain" refers to an intracellular signaling domain, or functional portion thereof, of a costimulatory molecule, which, when activated in conjunction with a primary or classic (e.g., ITAM-driven) activation signal (provided by, for example, a CD3ζ intracellular signaling domain), promotes or enhances a T cell response, such as T cell activation, cytokine production, proliferation, differentiation, survival, effector function, or combinations thereof. Costimulatory signaling domains include, for example, CD27, CD28, CD40L, GITR, NKG2C, CARD1, CD2, CD7, CD27, CD30, CD40, CD54 (ICAM), CD83, CD134 (OX-40), CD137 (4-1BB), CD150 (SLAMF1), CD152 (CTLA4), CD223 (LAG3), CD226, CD270 (HVEM), CD273 (PD-L2), CD274 (PD-L1), CD278 (ICOS), DAP10, LAT, LFA-1, LIGHT, NKG2C, SLP76, TRIM, ZAP70, or any combination thereof.

As used herein, an "immunoreceptor tyrosine-based activation motif (ITAM) activating domain" refers to an intracellular signaling domain or functional portion thereof which is naturally or endogenously present on an immune cell receptor or a cell surface marker and contains at least one immunoreceptor tyrosine-based activation motif (ITAM). ITAM refers to a conserved motif of YXXL/I-$X_{6-8}$-YXXL/I. In certain embodiments an ITAM signaling domain contains one, two, three, four, or more ITAMs. An ITAM signaling domain may initiate T cell activation signaling following antigen binding or ligand engagement. ITAM-signaling domains include, for example, intracellular signaling domains of CD3γ, CD3δ, CD3ε, CD3ζ, CD79a, and CD66d.

"Junction amino acids" or "junction amino acid residues" refer to one or more (e.g., about 2-20) amino acid residues between two adjacent motifs, regions or domains of a polypeptide. Junction amino acids may result from the construct design of a chimeric protein (e.g., amino acid residues resulting from the use of a restriction enzyme site during the construction of a nucleic acid molecule encoding a chimeric protein).

"Nucleic acid molecule" and "polynucleotide" can be in the form of RNA or DNA, which includes cDNA, genomic DNA, and synthetic DNA. A nucleic acid molecule may be composed of naturally occurring nucleotides (such as deoxyribonucleotides and ribonucleotides), analogs of naturally occurring nucleotides (e.g., α-enantiomeric forms of naturally occurring nucleotides), or a combination of both. Modified nucleotides can have modifications in or replacement of sugar moieties, or pyrimidine or purine base moieties. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. A nucleic acid molecule may be double stranded or single stranded, and if single stranded, may be the coding strand or non-coding (anti-sense strand). A coding molecule may have a coding sequence identical to a coding sequence known in the art or may have a different coding sequence, which, as the result of the redundancy or degeneracy of the genetic code, or by splicing, can encode the same polypeptide.

"Encoding" refers to the inherent property of specific polynucleotide sequences, such as DNA, cDNA, and mRNA sequences, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a polynucleotide encodes a protein if transcription and translation of mRNA corresponding to that polynucleotide produces the protein in a cell or other biological system. Both a coding strand and a non-coding strand can be referred to as encoding a protein or other product of the polynucleotide. Unless otherwise specified, a "nucleotide sequence encoding an amino acid sequence" includes all nucleotide sequences that are degenerate versions of each other and that encode the same amino acid sequence.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, the term "mature polypeptide" or "mature protein" refers to a protein or polypeptide that is secreted or localized in the cell membrane or inside certain cell organelles (e.g., the endoplasmic reticulum, golgi, or endosome) and does not include an N-terminal signal peptide.

A "signal peptide", also referred to as "signal sequence", "leader sequence", "leader peptide", "localization signal" or "localization sequence", is a short peptide (usually 15-30 amino acids in length) present at the N-terminus of newly synthesized proteins that are destined for the secretory pathway. A signal peptide typically comprises a short stretch of hydrophilic, positively charged amino acids at the N-terminus, a central hydrophobic domain of 5-15 residues, and a C-terminal region with a cleavage site for a signal peptidase. In eukaryotes, a signal peptide prompts translocation of the newly synthesized protein to the endoplasmic reticulum where it is cleaved by the signal peptidase, creating a mature protein that then proceeds to its appropriate destination.

The term "chimeric" refers to any nucleic acid molecule or protein that is not endogenous and comprises sequences joined or linked together that are not normally found joined or linked together in nature. For example, a chimeric nucleic acid molecule may comprise regulatory sequences and coding sequences that are derived from different sources, or regulatory sequences and coding sequences that are derived from the same source but arranged in a manner different than that found in nature.

As used herein, the term "endogenous" or "native" refers to a gene, protein, compound, molecule or activity that is normally present in a host or host cell, including naturally occurring variants of the gene, protein, compound, molecule, or activity.

As used herein, "homologous" or "homolog" refers to a molecule or activity from a host cell that is related by ancestry to a second gene or activity, e.g., from the same host cell, from a different host cell, from a different organism, from a different strain, from a different species. For example, a heterologous molecule or heterologous gene encoding the molecule may be homologous to a native host cell molecule or gene that encodes the molecule, respectively, and may optionally have an altered structure, sequence, expression level or any combination thereof.

As used herein, "heterologous" nucleic acid molecule, construct or sequence refers to a nucleic acid molecule or portion of a nucleic acid molecule that is not native to a host cell, but can be homologous to a nucleic acid molecule or portion of a nucleic acid molecule from the host cell. The source of the heterologous nucleic acid molecule, construct or sequence can be from a different genus or species. In some embodiments, the heterologous nucleic acid molecules are not naturally occurring. In certain embodiments, a heterologous nucleic acid molecule is added (i.e., not endogenous or native) into a host cell or host genome by, for example, conjugation, transformation, transfection, transduction, electroporation, or the like, wherein the added molecule can integrate into the host cell genome or exist as extra-chromosomal genetic material (e.g., as a plasmid or other form of self-replicating vector), and can be present in multiple copies. In addition, "heterologous" refers to a non-native enzyme, protein or other activity encoded by a non-endogenous nucleic acid molecule introduced into the host cell, even if the host cell encodes a homologous protein or activity.

As used herein, the term "engineered," "recombinant," "modified" or "non-natural" refers to an organism, microorganism, cell, nucleic acid molecule, or vector that has been modified by introduction of a heterologous nucleic acid molecule, or refers to a cell or microorganism that has been genetically engineered by human intervention—that is, modified by introduction of a heterologous nucleic acid molecule, or refers to a cell or microorganism that has been altered such that expression of an endogenous nucleic acid molecule or gene is controlled, deregulated or constitutive, where such alterations or modifications can be introduced by genetic engineering. Human-generated genetic alterations can include, for example, modifications introducing nucleic acid molecules (which may include an expression control element, such as a promoter) encoding one or more proteins, chimeric receptors, or enzymes, or other nucleic acid molecule additions, deletions, substitutions, or other functional disruption of or addition to a cell's genetic material. Exemplary modifications include those in coding regions or functional fragments thereof heterologous or homologous polypeptides from a reference or parent molecule. Additional exemplary modifications include, for example, modifications in non-coding regulatory regions in which the modifications alter expression of a gene or operon.

As used herein, the term "transgene" refers to a gene or polynucleotide encoding a protein of interest (e.g., chimeric Tim4 receptor) whose expression is desired in a host cell and that has been transferred by genetic engineering techniques into a cell. A transgene may encode proteins of therapeutic interest as well as proteins that are reporters, tags, markers, suicide proteins, etc. A transgene may be from a natural source, modification of a natural gene, or a recombinant or synthetic molecule. In certain embodiments, a transgene is a component of a vector.

The term "overexpressed" or "overexpression" of an antigen refers to an abnormally high level of antigen expression in a cell. Overexpressed antigen or overexpression of antigen is often associated with a disease state, such as in hematological malignancies and cells forming a solid tumor within a specific tissue or organ of a subject. Solid tumors or hematological malignancies characterized by overexpression of a tumor antigen can be determined by standard assays known in the art.

The "percent identity" between two or more nucleic acid or amino acid sequences is a function of the number of identical positions shared by the sequences (i.e., % identity=number of identical positions/total number of positions×100), taking into account the number of gaps, and the length of each gap that needs to be introduced to optimize alignment of two or more sequences. The comparison of sequences and determination of percent identity between two or more sequences can be accomplished using a mathematical algorithm, such as BLAST and Gapped BLAST programs at their default parameters (e.g., Altschul et al., *J. Mol. Biol.* 215:403, 1990; see also BLASTN at www.ncbi.nlm.nih.gov/BLAST).

A "conservative substitution" is recognized in the art as a substitution of one amino acid for another amino acid that has similar properties. Exemplary conservative substitutions are well known in the art (see, e.g., WO 97/09433, page 10, published Mar. 13, 1997; Lehninger, Biochemistry, Second Edition; Worth Publishers, Inc. NY:NY (1975), pp. 71-'7'7; Lewin, Genes IV, Oxford University Press, NY and Cell Press, Cambridge, MA (1990), p. 8).

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

The phrase "under transcriptional control" or "operatively linked" as used herein means that a promoter is in the correct location and orientation in relation to a polynucleotide to control the initiation of transcription by RNA polymerase and expression of the polynucleotide.

A "vector" is a nucleic acid molecule that is capable of transporting another nucleic acid. Vectors may be, for example, plasmids, cosmids, viruses, or phage. The term should also be construed to include non-plasmid and non-viral compounds which facilitate transfer of nucleic acid into cells. An "expression vector" is a vector that is capable of directing the expression of a protein encoded by one or more genes carried by the vector when it is present in the appropriate environment.

In certain embodiments, the vector is a viral vector. Examples of viral vectors include, but are not limited to, adenovirus vectors, adeno-associated virus vectors, retrovirus vectors, gamma retrovirus vectors, and lentivirus vectors. "Retroviruses" are viruses having an RNA genome. "Gamma retrovirus" refers to a genus of the retroviridae family. Examples of gamma retroviruses include mouse stem cell virus, murine leukemia virus, feline leukemia virus, feline sarcoma virus, and avian reticuloendotheliosis viruses. "Lentivirus" refers to a genus of retroviruses that are capable of infecting dividing and non-dividing cells. Examples of lentiviruses include, but are not limited to HIV (human immunodeficiency virus, including HIV type 1 and HIV type 2, equine infectious anemia virus, feline immunodeficiency virus (FIV), bovine immune deficiency virus (BIV), and simian immunodeficiency virus (SIV).

In other embodiments, the vector is a non-viral vector. Examples of non-viral vectors include lipid-based DNA vectors, modified mRNA (modRNA), self-amplifying mRNA, closed-ended linear duplex (CELiD) DNA, and transposon-mediated gene transfer (PiggyBac, Sleeping Beauty). Where a non-viral delivery system is used, the delivery vehicle can be a liposome. Lipid formulations can be used to introduce nucleic acids into a host cell in vitro, ex vivo, or in vivo. The nucleic acid may be encapsulated in the interior of a liposome, interspersed within the lipid bilayer of a liposome, attached to a liposome via a linking molecule that is associated with both the liposome and the nucleic acid, contained or complexed with a micelle, or otherwise associated with a lipid.

As used herein, the term "engulfment" refers to a receptor-mediated process wherein endogenous or exogenous cells or particles greater than 100 nm in diameter are internalized by a phagocyte or host cell of the present disclosure. Engulfment is typically composed of multiple steps: (1) tethering of the target cell or particle via binding of an engulfment receptor to a pro-engulfment marker or antigenic marker directly or indirectly (via a bridging molecule) on a target cell or particle; and (2) internalization or engulfment of the whole target cell or particle, or a portion thereof. In certain embodiments, internalization may occur via cytoskeletal rearrangement of a phagocyte or host cell to form a phagosome, a membrane-bound compartment containing the internalized target. Engulfment may further include maturation of the phagosome, wherein the phagosome becomes increasingly acidic and fuses with lysosomes (to form a phagolysosome), whereupon the engulfed target is degraded (e.g., "phagocytosis"). Alternatively, phagosome-lysosome fusion may not be observed in engulfment. In yet another embodiment, a phagosome may regurgitate or discharge its contents to the extracellular environment before complete degradation. In some embodiments, engulfment refers to phagocytosis. In some embodiments, engulfment includes tethering of the target cell or particle by the phagocyte of host cell of the present disclosure, but not internalization. In some embodiments, engulfment includes tethering of the target cell or particle by the phagocyte of host cell of the present disclosure and internalization of part of the target cell or particle.

As used herein, the term "phagocytosis" refers to an engulfment process of cells or large particles (≥0.5 μm) wherein tethering of a target cell or particle, engulfment of the target cell or particle, and degradation of the internalized target cell or particle occurs. In certain embodiments, phagocytosis comprises formation of a phagosome that encompasses the internalized target cell or particle and phagosome fusion with a lysosome to form a phagolysosome, wherein the contents therein are degraded. In certain embodiments, during phagocytosis, following binding of a chimeric Tim4 receptor expressed on a host cell of the present disclosure to a phosphatidylserine expressed by a target cell or particle, a phagocytic synapse is formed; an actin-rich phagocytic cup is generated at the phagocytic synapse; phagocytic arms are extended around the target cell or particle through cytoskeletal rearrangements; and ultimately, the target cell or particle is pulled into the phagocyte or host cell through force generated by motor proteins. As used herein, "phagocytosis" includes the process of "efferocytosis", which specifically refers to the phagocytosis of apoptotic or necrotic cells in a non-inflammatory manner.

The term "immune system cell" or "immune cell" means any cell of the immune system that originates from a hematopoietic stem cell in the bone marrow. Hematopoietic stem cells give rise to two major lineages, a myeloid progenitor cell (which give rise to myeloid cells such as monocytes, macrophages, dendritic cells, megakaryocytes and granulocytes) and a lymphoid progenitor cell (which give rise to lymphoid cells such as T cells, B cells and natural killer (NK) cells). Exemplary immune system cells include a CD4+ T cell, a CD8+ T cell, a CD4− CD8− double negative T cell, a γδ T cell, a regulatory T cell, a natural killer cell, and a dendritic cell. Macrophages and dendritic cells may also be referred to as "antigen presenting cells" or "APCs," which are specialized cells that can activate T cells when a major histocompatibility complex (MHC) receptor on the surface of the APC complexed with a peptide interacts with a TCR on the surface of a T cell.

The term "T cells" refers to cells of T cell lineage. "Cells of T cell lineage" refer to cells that show at least one phenotypic characteristic of a T cell or a precursor or progenitor thereof that distinguishes the cells from other lymphoid cells, and cells of the erythroid or myeloid lineages. Such phenotypic characteristics can include expression of one or more proteins specific for T cells (e.g., $CD3^+$, $CD4^+$, $CD8^+$), or a physiological, morphological, functional, or immunological feature specific for a T cell. For example, cells of the T cell lineage may be progenitor or precursor cells committed to the T cell lineage; $CD25^+$ immature and inactivated T cells; cells that have undergone CD4 or CD8 linage commitment; thymocyte progenitor cells that are $CD4^+CD8^+$ double positive; single positive $CD4^+$ or $CD8^+$; TCRαβ or TCR γδ; or mature and functional or activated T cells. The term "T cells" encompasses naïve T cells (CD45 RA+, CCR7+, CD62L+, CD27+, CD45RO−), central memory T cells ($CD45RO^+$, $CD62L^+$, $CD8^+$), effector memory T cells (CD45RA+, CD45RO−, CCR7−, CD62L−, CD27−), mucosal-associated invariant T (MAIT) cells, Tregs, natural killer T cells, and tissue resident T cells.

The term "B cells" refers to cells of the B cell lineage. "Cells of B cell lineage" refer to cells that show at least one phenotypic characteristic of a B cell or a precursor or progenitor thereof that distinguishes the cells from other lymphoid cells, and cells of the erythroid or myeloid lineages. Such phenotypic characteristics can include expression of one or more proteins specific for B cells (e.g., $CD19^+$, CD72+, CD24+, $CD20^+$), or a physiological, morphological, functional, or immunological feature specific for a B cell. For example, cells of the B cell lineage may be progenitor or precursor cells committed to the B cell lineage (e.g., pre-pro-B cells, pro-B cells, and pre-B cells); immature and inactivated B cells or mature and functional or activated B cells. Thus, "B cells" encompass naïve B cells, plasma cells, regulatory B cells, marginal zone B cells, follicular B cells, lymphoplasmacytoid cells, plasmablast cells, and memory B cells (e.g., CD27$^+$, IgD$^-$).

The term "cytotoxic activity," also referred to as "cytolytic activity," with respect to a cell (e.g., a T cell or NK cell) expressing an immune receptor (e.g., a TCR) or a chimeric Tim4 receptor according to the present disclosure on its surface, means that upon antigen-specific signaling (e.g., via the TCR, chimeric Tim4 receptor), the cell induces a target cell to undergo apoptosis. In some embodiments, a cytotoxic cell may induce apoptosis in a target cell via the release of cytotoxins, such as perforin, granzyme, and granulysin, from granules. Perforins insert into the target cell membrane and form pores that allow water and salts to rapidly enter the target cell. Granzymes are serine proteases that induce apoptosis in the target cell. Granulysin is also capable of forming pores in the target cell membrane and is a proinflammatory molecule. In some embodiments, a cytotoxic cell may induce apoptosis in a target cell via interaction of Fas ligand, which is upregulated on T cell following antigen-specific signaling, with Fas molecules expressed on the target cell. Fas is an apoptosis-signaling receptor molecule on the surface of a number of different cells.

The term "exhaustion" with respect to immune cells refers to a state of immune cell dysfunction defined by poor effector function (e.g., reduced cytokine production, reduced cytotoxic activity), reduced proliferative capacity, increased expression of immune checkpoint molecules, and a transcriptional state distinct from that of functional effector or memory cells. In certain embodiments, an exhausted immune cell becomes unresponsive to the presence of its target antigen. Immune cell exhaustion may result from chronic exposure to a target antigen (e.g., as may result from chronic infection) or when it enters an immunosuppressive environment (e.g., a tumor microenvironment). In certain embodiments, immune cell exhaustion refers to T cell exhaustion, NK cell exhaustion, or both. In certain embodiments, exhausted T cells exhibit; (a) increased expression of PD-1, TIGIT, LAG3, TIM3, or any combination thereof; (b) decreased production of IFN-γ, IL-2, TNF-α, or any combination thereof; or both (a) and (b). In certain embodiments, exhausted NK cells exhibit; (a) increased expression of PD-1, NKG2A, TIM3, or any combination thereof; (b) decreased production of IFN-γ, TNF-α, or both; or both (a) and (b).

A "disease" is a state of health of a subject wherein the subject cannot maintain homeostasis, and wherein, if the disease is not ameliorated, then the subject's health continues to deteriorate. In contrast, a "disorder" or "undesirable condition" in a subject is a state of health in which the subject is able to maintain homeostasis, but in which the subject's state of health is less favorable than it would be in the absence of the disorder or undesirable condition. Left untreated, a disorder or undesirable condition does not necessarily result in a further decrease in the subject's state of health.

The term "cancer" as used herein is defined as disease characterized by the rapid and uncontrolled growth of aberrant cells. The aberrant cells may form solid tumors or constitute a hematological malignancy. Cancer cells can spread locally or through the bloodstream and lymphatic system to other parts of the body. Examples of various cancers include, but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The term "subject," "patient" and "individual" are used interchangeably herein and are intended to include living organisms in which an immune response can be elicited (e.g., mammals). Examples of subjects include humans, primates, cows, horses, sheep, dogs, cats, mice, rats, rabbits, guinea pigs, pigs, and transgenic species thereof "Adoptive cellular immunotherapy" or "adoptive immunotherapy" refers to the administration of naturally occurring or genetically engineered disease antigen-specific immune cells (e.g., T cells). Adoptive cellular immunotherapy may be autologous (immune cells are from the recipient), allogeneic (immune cells are from a donor of the same species) or syngeneic (immune cells are from a donor genetically identical to the recipient).

"Autologous" refers to any material (e.g., a graft of organ, tissue, cells) derived from the same subject to which it is later to be re-introduced.

"Allogeneic" refers to a graft derived from a different subject of the same species.

A "therapeutically effective amount" or "effective amount" of a chimeric protein or cell expressing a chimeric protein of this disclosure (e.g., a chimeric Tim4 receptor or a cell expressing a chimeric Tim4 receptor) refers to that amount of protein or cells sufficient to result in amelioration of one or more symptoms of the disease, disorder, or undesired condition being treated. When referring to an individual active ingredient or a cell expressing a single active ingredient, administered alone, a therapeutically effective dose refers to the effects of that ingredient or cell expressing that ingredient alone. When referring to a combination, a therapeutically effective dose refers to the combined amounts of active ingredients or combined adjunctive active ingredient with a cell expressing an active ingredient that results in a therapeutic effect, whether administered serially or simultaneously.

"Treat" or "treatment" or "ameliorate" refers to medical management of a disease, disorder, or undesired condition of a subject. In general, an appropriate dose or treatment regimen comprising a host cell expressing a chimeric protein of this disclosure is administered in an amount sufficient to elicit a therapeutic or prophylactic benefit. Therapeutic or prophylactic/preventive benefit includes improved clinical outcome; lessening or alleviation of symptoms associated with a disease, disorder, or undesired condition; decreased occurrence of symptoms; improved quality of life; longer disease-free status; diminishment of extent of disease, disorder, or undesired condition; stabilization of disease state; delay of disease progression; remission; survival; prolonged survival; or any combination thereof.

The term "anti-tumor effect" refers to a biological effect which can be manifested by a decrease in tumor volume, a decrease in the number of tumor cells, a decrease in the number of metastases, an increase in life expectancy, or amelioration of various physiological symptoms associated with a cancerous condition. An "anti-tumor effect" can also be manifested by prevention of a hematological malignancy or tumor formation.

"Autoimmune disease" refers to a disorder that results from an autoimmune response. An autoimmune disease is the result of an inappropriately excessive response to a self-antigen. An autoimmune response may involve self-reactive B-cells that produce autoantibodies, self-reactive T-cells, or both. An "autoantibody" as used herein is an antibody produced by a subject that binds to a self-antigen also produced by the subject.

Additional definitions are provided throughout the present disclosure.

Chimeric Tim4 Receptors

In one aspect, the present disclosure provides a chimeric Tim4 receptor comprising a single chain chimeric protein, the single chain chimeric protein comprising: an extracellular domain comprising a Tim4 binding domain; an intracellular signaling domain comprising a first costimulatory signaling domain; and a transmembrane domain positioned between and connecting the extracellular domain and intracellular signaling domain. In certain embodiments, the extracellular domain of the chimeric Tim4 receptors described herein optionally includes an extracellular spacer domain positioned between and connecting the binding domain and transmembrane domain. When expressed in a host cell, chimeric Tim4 receptors of the present disclosure can confer a phosphatidylserine-specific, cytotoxic phenotype to the modified host cell (e.g., the host cell becomes cytotoxic to a stressed, damaged, injured, apoptotic, or necrotic cell expressing phosphatidylserine on its surface). In certain embodiments, the chimeric Tim4 receptors induce apoptosis in targeted cells via release of granzymes, perforin, granulysin, or any combination thereof. In further embodiments, cells expressing a chimeric Tim4 receptor according to the present description exhibit an engulfment phenotype specific to phosphatidylserine presenting cells.

The intracellular signaling domain can include one or more effector (also referred to as "costimulatory signaling") domains that costimulate the modified host cell. Signaling by the costimulatory signaling domain(s) is triggered by binding of the extracellular domain to phosphatidylserine. In certain embodiments, the intracellular signaling domain comprises a first costimulatory signaling domain. In further embodiments, the intracellular signaling domain comprises a first costimulatory signaling domain and a second costimulatory signaling domain. Chimeric Tim4 receptors according to the present disclosure can be used in a variety of therapeutic methods where clearance of apoptotic, necrotic, damaged, or stressed cells is beneficial, while providing costimulation that enhances cellular immune response, reduces immune cell exhaustion, or both.

Component parts of the fusion proteins of the present disclosure are further described in detail herein.

Extracellular Domain

As described herein, a chimeric Tim4 receptor comprises an extracellular domain comprising a Tim4 binding domain. The Tim4 binding domain confers specificity to phosphatidylserine (PtdSer), which is a phospholipid with a negatively charged head-group and a component of the cell membrane. In healthy cells, phosphatidylserine is preferentially found in the inner leaflet of the cell membrane. However, when cells are stressed, damaged or undergo apoptosis or necrosis, phosphatidylserine is exposed on the outer leaflet of the cell membrane. Thus, phosphatidylserine may be used as a marker to distinguish stressed, damaged, apoptotic, necrotic, pyroptotic, or oncotic cells. Binding of phosphatidylserine by the Tim4 binding domain may block the interaction between the phosphatidylserine and another molecule and, for example, interfere with, reduce or eliminate certain functions of the phosphatidylserine (e.g., signal transduction). In some embodiments, the binding of a phosphatidylserine may induce certain biological pathways or identify the phosphatidylserine molecule or a cell expressing phosphatidylserine for elimination.

A Tim4 binding domain suitable for use in a chimeric Tim4 receptor of the present disclosure may be any polypeptide or peptide derived from a Tim4 molecule that specifically binds phosphatidylserine. In certain embodiments, the Tim4 binding domain is derived from human Tim4. An exemplary human Tim4 molecule is provided in Uniprot. Ref. Q96H15 (SEQ ID NO:1). An exemplary human Tim4 binding domain comprises or consists of an amino acid sequence of SEQ ID NO:2 or amino acids 25-314 of SEQ ID NO:2. An exemplary mouse Tim4 binding domain comprises or consists of an amino acid sequence of SEQ ID NO:60 or amino acids 23-279 of SEQ ID NO:60. In certain embodiments, the Tim4 binding domain comprises or consists of an amino acid sequence having at least about 75%, 80%, 85%, 90%, 91%, 92%, 93%, 94%, 95%, 96%, 97%, 98%, 99%, 99.5%, or 100% identity to SEQ ID NO:2 or amino acids 25-314 of SEQ ID NO:2, or SEQ ID NO:60 or amino acids 23-279 of SEQ ID NO:60. In certain embodiments, the Tim4 binding domain comprises an amino acid sequence having at least about 1, 2, 3, 4, 5, 6, 7, 8, 9, 10, 11, 12, 13, 14, 15, 16, 17, 18, 19, or 20 amino acid modifications (e.g., deletions, additions, substitutions) to an amino acid sequence of SEQ ID NO:2 or amino acids 25-314 of SEQ ID NO:2, or SEQ ID NO:60 or amino acids 23-279 of SEQ ID NO:60.

In certain embodiments, the extracellular domain optionally comprises an extracellular, non-signaling spacer or linker domain. Where included, such a spacer or linker domain may position the binding domain away from the host cell surface to further enable proper cell/cell contact, binding, and activation. When included in a chimeric receptor as described herein, an extracellular spacer domain is generally located between the extracellular binding domain and the transmembrane domain of the chimeric Tim4 receptor. The length of the extracellular spacer may be varied to optimize target molecule binding based on the selected target molecule, selected binding epitope, binding domain size and affinity (see, e.g., Guest et al., J. Immunother. 28:203-11, 2005; PCT Publication No. WO 2014/031687). In certain embodiments, an extracellular spacer domain is an immunoglobulin hinge region (e.g., IgG1, IgG2, IgG3, IgG4, IgA, IgD). An immunoglobulin hinge region may be a wild type immunoglobulin hinge region or an altered wild type immunoglobulin hinge region. An altered $IgG_4$ hinge region is described in PCT Publication No. WO 2014/031687, which hinge region is incorporated herein by reference in its entirety. In a particular embodiment, an extracellular spacer domain comprises a modified $IgG_4$ hinge region having an amino acid sequence of ESKYGPPCPPCP (SEQ ID NO:3). Other examples of hinge regions that may be used in the chimeric Tim4 receptors described herein include the hinge region from the extracellular regions of type 1 membrane proteins, such as CD8a, CD4, CD28 and CD7, which may be wild-type or variants thereof. In further embodiments, an extracellular spacer domain comprises all or a portion of an immunoglobulin Fc domain selected from: a CH1 domain, a CH2 domain, a CH3 domain, or combinations thereof (see, e.g., PCT Publication WO2014/031687, which spacers are incorporated herein by reference in their entirety). In yet further embodiments, an extracellular spacer domain may comprise a stalk region of a type II C-lectin (the extracellular domain located between the C-type lectin domain and the transmembrane domain). Type II C-lectins include CD23, CD69, CD72, CD94, NKG2A, and NKG2D.

In certain embodiments, an extracellular domain comprises polynucleotide sequences derived from any mammalian species, including humans, primates, cows, horses, goats, sheep, dogs, cats, trice, rats, rabbits, guinea pigs, pigs, transgenic species thereof, or any combination thereof. In certain embodiments, an extracellular domain is murine, human, or chimeric.

Intracellular Signaling Domain

The intracellular signaling domain of a chimeric Tim4 receptor as described herein is an intracellular effector domain and is capable of transmitting functional signals to a cell in response to binding of the extracellular domain of the chimeric Tim4 receptor and phosphatidylserine. The signals transduced by the intracellular signaling domain promote effector function of the chimeric Tim4 receptor containing cell. Examples of effector function include cytotoxic activity, secretion of cytokines, proliferation, anti-apoptotic signaling, persistence, expansion, engulfment of a target cell or particle expressing phosphatidylserine on its surface, or any combination thereof.

In certain embodiments, an intracellular signaling domain comprises a costimulatory signaling domain. The costimulatory signaling domain may be any portion of a costimulatory signaling molecule that retains sufficient signaling activity. In some embodiments, a full length or full length intracellular component of a costimulatory signaling molecule is used. In some embodiments, a truncated portion of a costimulatory signaling molecule or intracellular component of a costimulatory signaling molecule is used, provided that the truncated portion retains sufficient signal transduction activity. In further embodiments, a costimulatory signaling domain is a variant of a whole or truncated portion of a costimulatory signaling molecule, provided that the variant retains sufficient signal transduction activity (i.e., is a functional variant).

In certain embodiments, the costimulatory signaling domain comprises a CD27, CD28, CD40L, GITR, NKG2C, CARD1, CD2, CD7, CD27, CD30, CD40, CD54 (ICAM), CD83, CD134 (OX-40), CD137 (4-1BB), CD150 (SLAMF1), CD152 (CTLA4), CD223 (LAG3), CD226, CD270 (HVEM), PD-1, CD273 (PD-L2), CD274 (PD-L1), B7-H3 (CD276), ICOS (CD278), DAP10, LAT, LFA-1 (CD11a/CD18), LIGHT, NKG2C, SLP76, TRIM, or ZAP70 signaling domain. In particular embodiments, the costimulatory signaling domain comprises an OX40, CD2, CD27, CD28, ICAM-1, LFA-1 (CD11a/CD18), ICOS (CD278), or 4-1BB (CD137) signaling domain. An exemplary CD28 costimulatory signaling domain comprises or consists of an amino acid sequence of SEQ ID NO:4 or 62. An exemplary OX40 costimulatory signaling domain comprises or consists of an amino acid sequence of SEQ ID NO:5. An exemplary CD2 costimulatory signaling domain comprises or consists of an amino acid sequence of SEQ ID NO:6. An exemplary 4-1BB costimulatory signaling domain comprises or consists of an amino acid sequence of SEQ ID NO:7. An exemplary CD27 costimulatory signaling domain comprises or consists of an amino acid sequence of SEQ ID NO:8. An exemplary ICAM-1 costimulatory signaling domain comprises or consists of an amino acid sequence of SEQ ID NO:9. An exemplary LFA-1 costimulatory signaling domain comprises or consists of an amino acid sequence of SEQ ID NO:10. An exemplary ICOS costimulatory signaling domain comprises or consists of an amino acid sequence of SEQ ID NO:11. An exemplary CD30 costimulatory signaling domain comprises or consists of an amino acid sequence of SEQ ID NO:12. An exemplary CD40 costimulatory signaling domain comprises or consists of an amino acid sequence of SEQ ID NO:13. An exemplary PD-1 costimulatory signaling domain comprises or consists of an amino acid sequence of SEQ ID NO:14. An exemplary CD7 costimulatory signaling domain comprises or consists of an amino acid sequence of SEQ ID NO:15. An exemplary LIGHT costimulatory signaling domain comprises or consists of an amino acid sequence of SEQ ID NO:16. An exemplary NKG2C costimulatory signaling domain comprises or consists of an amino acid sequence of SEQ ID NO:17. An exemplary B7-H3 costimulatory signaling domain comprises or consists of an amino acid sequence of SEQ ID NO:18. In certain embodiments, the costimulatory signaling domain comprises or consists of an amino acid sequence having at least about 75%, 80%, 85%, 90%, 91%, 92%, 93%, 94%, 95%, 96%, 97%, 98%, 99%, 99.5%, or 100% identity to any one of SEQ ID NOS:4-18 and 62. In certain embodiments, the costimulatory signaling domain comprises an amino acid sequence having at least about 1, 2, 3, 4, 5, 6, 7, 8, 9, 10, 11, 12, 13, 14, 15, 16, 17, 18, 19, or 20 amino acid modifications (e.g., deletions, additions, substitutions) to an amino acid sequence of any one of SEQ ID NOS:4-18 and 62. In certain embodiments, the intracellular signaling comprises a second costimulatory signaling domain. In preferred embodiments, the first costimulatory signaling domain and second costimulatory signaling domain are different.

In certain embodiments, the intracellular signaling domain further comprises an ITAM-containing activating domain. The ITAM-containing activating domain may recapitulate TCR signaling independently of endogenous TCR complexes. In certain embodiments, signaling via the ITAM-containing activating domain leads to mediation of a T cell response, including, but not limited to, proliferation, activation, differentiation, and the like. The ITAM-containing activating domain may be any portion of an ITAM-containing activating domain molecule that retains sufficient signaling activity. In some embodiments, a full length or full length intracellular component of an ITAM-containing activating domain molecule is used. In some embodiments, a truncated portion of an ITAM-containing activating domain molecule or intracellular component of an ITAM-containing activating domain molecule is used, provided that the truncated portion retains sufficient signal transduction activity. In further embodiments, an ITAM-containing activating domain is a variant of a whole or truncated portion of an ITAM-containing activating domain molecule, provided that the variant retains sufficient signal transduction activity (i.e., is a functional variant).

Examples of ITAM-containing activating domains that may be used in the chimeric Tim4 receptors of the present disclosure include those derived from CD3ζ, CD3γ, CD3δ, CD3ε, CD5, CD22, CD79a, CD278 (ICOS), DAP10, and CD66d. In specific embodiments, the ITAM-containing activating domain is a CD3ζ signaling domain. An exemplary CD3ζ signaling domain comprises or consists of an amino acid sequence of SEQ ID NO:63 or 19. An exemplary CD3γ signaling domain comprises or consists of an amino acid sequence of SEQ ID NO:20. An exemplary CD3δ signaling domain comprises or consists of an amino acid sequence of SEQ ID NO:21. An exemplary CD3ε signaling domain comprises or consists of an amino acid sequence of SEQ ID NO:22. An exemplary CD5 signaling domain comprises or consists of an amino acid sequence of SEQ ID NO:23. An exemplary CD22 signaling domain comprises or consists of an amino acid sequence of SEQ ID NO:24. An exemplary CD79a signaling domain comprises or consists of an amino acid sequence of SEQ ID NO:25. An exemplary DAP10 signaling domain comprises or consists of an amino acid sequence of SEQ ID NO:26. An exemplary CD66d signaling domain comprises or consists of an amino acid sequence of SEQ ID NO:27. In certain embodiments, the ITAM-containing activating domain comprises or consists of an amino acid sequence having at least about 75%, 80%, 85%, 90%, 91%, 92%, 93%, 94%, 95%, 96%, 97%, 98%, 99%, 99.5%, or 100% identity to any one of SEQ ID NOS:63 and 19-27. In certain embodiments, the CD3ζ signaling domain comprises an amino acid sequence having at least about 1, 2, 3, 4, 5, 6, 7, 8, 9, 10, 11, 12, 13, 14, 15, 16, 17, 18, 19, or 20 amino acid modifications (e.g., deletions, additions, substitutions) of an amino acid sequence to any one of SEQ ID NOS:19-27 and 63.

In another embodiment, an intracellular signaling domain comprises a CD28 costimulatory signaling domain and a CD3ζ signaling domain. In another embodiment, an intracellular signaling domain comprises a 4-1BB costimulatory signaling domain and a CD3ζ signaling domain. In yet another embodiment, an intracellular signaling domain comprises a CD27 costimulatory signaling domain and a CD3ζ signaling domain. In another embodiment, an intracellular signaling domain comprises a ICOS costimulatory signaling domain and a CD3ζ signaling domain. In another embodiment, an intracellular signaling domain comprises a LFA-1 costimulatory signaling domain and a CD3ζ signaling domain. In another embodiment, an intracellular signaling domain comprises an OX40 costimulatory signaling domain and a CD3ζ signaling domain. In yet another embodiment, an intracellular signaling domain comprises a CD2 costimulatory signaling domain and a CD3ζ signaling domain. In still another embodiment, an intracellular signaling domain comprises an ICAM-1 costimulatory signaling domain and a CD3ζ signaling domain.

Intracellular signaling domains may be derived from a mammalian species, including humans, primates, cows, horses, goats, sheep, dogs, cats, mice, rats, rabbits, guinea pigs, pigs, and transgenic species thereof.

Transmembrane Domain

The transmembrane domain of a chimeric Tim4 receptor connects and is positioned between the extracellular domain and the intracellular signaling domain. The transmembrane domain is a hydrophobic alpha helix that transverses the host cell membrane. The transmembrane domain may be directly fused to the binding domain or to the extracellular spacer domain if present. In certain embodiments, the transmembrane domain is derived from an integral membrane protein (e.g., receptor, cluster of differentiation (CD) molecule, enzyme, transporter, cell adhesion molecule, or the like). In one embodiment, the transmembrane domain is selected from the same molecule as the molecule from which the extracellular domain is derived. In another embodiment, the transmembrane domain is selected from the same molecule as the molecule from which the intracellular signaling domain is derived. For example, a chimeric Tim4 receptor may comprise a Tim4 binding domain and a Tim4 transmembrane domain. In another example, a chimeric Tim4 receptor may comprise a CD28 transmembrane domain and a CD28 costimulatory signaling domain. In certain embodiments, the transmembrane domain and the extracellular domain are derived from different molecules; the transmembrane domain and the intracellular signaling domain are derived from different molecules; or the transmembrane domain, extracellular domain, and intracellular signaling domain are all derived from different molecules. Examples of transmembrane domains that may be used in chimeric Tim4 receptors of the present disclosure include transmembrane domains from Tim4, CD3ζ, CD3γ, CD3δ, CD3ε, CD28, CD45, CD4, CD5, CD8, CD9, CD16, CD22, CD33, CD37, CD64, CD80, CD86, CD134, CD137, CD154, CD27, CD28, 4-1BB, OX40, CD30, CD40, PD-1, ICOS, LFA-1, CD2, CD7, LIGHT, NKG2C, and B7-H3. An exemplary Tim4 transmembrane domain comprises or consists of an amino acid sequence of SEQ ID NO:28 or 59. An exemplary CD28 transmembrane domain comprises or consists of an amino acid sequence of SEQ ID NO:29. An exemplary 4-1BB transmembrane domain comprises or consists of an amino acid sequence of SEQ ID NO:30. An exemplary OX40 transmembrane domain comprises or consists of an amino acid sequence of SEQ ID NO:31. An exemplary CD27 transmembrane domain comprises or consists of an amino acid sequence of SEQ ID NO:32. An exemplary ICOS transmembrane domain comprises or consists of an amino acid sequence of SEQ ID NO:33. An exemplary CD2 transmembrane domain comprises or consists of an amino acid sequence of SEQ ID NO:34. An exemplary LFA-1 transmembrane domain comprises or consists of an amino acid sequence of SEQ ID NO:35. An exemplary CD30 transmembrane domain comprises or consists of an amino acid sequence of SEQ ID NO:36. An exemplary CD40 transmembrane domain comprises or consists of an amino acid sequence of SEQ ID NO:37. An exemplary PD-1 transmembrane domain comprises or consists of an amino acid sequence of SEQ ID NO:38. An exemplary CD7 transmembrane domain comprises or consists of an amino acid sequence of SEQ ID NO:39. An exemplary LIGHT transmembrane domain comprises or consists of an amino acid sequence of SEQ ID NO:40. An exemplary NKG2C transmembrane domain comprises or consists of an amino acid sequence of SEQ ID NO:41. An exemplary B7-H3 transmembrane domain comprises or consists of an amino acid sequence of SEQ ID NO:42. In certain embodiments, the transmembrane domain comprises or consists of an amino acid sequence having at least about 75%, 80%, 85%, 90%, 91%, 92%, 93%, 94%, 95%, 96%, 97%, 98%, 99%, 99.5%, or 100% identity to any one of SEQ ID NOS:28-42, and 59. In certain embodiments, the transmembrane domain comprises an amino acid sequence having at least about 1, 2, 3, 4, 5, 6, 7, 8, 9, or 10 amino acid modifications (e.g., deletion, additions, substitutions) to an amino acid sequence of any one of SEQ ID NOS:28-42, and 59.

Transmembrane domains may derived from any mammalian species, including humans, primates, cows, horses, goats, sheep, dogs, cats, mice, rats, rabbits, guinea pigs, pigs; and transgenic species thereof.

In certain embodiments, a chimeric Tim4 receptor comprises polynucleotide sequences derived from any mammalian species, including humans, primates, cows, horses, goats, sheep, dogs, cats, mice, rats, rabbits, guinea pigs, pigs, transgenic species thereof, or any combination thereof. In certain embodiments, a chimeric Tim4 receptor is murine, chimeric, human, or humanized.

It is understood that direct fusion of one domain to another domain of a chimeric Tim4 receptor described herein does not preclude the presence of intervening junction amino acids. Junction amino acids may be natural or non-natural (e.g., resulting from the construct design of a chimeric protein). For example, junction amino acids may result from restriction enzyme sites used for joining one domain to another domain or cloning polynucleotides encoding chimeric Tim4 receptors into vectors.

Exemplary Chimeric Tim4 Receptors

The component parts of a chimeric Tim4 receptor as disclosed herein can be selected and arranged in various combinations to provide a desired specificity and effector phenotype to a host cell.

An exemplary chimeric Tim4 receptor of the present disclosure comprises an extracellular domain comprising a Tim4 binding domain; an intracellular signaling domain comprising a CD28 costimulatory signaling domain; and a CD28 transmembrane domain positioned between and connecting the extracellular domain and the intracellular signaling domain. In certain embodiments, the chimeric Tim4 receptor comprises or consists of an amino acid sequence of SEQ ID NO:43. In some embodiments, the chimeric Tim4 receptor comprises or consists of an amino acid sequence of amino acids 23-347 of SEQ ID NO:43.

Another exemplary chimeric Tim4 receptor of the present disclosure comprises an extracellular domain comprising a Tim4 binding domain; an intracellular signaling domain comprising a CD28 costimulatory signaling domain; and a Tim4 transmembrane domain positioned between and connecting the extracellular domain and the intracellular signaling domain. In certain embodiments, the chimeric Tim4 receptor comprises or consists of an amino acid sequence of SEQ ID NO:44. In some embodiments, the chimeric Tim4 receptor comprises or consists of an amino acid sequence of amino acids 23-341 of SEQ ID NO:44.

Another exemplary chimeric Tim4 receptor of the present disclosure comprises an extracellular domain comprising a Tim4 binding domain; an intracellular signaling domain comprising a 4-1BB costimulatory signaling domain; and a Tim4 transmembrane domain positioned between and connecting the extracellular domain and the intracellular signaling domain.

Another exemplary chimeric Tim4 receptor of the present disclosure comprises an extracellular domain comprising a Tim4 binding domain; an intracellular signaling domain comprising a 4-1BB costimulatory signaling domain; and a 4-1BB transmembrane domain positioned between and connecting the extracellular domain and the intracellular signaling domain.

Another exemplary chimeric Tim4 receptor of the present disclosure comprises an extracellular domain comprising a Tim4 binding domain; an intracellular signaling domain comprising a CD28 costimulatory signaling domain and a CD3ζ ITAM-containing activating domain; and a Tim4 transmembrane domain positioned between and connecting the extracellular domain and the intracellular signaling domain.

Yet another exemplary chimeric Tim4 receptor of the present disclosure comprises an extracellular domain comprising a Tim4 binding domain; an intracellular signaling domain comprising a 4-1BB costimulatory signaling domain and a CD3ζ ITAM-containing activating domain; and a Tim4 transmembrane domain positioned between and connecting the extracellular domain and the intracellular signaling domain.

In certain embodiments, the chimeric Tim4 receptor comprises or consists of an amino acid sequence of SEQ ID NO:45. In some embodiments, the chimeric Tim4 receptor comprises or consists of an amino acid sequence of amino acids 23-454 of SEQ ID NO:45.

Polynucleotides, Vectors, and Host Cells

In certain aspects, the present disclosure provides nucleic acid molecules that encode any one or more of the chimeric Tim4 receptors described herein. A nucleic acid may refer to a single- or double-stranded DNA, cDNA, or RNA, and may include a positive and a negative strand of the nucleic acid which complement one another, including antisense DNA, cDNA, and RNA. A nucleic acid may be naturally occurring or synthetic forms of DNA or RNA. The nucleic acid sequences encoding a desired chimeric Tim4 receptor can be obtained or produced using recombinant methods known in the art using standard techniques, such as by screening libraries from cells expressing the desired sequence or a portion thereof, by deriving the sequence from a vector known to include the same, or by isolating the sequence or a portion thereof directly from cells or tissues containing the same as described in, for example, Sambrook et al. (1989 and 2001 editions; *Molecular Cloning: A Laboratory Manual*, Cold Spring Harbor Laboratory Press, NY) and Ausubel et al. (Current Protocols in Molecular Biology, 2003). Alternatively, the sequence of interest can be produced synthetically, rather than being cloned.

Polynucleotides encoding the chimeric Tim4 receptor compositions provided herein may be derived from any animal, such as humans, primates, cows, horses, sheep, dogs, cats, mice, rats, rabbits, guinea pigs, pigs, or a combination thereof. In certain embodiments, a polynucleotide encoding the chimeric Tim4 receptor is from the same animal species as the host cell into which the polynucleotide is inserted.

The polynucleotides encoding chimeric Tim4 receptors of the present disclosure may be operatively linked to expression control sequences. Expression control sequences may include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequences); sequences that enhance protein stability; and possibly sequences that enhance protein secretion.

In certain embodiments, a polynucleotide encoding a chimeric Tim4 receptor comprises a sequence encoding a signal peptide (also referred to as leader peptide or signal sequence) at the 5'-end for targeting of the precursor protein to the secretory pathway. The signal peptide is optionally cleaved from the N-terminus of the extracellular domain during cellular processing and localization of the chimeric Tim4 receptor to the host cell membrane. A polypeptide from which a signal peptide sequence has been cleaved or removed may also be called a mature polypeptide. Examples of signal peptides that may be used in the chimeric Tim4 receptors of the present disclosure include signal peptides derived from endogenous secreted proteins, including, e.g., GM-CSF (amino acid sequence of SEQ ID NO:46) or Tim4 (amino acid sequence of SEQ ID NO:47 or 61). In certain embodiments, a polynucleotide sequence encodes a mature chimeric Tim4 receptor polypeptide, or a polypeptide sequence comprises a mature chimeric Tim4 receptor polypeptide. It is understood by persons of skill in the art that for sequences disclosed herein that include a signal peptide sequence, the signal peptide sequence may be replaced with another signal peptide that is capable of trafficking the encoded protein to the extracellular membrane.

In certain embodiments, a chimeric Tim4 receptor encoding polynucleotide of the present disclosure is codon optimized for efficient expression in a target host cell comprising the polynucleotide (see, e.g, Scholten et al., *Clin. Immunol.* 119:135-145 (2006)). As used herein, a "codon optimized" polynucleotide comprises a heterologous polynucleotide having codons modified with silent mutations corresponding to the abundances of tRNA in a host cell of interest.

A single polynucleotide molecule may encode one, two, or more chimeric Tim4 receptors according to any of the embodiments disclosed herein. A polynucleotide encoding more than one gene may comprise a sequence (e.g., IRES, viral 2A peptide) disposed between each gene for multicistronic expression.

A polynucleotide encoding a desired chimeric Tim4 receptor can be inserted into an appropriate vector, e.g., a viral vector, non-viral plasmid vector, and non-viral vectors, such as lipid-based DNA vectors, modified mRNA (modRNA), self-amplifying mRNA, CELiD, and transposon-mediated gene transfer (PiggyBac, Sleeping Beauty), for introduction into a host cell of interest (e.g., an immune cell). Polynucleotides encoding a chimeric Tim4 receptor of the present disclosure can be cloned into any suitable vector, such as an expression vector, a replication vector, a probe generation vector, or a sequencing vector. In certain embodiments, a polynucleotide encoding the extracellular domain, a polynucleotide encoding the transmembrane domain, and a polynucleotide encoding the intracellular signaling domain are joined together into a single polynucleotide and then inserted into a vector. In other embodiments, a polynucleotide encoding the extracellular domain, a polynucleotide encoding the transmembrane domain, and a polynucleotide encoding the intracellular signaling domain may be inserted separately into a vector such that the expressed amino acid sequence produces a functional chimeric Tim4 receptor. A vector that encodes a chimeric Tim4 receptor is referred to herein as a "chimeric Tim4 receptor vector."

In certain embodiments, a vector comprises a polynucleotide encoding one chimeric Tim4 receptor. In certain embodiments, a vector comprises one polynucleotide encoding two or more chimeric Tim4 receptors. In certain embodiments, a single polynucleotide encoding two or more chimeric Tim4 receptors is cloned into a cloning site and expressed from a single promoter, with each chimeric Tim4 receptor sequence separated from each other by an internal ribosomal entry site (IRES), furin cleavage site, or viral 2A peptide to allow for co-expression of multiple genes from a single open reading frame (e.g., a multicistronic vector). In certain embodiments, a viral 2A peptide is a porcine teschovirus-1 (P2A), *Thosea asigna* virus (T2A), equine rhinitis A virus (E2A), foot-and-mouth disease virus (F2A), or variant thereof. An exemplary T2A peptide comprises an amino acid sequence of SEQ ID NO:48, 64, 65, or 66. An exemplary P2A peptide comprises an amino acid sequence of SEQ ID NO:49 or 67. An exemplary E2A peptide sequence comprises an amino acid sequence of SEQ ID NO:50. An exemplary F2A peptide sequence comprises an amino acid sequence of SEQ ID NO:51.

In certain embodiments, a vector comprises two or more polynucleotides, each polynucleotide encoding a chimeric Tim4 receptor. The two or more polynucleotides encoding chimeric Tim4 receptors may be cloned sequentially into a vector at different cloning sites, with each chimeric Tim4 receptor expressed under the regulation of different promoters. In certain embodiments, vectors that allow long-term integration of a transgene and propagation to daughter cells are utilized. Examples include viral vectors such as, adenovirus, adeno-associated virus, vaccinia virus, herpes viruses, cytomegalovirus, pox virus, or retroviral vectors, such as lentiviral vectors. Vectors derived from lentivirus can be used to achieve long-term gene transfer and have added advantages over vectors including the ability to transduce non-proliferating cells, such as hepatocytes, and low immunogenicity.

A vector that encodes a core virus is referred to herein as a "viral vector." There are a large number of available viral vectors suitable for use with the compositions of the instant disclosure, including those identified for human gene therapy applications (see Pfeifer and Verme, *Ann. Rev. Genomics Hum. Genet.* 2:177, 2001). Suitable viral vectors include vectors based on RNA viruses, such as retrovirus-derived vectors, e.g., Maloney murine leukemia virus (MLV)-derived vectors, and include more complex retrovirus-derived vectors, e.g., lentivirus-derived vectors. HIV-1-derived vectors belong to this category. Other examples include lentivirus vectors derived from HIV-2, FIV, equine infectious anemia virus, SIV, and Maedi-Visna virus (ovine lentivirus). Methods of using retroviral and lentiviral viral vectors and packaging cells for transducing mammalian host cells with viral particles containing chimeric receptor transgenes are known in the art and have been previous described, for example, in U.S. Pat. No. 8,119,772; Walchli et al., *PLoS One* 6:327930, 2011; Zhao et al., *J. Immunol.* 174:4415, 2005; Engels et al., *Hum. Gene Ther.* 14:1155, 2003; Frecha et al., *Mol. Ther.* 18:1748, 2010; Verhoeyen et al., *Methods Mol. Biol.* 506:97, 2009. Retroviral and lentiviral vector constructs and expression systems are also commercially available.

In certain embodiments, a viral vector is used to introduce a non-endogenous polynucleotide encoding a chimeric Tim4 receptor to a host cell. A viral vector may be a retroviral vector or a lentiviral vector. A viral vector may also include a nucleic acid sequence encoding a marker for transduction. Transduction markers for viral vectors are known in the art and include selection markers, which may confer drug resistance, or detectable markers, such as fluorescent markers or cell surface proteins that can be detected by methods such as flow cytometry. In particular embodiments, a viral vector further comprises a gene marker for transduction comprising a fluorescent protein (e.g., green, yellow), an extracellular domain of human CD2, or a truncated human EGFR (EGFRt or tEGFR; see Wang et al., *Blood* 118:1255, 2011). An exemplary tEGFR comprises an amino acid sequence of SEQ ID NO:52. When a viral vector genome comprises a plurality of genes to be expressed in a host cell as separate proteins from a single transcript, the viral vector may also comprise additional sequences between the two (or more) genes allowing for multicistronic expression. Examples of such sequences used in viral vectors include internal ribosome entry sites (IRES), furin cleavage sites, viral 2A peptides (e.g., T2A, P2A, E2A, F2A), or any combination thereof.

Other viral vectors also can be used for polynucleotide delivery including DNA viral vectors, including, for example adenovirus-based vectors and adeno-associated virus (AAV)-based vectors; vectors derived from herpes simplex viruses (HSVs), including amplicon vectors, replication-defective HSV and attenuated HSV (Krisky et al., *Gene Ther.* 5: 1517, 1998).

Other viral vectors recently developed for gene therapy uses can also be used with the compositions and methods of this disclosure. Such vectors include those derived from baculoviruses and α-viruses. (Jolly, D J. 1999. Emerging Viral Vectors. pp 209-40 in Friedmann T. ed. The Development of Human Gene Therapy. New York: Cold Spring Harbor Lab), or plasmid vectors (such as sleeping beauty or other transposon vectors).

In certain embodiments, a chimeric Tim4 receptor vector can be constructed to optimize spatial and temporal control. For example, a chimeric Tim4 receptor vector can include promoter elements to optimize spatial and temporal control. In some embodiments, a chimeric Tim4 receptor vector includes tissue specific promoters or enhancers that enable specific induction of a chimeric Tim4 receptor to an organ, a cell type (e.g., immune cell), or a pathologic microenvironment, such as a tumor or infected tissue. An "enhancer" is an additional promoter element that can function either cooperatively or independently to activate transcription. In certain embodiments, a chimeric Tim4 receptor vector includes a constitutive promoter. In certain embodiments, a chimeric Tim4 receptor vector includes an inducible promoter. In certain embodiments, a chimeric Tim4 receptor vector includes a tissue specific promoter.

In certain embodiments, a chimeric Tim4 receptor vector can include a gene encoding a homing receptor, such as CCR4 or CXCR4, to improve homing and antitumor activity in vivo.

Where temporal control is desired, a chimeric Tim4 receptor vector may include an element that allows for inducible depletion of transduced cells. For example, such a vector may include an inducible suicide gene. A suicide gene may be an apoptotic gene or a gene that confers sensitivity to an agent (e.g., a drug). Exemplary suicide genes include chemically inducible caspase 9 (iCASP9) (U.S. Patent Publication No. 2013/0071414), chemically inducible Fas, or Herpes simplex virus thymidine kinase (HSV-TK), which confers sensitivity to ganciclovir. In further embodiments, a chimeric Tim4 receptor vector can be designed to express a known cell surface antigen that, upon infusion of an associated antibody, enables depletion of transduced cells. Examples of cell surface antigens and their associated antibodies that may be used for depletion of transduced cells include CD20 and Rituximab, RQR8 (combined CD34 and CD20 epitopes, allowing CD34 selection and anti-CD20 deletion) and Rituximab, and EGFR and Cetuximab.

Inducible vector systems, such as the tetracycline (Tet)-On vector system which activates transgene expression with doxycycline (Heinz et al., Hum. Gene Ther. 2011, 22:166-76) may also be used for inducible chimeric Tim4 receptor expression. Inducible chimeric Tim4 receptor expression may be also accomplished via retention using a selective hook (RUSH) system based on streptavidin anchored to the membrane of the endoplasmic reticulum through a hook and a streptavidin binding protein introduced into the chimeric Tim4 receptor structure, where addition of biotin to the system leads to the release of the chimeric Tim4 receptor from the endoplasmic reticulum (Agaugue et al., 2015, Mol. Ther. 23 (Suppl. 1):588).

In certain embodiments, a chimeric Tim4 receptor modified host cell may also be modified to co-express one or more small GTPases. Rho GTPases, a family of small (~21 k Da) signaling G proteins and also a subfamily of the Ras superfamily, regulate actin cytoskeleton organization in various cell types and promote pseudopod extension and phagosome closure during phagocytosis (see, e.g., Castellano et al., 2000, J. Cell Sci. 113:2955-2961). Engulfment requires F-actin recruitment beneath tethered cells or particles, and F-actin rearrangement to allow membrane extension resulting in cell or particle internalization. RhoGTPases include RhoA, Rac1, Rac2, RhoG, and CDC42. Other small GTPases, such as Rap1, is involved in regulation of complement mediated phagocytosis. Co-expression of a small GTPase with the chimeric Tim4 receptor may promote target cell or particle internalization and/or phagosome formation by the host cell. In some embodiments, a recombinant nucleic acid molecule encoding a GTPase is encoded on a separate vector than the chimeric Tim4 receptor-containing vector. In other embodiments, a recombinant nucleic acid molecule encoding a GTPase is encoded on the same vector as the chimeric Tim4 receptor. The GTPase and chimeric Tim4 receptor may be expressed under the regulation of different promoters on the same vector (e.g., at different multiple cloning sites). Alternatively, the chimeric Tim4 receptor and GTPase may be expressed under the regulation of one promoter in a multicistronic vector. The polynucleotide sequence encoding the chimeric Tim4 receptor and the polynucleotide sequence encoding the small GTPase(s) may be separated from each other by an IRES or viral 2A peptide in a multicistronic vector. Exemplary 2A peptides include T2A (SEQ ID NO:48), P2A (SEQ ID NO:49), E2A (SEQ ID NO:50), F2A (SEQ ID NO:51). Examples of GTPases that may be co-expressed with a chimeric Tim4 receptor include Rac1, Rac2, Rab5 (also referred to as Rab5a), Rab7, Rap1, RhoA, RhoG, CDC42, or any combination thereof. In specific embodiments, the GTPase comprises or is a sequence that is at least 90%, at least 91%, at least 92%, at least 93%, at least 94%, at least 95%, at least 96%, at least 97%, at least 98%, at least 99%, at least 99.5%, or 100% identical to a Rac1 amino acid sequence of SEQ ID NO:53, a Rab5 amino acid sequence of SEQ ID NO:54, a Rab7 amino acid sequence of SEQ ID NO:55, a Rap1 amino acid sequence of SEQ ID NO:56, a RhoA amino acid sequence of SEQ ID NO:57, a CDC42 amino acid sequence of SEQ ID NO:58, or any combination thereof.

In certain embodiments, a chimeric Tim4 receptor modified host cell may also be modified to co-express a chimeric antigen receptor (CAR). Chimeric antigen receptors are recombinant receptors generally composed of an scFv binding domain derived from an antibody, a transmembrane domain, and an intracellular signaling domain(s) usually derived from a TCR. In certain embodiments, a CAR is a first generation CAR, a second generation CAR, or a third generation CAR. A first generation CAR generally has an intracellular signaling domain comprising an intracellular signaling domain of CD3ζ or FcγRI or other ITAM-containing activating domain to provide a T cell activation signal. Second generation CARs further comprise a costimulatory signaling domain (e.g., a costimulatory signaling domain from an endogenous T cell costimulatory receptor, such as CD28, 4-1BB, or ICOS). Third generation CARs comprise an ITAM-containing activating domain, a first costimulatory signaling domain and a second costimulatory signaling domain.

In certain embodiments, a chimeric Tim4 receptor modified host cell may also be modified to co-express a recombinant TCR. In one embodiment, a recombinant TCR is an enhanced affinity TCR.

In certain embodiments, a chimeric Tim4 receptor modified host cell may also be modified to co-express a single chain TCR (scTCR) fusion protein. A scTCR fusion protein comprises a binding domain comprising a scTCR (a TCR Vα domain linked to a TCR Vβ domain), an optional extracellular spacer, a transmembrane domain, and an intracellular component comprising a single intracellular signaling domain providing an T cell activation signal (e.g., a CD3ζ ITAM-containing activating domain) and optionally a costimulatory signaling domain (see, Aggen et al., 2012, Gene Ther. 19:365-374; Stone et al., Cancer Immunol. Immunother. 2014, 63:1163-76).

In certain embodiments, a chimeric Tim4 receptor modified host cell may also be modified to co-express a T cell receptor-based chimeric antigen receptor (TCR-CAR). A TCR-CAR is a heterodimeric fusion protein generally comprising a soluble TCR (a polypeptide chain comprising a Vα domain and Cα domain and a polypeptide chain comprising a Vβ domain and a Cβ domain) wherein the VβCβ polypeptide chain is linked to a transmembrane domain and an intracellular signaling component (e.g., an ITAM-containing activating domain and optionally a costimulatory signaling domain) (see, e.g., Walseng et al., 2017 Scientific Reports 7:10713).

In certain embodiments, a recombinant nucleic acid molecule encoding a cellular immunotherapy composition, e.g., CAR, TCR, scTCR fusion protein, or TCR-CAR, is encoded on a separate vector than the chimeric Tim4 receptor-containing vector within a host cell. In other embodiments, a recombinant nucleic acid molecule encoding a CAR, TCR, scTCR fusion protein, or TCR-CAR is encoded on the same vector as the chimeric Tim4 receptor within a host cell. The CAR, TCR, scTCR fusion protein, or TCR-CAR, and the chimeric Tim4 receptor may be expressed under the regulation of different promoters on the same vector (e.g., at different multiple cloning sites). Alternatively, the chimeric Tim4 receptor and CAR, TCR, scTCR fusion protein, or TCR-CAR may be expressed under the regulation of one promoter in a multicistronic vector. The polynucleotide sequence encoding the chimeric Tim4 receptor and the polynucleotide sequence encoding the CAR, TCR, scTCR fusion protein, or TCR-CAR may be separated by an IRES or viral 2A peptide in a multicistronic vector.

In certain embodiments, a cell, such as an immune cell, obtained from a subject may be genetically modified into a non-natural or recombinant cell (e.g., a non-natural or recombinant immune cell) by introducing a polynucleotide that encodes a chimeric Tim4 receptor as described herein, whereby the cell expresses a cell surface localized chimeric Tim4 receptor. In certain embodiments, a host cell is an immune cell, such as a myeloid progenitor cell or a lymphoid progenitor cell. Exemplary immune cells that may be modified to comprise a polynucleotide encoding a chimeric Tim4 receptor or a vector comprising a polynucleotide encoding a chimeric Tim4 receptor include a T cell, a natural killer cell, a B cell, a lymphoid precursor cell, an antigen presenting cell, a dendritic cell, a Langerhans cell, a myeloid precursor cell, a mature myeloid cell, a monocyte, or a macrophage.

In certain embodiments, a B cell is genetically modified to express one or more chimeric Tim4 receptors. B cells possess certain properties that may be advantageous as host cells, including: trafficking to sites of inflammation, capable of internalizing and presenting antigen, capable of costimulating T cells, highly proliferative, and self-renewing (persist for life). In certain embodiments, a chimeric Tim4 receptor modified B cell is capable of digesting an engulfed target cell or engulfed target particle into smaller peptides and presenting them to T cells via an MEW molecule. Antigen presentation by a chimeric Tim4 receptor modified B cell may contribute to antigen spreading of the immune response to non-targeted antigens. B cells include progenitor or precursor cells committed to the B cell lineage (e.g., pre-pro-B cells, pro-B cells, and pre-B cells); immature and inactivated B cells; or mature and functional or activated B cells. In certain embodiments, B cells may be naïve B cells, plasma cells, regulatory B cells, marginal zone B cells, follicular B cells, lymphoplasmacytoid cell, plasmablast cell, memory B cells, or any combination thereof. Memory B cells may be distinguished from naïve B cells by expression of CD27, which is absent on naïve B cells. In certain embodiments, the B cells can be primary cells or cell lines derived from human, mouse, rat, or other mammals. B cell lines are well known in the art. If obtained from a mammal, a B cell can be obtained from numerous sources, including blood, bone marrow, spleen, lymph node, or other tissues or fluids. A B cell composition may be enriched or purified.

In certain embodiments, a T cell is genetically modified to express one or more chimeric Tim4 receptors. Exemplary T cells include $CD4^+$ helper, $CD8^+$ effector (cytotoxic), naïve (CD45 RA+, CCR7+, CD62L+, CD27+, CD45RO−), central memory ($CD45RO^+$, $CD62L^+$, $CD8^+$), effector memory (CD45RA+, CD45RO−, CCR7−, CD62L−, CD27−), T memory stem, regulatory, mucosal-associated invariant (MAIT), γδ (gd), tissue resident T cells, natural killer T cells, or any combination thereof. In certain embodiments, the T cells can be primary cells or cell lines derived from human, mouse, rat, or other mammals. If obtained from a mammal, a T cell can be obtained from numerous sources, including blood, bone marrow, lymph node, thymus, or other tissues or fluids. A T cell composition may be enriched or purified. T cell lines are well known in the art, some of which are described in Sandberg et al., *Leukemia* 21:230, 2000. In certain embodiments, the T cells lack endogenous expression of a TCRα gene, TCRβ gene, or both. Such T cells may naturally lack endogenous expression of TCRα and β chains, or may have been modified to block expression (e.g., T cells from a transgenic mouse that does not express TCR α and β chains or cells that have been manipulated to inhibit expression of TCR α and β chains) or to knockout a TCRα chain, a TCRβ chain, or both genes.

In certain embodiments, host cells expressing a chimeric Tim4 protein of this disclosure on the cell surface are not T cells or cells of a T cell lineage, but cells that are progenitor cells, stem cells or cells that have been modified to express cell surface anti-CD3.

In certain embodiments, gene editing methods are used to modify the host cell genome to comprise a polynucleotide encoding a chimeric Tim4 receptor of the present disclosure. Gene editing, or genome editing, is a method of genetic engineering wherein DNA is inserted, replaced, or removed from a host cell's genome using genetically engineered endonucleases. The nucleases create specific double-stranded breaks at targeted loci in the genome. The host cell's endogenous DNA repair pathways then repair the induced break(s), e.g., by non-homologous ending joining (NHEJ) and homologous recombination. Exemplary endonucleases useful for gene editing include a zinc finger nuclease (ZFN), a transcription activator-like effector (TALE) nuclease, a clustered regularly interspaced short palindromic repeats (CRISPR)/Cas nuclease system (e.g., CRISPR-Cas9), a meganuclease, or combinations thereof. Methods of disrupting or knocking out genes or gene expression in immune cells including B cells and T cells, using gene editing endonucleases are known in the art and described, for example, in PCT Publication Nos. WO 2015/066262; WO 2013/074916; WO 2014/059173; Cheong et al., Nat. Comm. 2016 7:10934; Chu et al., Proc. Natl. Acad. Sci. USA 2016 113:12514-12519; methods from each of which are incorporated herein by reference in their entirety.

In certain embodiments, expression of an endogenous gene of the host cell is inhibited, knocked down, or knocked out. Examples of endogenous genes that may be inhibited, knocked down, or knocked out in a B cell include IGH, IGκ, IGλ, or any combination thereof. Examples of endogenous genes that may be inhibited, knocked down, or knocked out in a T cell include a TCR gene (TRA or TRB), an HLA gene (HLA class I gene or HLA class II gene), an immune checkpoint molecule (PD-L1, PD-L2, CD80, CD86, B7-H3, B7-H4, HVEM, adenosine, GALS, VISTA, CEACAM-1, CEACAM-3, CEACAM-5, PVRL2, PD-1, CTLA-4, BTLA, KIR, LAG3, TIM3, A2aR, CD244/2B4, CD160, TIGIT, LAIR-1, or PVRIG/CD112R), or any combination thereof. Expression of an endogenous gene may be inhibited, knocked down, or knocked out at the gene level, transcriptional level, translational level, or a combination thereof. Methods of inhibiting, knocking down, or knocking out an endogenous gene may be accomplished, for example, by an RNA interference agent (e.g., siRNA, shRNA, miRNA, etc.) or an engineered endonuclease (e.g., CRISPR/Cas nuclease system, a zinc nuclease (ZFN), a Transcription Activator Like Effector nuclease (TALEN), a meganuclease), or any combination thereof. In certain embodiments, an endogenous B cell gene (e.g., IGH, IGκ, or IGλ) is knocked out by insertion of a polynucleotide encoding a chimeric Tim4 receptor of the present disclosure into the locus of the endogenous B cell gene, such as via an engineered endonuclease. In certain embodiments, an endogenous T cell gene (e.g., a TCR gene, an HLA gene, or an immune checkpoint molecule gene) is knocked out by insertion of a polynucleotide encoding a chimeric Tim4 receptor of the present disclosure into the locus of the endogenous T cell gene, such as via an engineered endonuclease.

In certain embodiments, a host cell may be genetically modified to express one type of chimeric Tim4 receptor. In other embodiments, a host cell may express at least two or more different chimeric Tim4 receptors.

The present disclosure also provides a composition comprising a population of chimeric Tim4 receptor modified host cells. In certain embodiments, the population of chimeric Tim4 receptor modified host cells may be a population of B cells, a population of T cells, a population of natural killer cells, a population of lymphoid precursor cells, a population of antigen presenting cells, a population of dendritic cells, a population of Langerhans cells, a population of myeloid precursor cells, a population of mature myeloid cells, or any combination thereof. Furthermore, a population of chimeric Tim4 receptor modified host cells of a particular cell type may be composed of one or more subtypes. For example, a population of B cells may be composed of chimeric Tim4 receptor modified naïve B cells, plasma cells, regulatory B cells, marginal zone B cells, follicular B cells, lymphoplasmacytoid cells, plasmablast cells, memory B cells, or any combination thereof. In another example, a population of T cells may be composed of chimeric Tim4 receptor modified CD4$^+$ helper T cells, CD8$^+$ effector (cytotoxic) T cells, naïve (CD45 RA+, CCR7+, CD62L+, CD27+, CD45RO−) T cells, central memory (CD45RO$^+$, CD62L$^+$, CD8$^+$) T cells, effector memory (CD45RA+, CD45RO−, CCR7−, CD62L−, CD27−) T cells, T memory stem cells, regulatory T cells, mucosal-associated invariant T cells (MAIT), γδ (gd) cells, tissue resident T cells, natural killer T cells, or any combination thereof.

In certain embodiments, a population of host cells is composed of cells that each expresses the same chimeric Tim4 receptor(s). In other embodiments, a population of host cells is composed of a mixture of two or more subpopulation of host cells, wherein each subpopulation expresses a different chimeric Tim4 receptor or set of chimeric Tim4 receptors.

In certain embodiments, when preparing chimeric Tim4 receptor modified host cells, e.g., B cells or T cells, one or more growth factor cytokines that promotes proliferation of the host cells, e.g., B cells or T cells, may be added to the cell culture. The cytokines may be human or non-human. Exemplary growth factor cytokines that may be used to promote T cell proliferation include IL-2, IL-15, or the like. Exemplary growth factor cytokines that may be used to promote B cell proliferation include CD40L, IL-2, IL-4, IL-15, IL-21, BAFF, or the like.

Prior to genetic modification of the host cells with a chimeric Tim4 receptor vector, a source of host cells (e.g., T cells, B cells, natural killer cells, etc.) is obtained from a subject (e.g., whole blood, peripheral blood mononuclear cells, bone marrow, lymph node tissue, cord blood, thymus tissue, tissue from a site of infection, ascites, pleural effusion, spleen tissue), from which host cells are isolated using methods known in the art. Specific host cell subsets can be collected in accordance with known techniques and enriched or depleted by known techniques, such as affinity binding to antibodies, flow cytometry and/or immunomagnetic selection. After enrichment and/or depletion steps and introduction of a chimeric Tim4 receptor, in vitro expansion of the desired modified host cells can be carried out in accordance with known techniques, or variations thereof that will be apparent those skilled in the art.

Chimeric Tim4 receptors of the present disclosure confer cytotoxic activity to host cells expressing the chimeric Tim4 receptors that is specific for phosphatidylserine. Thus, upon binding phosphatidylserine exposed on the surface of a target cell, a host cell expressing a chimeric Tim4 receptor is capable of inducing apoptosis of the target cell. In certain embodiments, the host cell expressing the chimeric Tim4 receptor induces apoptosis of the target cell via: release of granzymes, perforins, granulysin, or any combination thereof; Fas ligand-Fas interaction; or both. In further embodiments, the chimeric Tim4 receptor further confers phosphatidylserine specific engulfment activity to host cells expressing the chimeric Tim4 receptor. In yet further embodiments, the host cell does not naturally exhibit an engulfment phenotype prior to modification with the chimeric Tim4 receptor.

Chimeric Tim4 receptors of the present disclosure may also be capable of costimulating T cells via at least one signaling pathway. In certain embodiments, chimeric Tim4 receptors provide costimulatory signals to T cells via at least two distinct signaling pathways (e.g., via the selected costimulatory signaling domain(s) in the chimeric Tim4 receptor and Tim1). For example, a chimeric Tim4 receptor comprising a CD28 costimulatory signaling domain may be capable of providing a costimulatory signal via CD28 and Tim1. In another example, a chimeric Tim4 receptor comprising a 4-1BB costimulatory signaling domain may be capable of providing a costimulatory signal via 4-1BB and Tim1. In yet another example, a chimeric Tim4 receptor comprising a 4-1BB costimulatory signaling domain and CD28 costimulatory signaling domain may be capable of providing a costimulatory signal via 4-1BB, CD28, and Tim1.

In certain embodiments, host immune cells expressing the chimeric Tim4 receptors exhibit reduction or inhibition of immune cell exhaustion. In certain embodiments, the host immune cell is a T cell or NK cells. In certain embodiments, exhausted T cells exhibit; (a) increased expression of PD-1, TIGIT, LAG3, TIM3, or any combination thereof; (b) decreased production of IFN-γ, IL-2, TNF-α, or any combination thereof; or both (a) and (b). In certain embodiments, exhausted NK cells exhibit; (a) increased expression of PD-1, NKG2A, TIM3, or any combination thereof; (b) decreased production of IFN-γ, TNF-α, or both; or both (a) and (b).

In certain embodiments, host cells expressing the chimeric Tim4 receptors exhibit an enhanced effector response (e.g., tumor specific). In certain embodiments, the effector response is enhanced T cell proliferation, cytokine production (e.g., IFN-γ, IL-2, TNF-α), cytotoxic activity, persistence, or any combination thereof. Host cells expressing chimeric Tim4 receptors may be administered to a subject alone, or in combination with other therapeutic agents, including for example CAR-T cells, TCRs, antibodies, radiation therapy, chemotherapies, small molecules, oncolytic viruses, electropulse therapy, etc.

In certain embodiments host cells expressing the chimeric Tim4 receptors exhibit a reduced immunosuppressive response to phosphatidylserine. Phosphatidylserine is one of the primary apoptotic cell ligands that signal "eat me" to phagocytes. The removal of apoptotic cells by phagocytes generally reduces or prevents an inflammatory response via secretion of anti-inflammatory cytokines IL-10 and TGF-β and the decrease of secretion of inflammatory cytokines TNF-α, IL-1β, and IL-12. Thus, phosphatidylserine may act as an immunosuppressive signal during the clearance of apoptotic cells. In certain embodiments, upon binding phosphatidylserine, a chimeric Tim4 receptor modified host cell exhibits increased antigen-specific cytokine production (e.g., IFN-γ, IL-2, TNF-α), thereby reducing the immunosuppressive response to phosphatidylserine.

The expression of chimeric Tim4 receptors on host cells may be functionally characterized according to any of a large number of art-accepted methodologies for assaying host cell (e.g., T cell) activity, including determination of T cell binding, activation or induction and also including determination of T cell responses that are antigen-specific. Examples include determination of T cell proliferation, T cell cytokine release, antigen-specific T cell stimulation, CTL activity (e.g., by detecting $^{51}$Cr or Europium release from pre-loaded target cells), changes in T cell phenotypic marker expression, and other measures of T cell functions. Procedures for performing these and similar assays are may be found, for example, in Lefkovits (*Immunology Methods Manual: The Comprehensive Sourcebook of Techniques*, 1998). See, also, *Current Protocols in Immunology*; Weir, *Handbook of Experimental Immunology*, Blackwell Scientific, Boston, MA (1986); Mishell and Shigii (eds.) *Selected Methods in Cellular Immunology*, Freeman Publishing, San Francisco, CA (1979); Green and Reed, *Science* 281:1309 (1998) and references cited therein. Cytokine levels may be determined according to methods known in the art, including for example, ELISA, ELISPOT, intracellular cytokine staining, flow cytometry, and any combination thereof (e.g., intracellular cytokine staining and flow cytometry). Immune cell proliferation and clonal expansion resulting from an antigen-specific elicitation or stimulation of an immune response may be determined by isolating lymphocytes, such as circulating lymphocytes in samples of peripheral blood cells or cells from lymph nodes, stimulating the cells with antigen, and measuring cytokine production, cell proliferation and/or cell viability, such as by incorporation of tritiated thymidine or non-radioactive assays, such as MTT assays and the like.

In certain embodiments, a chimeric Tim4 receptor modified host cell has a phagocytic index of about 20 to about 1,500 for a target cell. A "phagocytic index" is a measure of phagocytic activity of the transduced host cell as determined by counting the number of target cells or particles ingested per chimeric Tim4 receptor modified host cell during a set period of incubation of a suspension of target cells or particles and chimeric Tim4 receptor modified host cells in media. Phagocytic index may be calculated by multiplying [total number of engulfed target cells/total number of counted chimeric Tim4 receptor modified cells (e.g., phagocytic frequency)]×[average area of target cell or particle staining per chimeric Tim4 receptor⁺host cell×100 (e.g., hybrid capture)] or [total number of engulfed particles/total number of counted chimeric Tim4 receptor modified host cells]×[number of chimeric Tim4 receptor modified host cells containing engulfed particles/total number of counted chimeric Tim4 receptor cells]×100. In certain embodiments, a chimeric Tim4 receptor modified cell has a phagocytic index of about 30 to about 1,500; about 40 to about 1,500; about 50 to about 1,500; about 75 to about 1,500; about 100 to about 1,500; about 200 to about 1,500; about 300 to about 1,500; about 400 to about 1,500; about 500 to about 1,500; about 20 to about 1,400; about 30 to about 1,400; about 40 to about 1,400; about 50 to about 1,400; about 100 to about 1,400; about 200 to about 1,400; about 300 to about 1,400; about 400 to about 1,400; about 500 to about 1,400; about 20 to about 1,300; about 30 to about 1,300; about 40 to about 1,300; about 50 to about 1,300; about 100 to about 1,300; about 200 to about 1,300; about 300 to about 1,300; about 400 to about 1,300; about 500 to about 1,300; about 20 to about 1,200; about 30 to about 1,200; about 40 to about 1,200; about 50 to about 1,200; about 100 to about 1,200; about 200 to about 1,200; about 300 to about 1,200; about 400 to about 1,200; about 500 to about 1,200; about 20 to about 1,100; about 30 to about 1,100; about 40 to about 1,100; about 50 to about 1,100; about 100 to about 1,100; about 200 to about 1,100; about 300 to about 1,100; about 400 to about 1,100; or about 500 to about 1,100; about 20 to about 1,000; about 30 to about 1,000; about 40 to about 1,000; about 50 to about 1,000; about 100 to about 1,000; about 200 to about 1,000; about 300 to about 1,000; about 400 to about 1,000; or about 500 to about 1,000; about 20 to about 750; about 30 to about 750; about 40 to about 750; about 50 to about 750; about 100 to about 750; about 200 to about 750; about 300 to about 750; about 400 to about 750; or about 500 to about 750; about 20 to about 500; about 30 to about 500; about 40 to about 500; about 50 to about 500; about 100 to about 500; about 200 to about 500; or about 300 to about 500. In further embodiments, the incubation time is from about 2 hours to about 4 hours, about 2 hours, about 3 hours, or about 4 hours. In yet further embodiments, a chimeric Tim4 receptor modified cell exhibits phagocytic index that is statistically significantly higher than a cell transduced with truncated EGFR control. Phagocytic index may be calculated using methods known in the art and as further described in the Examples and PCT Application No. PCT/US2017/053553 (incorporated herein by reference in its entirety), including quantification by flow cytometry or fluorescence microscopy.

Host cells may be from an animal, such as a human, primate, cow, horse, sheep, dog, cat, mouse, rat, rabbit, guinea pig, pig, or a combination thereof. In a preferred embodiment, the animal is a human. Host cells may be obtained from a healthy subject or a subject having a disease associated with expression or overexpression of an antigen.

Methods of Use

In one aspect, the present disclosure provides methods for conferring or enhancing phosphatidylserine-specific cytotoxic activity of a cell comprising introducing into a host cell a nucleic acid molecule encoding at least one chimeric Tim4 receptor or a chimeric Tim4 receptor vector according to any of the embodiments described herein; and expressing the at least one chimeric Tim4 receptor in the host cell, wherein the at least one chimeric Tim4 receptor enhances the phosphatidylserine-specific cytotoxic activity of the host cell as compared to a the host cell prior to modification to express a chimeric Tim4 receptor. In certain embodiments, the cytotoxic activity of the host cell is increased at least about 10%, 15%, 20%, 25%, 30%, 35%, 40%, 50%, 55%, 60%, 65%, 70%, 75%, 80%, 85%, 90%, 95%, 100%, 110%, 120%, 130%, 140%, 150%, 160%, 170%, 180%, 190%, 200% or more as compared to the host cell prior to modification with a nucleic acid molecule encoding a chimeric Tim4 receptor or a chimeric Tim4 receptor vector. In some embodiments, the host cell is a T cell or an NK cell. Methods of measuring cytotoxic activity of host cells, particularly immune cells such as T cells and NK cells, include a chromium ($^{51}$Cr)-release assay, a β-gal or firefly luciferase release assay, flow cytometric methods of mediating target cell death and effector cell activity (see, e.g., Expert Rev. Vaccines, 2010, 9:601-616).

In certain embodiments, methods for conferring or enhancing phosphatidylserine-specific cytotoxic activity of a cell further comprise conferring or enhancing phosphatidylserine-specific engulfment activity of the host cell expressing the at least one chimeric Tim4 receptor. In certain such embodiments, the host cell does not naturally exhibit an engulfment phenotype prior to modification with the chimeric Tim4 receptor. For example in certain such embodiments, the engulfment activity of the host cell is increased at least about 10%, 15%, 20%, 25%, 30%, 35%, 40%, 50%, 55%, 60%, 65%, 70%, 75%, 80%, 85%, 90%, 95%, 100%, 110%, 120%, 130%, 140%, 150%, 160%, 170%, 180%, 190%, 200% or more as compared to the host cell prior to modification to express the chimeric Tim4 receptor vector. In certain embodiments, the host cell does not naturally possess engulfment activity. In some embodiments, the host cell is a T cell or an NK cell. Methods of measuring engulfment activity of host cells include methods as described in PCT/US2017/053553 (incorporated herein by reference in its entirety).

In another aspect, a chimeric Tim4 receptor, a polynucleotide encoding a chimeric Tim4 receptor, a chimeric Tim4 receptor vector, or a host cell that expresses a chimeric Tim4 receptor according to any of the embodiments provided herein may be used in a method of enhancing effector function of the host cell. In certain embodiments, enhanced effector function comprises increased cytotoxic activity, increased antigen specific cytokine production (e.g., IFN-γ, IL-2, TNF-α, or any combination thereof), increased anti-apoptotic signaling, increased persistence, increased expansion, increased proliferation, or any combination thereof. In certain embodiments, the effector function of the host cell is enhanced at least about 10%, 15%, 20%, 25%, 30%, 35%, 40%, 50%, 55%, 60%, 65%, 70%, 75%, 80%, 85%, 90%, 95%, 100%, 110%, 120%, 130%, 140%, 150%, 160%, 170%, 180%, 190%, 200% or more as compared to a host cell that is not modified with a nucleic acid molecule encoding a chimeric Tim4 receptor or a chimeric Tim4 receptor vector. In certain embodiments, the host cell is a T cell or an NK cell.

In another aspect, host cells modified with chimeric Tim4 receptors of the present disclosure can be used in methods for inhibiting or reducing immune cell exhaustion. In certain embodiments, reduced exhaustion in T cells comprises; (a) decreased expression of PD-1, TIGIT, LAG3, TIM3, or any combination thereof in T cells; (b) increased production of IFN-γ, IL-2, TNF-α, or any combination thereof in T cells; or both (a) and (b). In certain embodiments, reduced exhaustion in NK cells comprises; (a) decreased expression of PD-1, NKG2A, TIM3, or any combination thereof in NK cells; (b) increased production of IFN-γ, TNF-α, or both in NK cells; or both (a) and (b). In certain embodiments, the expression of an immune checkpoint molecule is decreased at least about 5%, 10%, 15%, 20%, 25%, 30%, 35%, 40%, 50%, 55%, 60%, 65%, 70%, 75%, 80%, 85%, 90%, 95%, or 100% in a host immune cell expressing the chimeric Tim4 receptor as compared to a host immune cell that is not modified with a nucleic acid molecule encoding a chimeric Tim4 receptor or a chimeric Tim4 receptor vector. In certain embodiments, the expression of the cytokine is increased at least about 5%, 10%, 15%, 20%, 25%, 30%, 35%, 40%, 50%, 55%, 60%, 65%, 70%, 75%, 80%, 85%, 90%, 95%, 100%, 110%, 120%, 130%, 140%, 150%, 160%, 170%, 180%, 190%, 200% or more in a host immune cell expressing the chimeric Tim4 receptor as compared to a host immune cell that is not modified with a nucleic acid molecule encoding a chimeric Tim4 receptor or a chimeric Tim4 receptor vector.

In another aspect, a chimeric Tim4 receptor, a polynucleotide encoding a chimeric Tim4 receptor, a chimeric Tim4 receptor vector, or a host cell that expresses a chimeric Tim4 receptor according to any of the embodiments provided herein may be used in a method of reducing an immunosuppressive response to phosphatidylserine in a host cell. In certain embodiments, the immunosuppressive response comprises secretion of anti-inflammatory cytokines (e.g., IL-10, TGF-β, or both), the decrease in secretion of inflammatory cytokines (e.g., TNF-α, IL-1β, and IL-12), or both. In certain embodiments, the immunosuppressive response of the host cell to phosphatidylserine is decreased at least about 5%, 10%, 15%, 20%, 25%, 30%, 35%, 40%, 50%, 55%, 60%, 65%, 70%, 75%, 80%, 85%, 90%, 95%, 100% as compared to a host cell that is not modified with a nucleic acid molecule encoding a chimeric Tim4 receptor or a chimeric Tim4 receptor vector. In certain embodiments, the host cell is a T cell or an NK cell.

In yet another aspect, a chimeric Tim4 receptor, a polynucleotide encoding a chimeric Tim4 receptor, a chimeric Tim4 receptor vector, or a host cell that expresses a chimeric Tim4 receptor according to any of the embodiments provided herein may be used in methods for eliminating target cells bearing surface exposed phosphatidylserine, e.g., for the elimination of cancer cells bearing surface presented phosphatidylserine. In certain embodiments, the target cells are damaged, stressed, apoptotic, necrotic cells (e.g., tumor cells) bearing surface exposed phosphatidylserine. In certain embodiments, host cells expressing chimeric Tim4 receptors clear damaged, stressed, apoptotic, or necrotic target cells bearing surface exposed phosphatidylserine via inducing apoptosis, or both inducing apoptosis and engulfment. Host cells expressing chimeric Tim4 receptors may be administered to a subject alone, or in combination with other therapeutic agents, including for example CAR-T cells, TCRs, antibodies, radiation therapy, chemotherapy, small molecules, oncolytic viruses, electropulse therapy, etc.

In another aspect, a chimeric Tim4 receptor, a polynucleotides encoding a chimeric Tim4 receptor, a chimeric Tim4 receptor vector, or a host cell that expresses a chimeric Tim4 receptor according to any of the embodiments provided herein may be used in methods to enhance the effect of a therapeutic agent that induces cellular stress, damage, necrosis, or apoptosis. Certain therapies, such as chemotherapy, radiation therapy, UV light therapy, electropulse therapy, adoptive cellular immunotherapy (e.g., CAR-T cells, TCRs) and oncolytic viral therapy, can induce cell damage or death to tumor cells, diseased cells, and cells in their surrounding environment. Cells expressing chimeric Tim4 receptors can be administered in combination with the cell damaging/cytotoxic therapy to bind to the phosphatidylserine moieties exposed on the outer leaflet of targeted cells and clear stressed, damaged, diseased, apoptotic, necrotic cells.

In another aspect, a chimeric Tim4 receptor, a polynucleotides encoding a chimeric Tim4 receptor, a chimeric Tim4 receptor vector, or a host cell that expresses a chimeric Tim4 receptor according to any of the embodiments provided herein may be used in a method of treating a subject suffering from a disease, disorder or undesired condition. Embodiments of these methods include administering to a subject a therapeutically effective amount of a pharmaceutical composition including one or more chimeric Tim4 receptors, polynucleotides encoding one or more chimeric Tim4 receptors, vectors comprising polynucleotides encoding one or more chimeric Tim4 receptors, or a population of host cells genetically modified to express one or more chimeric Tim4 receptors according to the present description.

Diseases that may be treated with cells expressing a chimeric Tim4 receptor as described in the present disclosure include cancer and infectious diseases (viral, bacterial, fungal, protozoan infections). Adoptive immune and gene therapies are promising treatments for various types of cancer (Morgan et al., *Science* 314:126, 2006; Schmitt et al., *Hum. Gene Ther.* 20:1240, 2009; June, *J. Clin. Invest.* 117:1466, 2007) and infectious disease (Kitchen et al., *PLoS One* 4:38208, 2009; Rossi et al., *Nat. Biotechnol.* 25:1444, 2007; Zhang et al., *PLoS Pathog.* 6:e1001018, 2010; Luo et al., *J. Mol. Med.* 89:903, 2011).

A wide variety of cancers, including solid tumors and leukemias are amenable to the compositions and methods disclosed herein. Exemplary cancers that may be treated using the receptors, modified host cells, and composition described herein include adenocarcinoma of the breast, prostate, and colon; all forms of bronchogenic carcinoma of the lung; myeloid leukemia; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, Merkel cell, mucinous, non-small cell lung, oat cell, papillary, scirrhous, bronchiolar, bronchogenic, squamous cell, and transitional cell). Additional types of cancers that may be treated using the receptors, modified host cells, and composition described herein include histiocytic disorders; malignant histiocytosis; leukemia; Hodgkin's disease; immunoproliferative small; non-Hodgkin's lymphoma; plasmacytoma; multiple myeloma; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor. Further, the following types of cancers are also contemplated as amenable to treatment using the receptors, modified host cells, and composition described herein: adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin. The types of cancers that may be treated also include angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

Examples of hyperproliferative disorders amenable to therapy using the receptors, modified host cells, and composition described herein include B-cell cancers, including B-cell lymphomas (such as various forms of Hodgkin's disease, non-Hodgkin's lymphoma (NHL) or central nervous system lymphomas), leukemias (such as acute lymphoblastic leukemia (ALL), chronic lymphocytic leukemia (CLL), Hairy cell leukemia, B cell blast transformation of chronic myeloid leukemia) and myelomas (such as multiple myeloma). Additional B cell cancers that may be treated using the receptors, modified host cells, and composition described herein include small lymphocytic lymphoma, B-cell prolymphocytic leukemia, lymphoplasmacytic lymphoma, splenic marginal zone lymphoma, plasma cell myeloma, solitary plasmacytoma of bone, extraosseous plasmacytoma, extra-nodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, intravascular large B-cell lymphoma, primary effusion lymphoma, Burkitt's lymphoma/leukemia, B-cell proliferations of uncertain malignant potential, lymphomatoid granulomatosis, and post-transplant lymphoproliferative disorder.

Infectious diseases include those associated with infectious agents and include any of a variety of bacteria (e.g., pathogenic *E. coli, S. typhimurium, P. aeruginosa, B. anthracis, C. botulinum, C. difficile, C. perfringens, H. pylori, V. cholerae, Listeria* spp., *Rickettsia* spp., *Chlamydia* spp., and the like), mycobacteria, and parasites (including any known parasitic member of the Protozoa). Infectious viruses include eukaryotic viruses, such as adenovirus, bunyavirus, herpesvirus, papovavirus, papillomavirus (e.g., HPV), paramyxovirus, picornavirus, rhabdovirus (e.g., Rabies), orthomyxovirus (e.g., influenza), poxvirus (e.g., Vaccinia), reovirus, retrovirus, lentivirus (e.g., HIV), flavivirus (e.g., HCV, HBV) or the like. In certain embodiments, a composition comprising a chimeric Tim4 receptor according to the present disclosure is used for treating infection with a microbe capable of establishing a persistent infection in a subject.

A chimeric Tim4 receptor of the present disclosure may be administered to a subject in cell-bound form (e.g., gene therapy of target cell population). Thus, for example, a chimeric Tim4 receptor of the present disclosure may be administered to a subject expressed on the surface of T cells, Natural Killer Cells, Natural Killer T cells, B cells, lymphoid precursor cells, antigen presenting cells, dendritic cells, Langerhans cells, myeloid precursor cells, mature myeloid cells, including subsets thereof, or any combination thereof. In certain embodiments, methods of treating a subject comprise administering an effective amount of chimeric Tim4 receptor modified cells (i.e., recombinant cells that express one or more chimeric Tim4 receptors). The chimeric Tim4 receptor modified cells may be xenogeneic, syngeneic, allogeneic, or autologous to the subject.

Pharmaceutical compositions including chimeric Tim4 receptor modified cells may be administered in a manner appropriate to the disease or condition to be treated (or prevented) as determined by persons skilled in the medical art. An appropriate dose, suitable duration, and frequency of administration of the compositions will be determined by such factors as the condition of the patient, size, weight, body surface area, age, sex, type and severity of the disease, particular therapy to be administered, particular form of the active ingredient, time and the method of administration, and other drugs being administered concurrently. The present disclosure provides pharmaceutical compositions comprising chimeric Tim4 receptor modified cells and a pharmaceutically acceptable carrier, diluent, or excipient. Suitable excipients include water, saline, dextrose, glycerol, or the like and combinations thereof. Other suitable infusion medium can be any isotonic medium formulation, including saline, Normosol R (Abbott), Plasma-Lyte A (Baxter), 5% dextrose in water, or Ringer's lactate.

A treatment effective amount of cells in a pharmaceutical composition is at least one cell (for example, one chimeric Tim4 receptor modified T cell) or is more typically greater than $10^2$ cells, for example, up to $10^6$, up to $10^7$, up to $10^8$ cells, up to $10^9$ cells, up to $10^{10}$ cells, or up to $10^{11}$ cells or more. In certain embodiments, the cells are administered in a range from about $10^6$ to about $10^{10}$ cells/m², preferably in a range of about $10^7$ to about $10^9$ cells/m². The number of cells will depend upon the ultimate use for which the composition is intended as well the type of cells included therein. For example, a composition comprising cells modified to contain a chimeric Tim4 receptor will comprise a cell population containing from about 5% to about 95% or more of such cells. In certain embodiments, a composition comprising chimeric Tim4 receptor modified cells comprises a cell population comprising at least 5%, 10%, 15%, 20%, 25%, 30%, 35%, 40%, 45%, 50%, 55%, 60%, 65%, 70%, 75%, 80%, 85%, 90%, 95% or more of such cells. For uses provided herein, the cells are generally in a volume of a liter or less, 500 mls or less, 250 mls or less, or 100 mls or less. Hence the density of the desired cells is typically greater than $10^4$ cells/ml and generally is greater than $10^7$ cells/ml, generally $10^8$ cells/ml or greater. The cells may be administered as a single infusion or in multiple infusions over a range of time. Repeated infusions of chimeric Tim4 receptor modified cells may be separated by days, weeks, months, or even years if relapses of disease or disease activity are present. A clinically relevant number of immune cells can be apportioned into multiple infusions that cumulatively equal or exceed $10^6$, $10^7$, $10^8$, $10^9$, $10^{10}$, or $10^{11}$ cells. A preferred dose for administration of a host cell comprising a recombinant expression vector as described herein is about $10^7$ cells/m², about $5 \times 10^7$ cells/m², about $10^8$ cells/m², about $5 \times 10^8$ cells/m², about $10^9$ cells/m², about $5 \times 10^9$ cells/m², about $10^{10}$ cells/m², about $5 \times 10^{10}$ cells/m², or about $10^{11}$ cells/m².

Chimeric Tim4 receptor compositions as described herein may be administered intravenously, intraperitoneally, intranasally, intratumorly, into the bone marrow, into the lymph node, and/or into cerebrospinal fluid.

Chimeric Tim4 receptor compositions may be administered to a subject in combination with one or more additional therapeutic agents. Examples of therapeutic agents that may be administered in combination with a chimeric Tim4 compositions according to the present description include radiation therapy, adoptive cellular immunotherapy agent (e.g., recombinant TCR, enhanced affinity TCR, CAR, TCR-CAR, scTCR fusion protein, dendritic cell vaccine), antibody therapy, immune checkpoint molecule inhibitor therapy, UV light therapy, electric pulse therapy, high intensity focused ultrasound therapy, oncolytic virus therapy, or a pharmaceutical therapy, such as a chemotherapeutic agent, a therapeutic peptide, a hormone, an aptamer, antibiotic, anti-viral agent, anti-fungal agent, anti-inflammatory agent, a small molecule therapy, or any combination thereof. In certain embodiments, the chimeric Tim4 receptor modified host cells may clear stressed, damaged, apoptotic, necrotic, infected, dead cells displaying surface phosphatidylserine induced by the one or more additional therapeutic agents.

In certain embodiments, the chimeric Tim4 receptor and adoptive cellular immunotherapy agent are administered to the subject in the same host cell or different host cells. In certain embodiments, the chimeric Tim4 receptor and adoptive cellular immunotherapy agent are expressed in the same host cell from the same vector or from separate vectors. In certain embodiments, the chimeric Tim4 receptor and adoptive cellular immunotherapy agent are expressed in the same host cell from a multicistronic vector. In certain embodiments, the chimeric Tim4 receptor is expressed in the same host cell type as the adoptive cellular immunotherapy agent (e.g., the chimeric Tim4 receptor is expressed CD4 T cells and the CAR/or TCR is expressed in CD4 T cells). In other embodiments, the chimeric Tim4 receptor is expressed in a different host cell type as the adoptive immunotherapy agent (e.g., the chimeric Tim4 receptor is expressed CD4 T cells and the CAR/or TCR is expressed in CD8 T cells).

Exemplary antigens that a recombinant TCR, enhanced affinity TCR, CAR, TCR-CAR, or scTCR fusion protein may target include WT-1, mesothelin, MART-1, NY-ESO-1, MAGE-A3, HPV E7, survivin, a Fetoprotein, and a tumor-specific neoantigen.

Exemplary antigens that a CAR may target include CD138, CD38, CD33, CD123, CD72, CD79a, CD79b, mesothelin, PSMA, BCMA, ROR1, MUC-16, L1CAM, CD22, CD19, CD20, CD23, CD24, CD37, CD30, CA125, CD56, c-Met, EGFR, GD-3, HPV E6, HPV E7, MUC-1, HER2, folate receptor α, CD97, CD171, CD179a, CD44v6, WT1, VEGF-α, VEGFR1, IL-13Rα1, IL-13Rα2, IL-11Rα, PSA, FcRH5, NKG2D ligand, NY-ESO-1, TAG-72, CEA, ephrin A2, ephrin B2, Lewis A antigen, Lewis Y antigen, MAGE, MAGE-AL RAGE-1, folate receptor β, EGFRviii, VEGFR-2, LGR5, SSX2, AKAP-4, FLT3, fucosyl GM1, GM3, o-acetyl-GD2, and GD2.

Radiation therapy includes external beam radiation therapy (e.g., conventional external beam radiation therapy, stereotactic radiation, 3-dimensional conformal radiation therapy, intensity-modulated radiation therapy, volumetric modulated arc therapy, particle therapy, proton therapy, and auger therapy), brachytherapy, systemic radioisotope therapy, intraoperative radiotherapy, or any combination thereof.

Exemplary antibodies for use in conjunction with the chimeric Tim4 compositions described herein include rituxmab, pertuzumab, trastuzumab, alemtuzumab, Ibritumomab tiuxetan, Brentuximab vedotin, cetuximab, bevacizumab, abciximab, adalimumab, alefacept, basilizimab, belimumab, bezlotoxumab, canakinumab, certolizumab pegol, daclizumab, denosumab, efalizumab, golimumab, olaratumab, palivizumab, panitumumab, and tocilizumab.

Exemplary inhibitors of immune checkpoint molecules that may be for use in conjunction with the chimeric Tim4 compositions described herein include checkpoint inhibitors targeting PD-L1, PD-L2, CD80, CD86, B7-H3, B7-H4, HVEM, adenosine, GALS, VISTA, CEACAM-1, CEACAM-3, CEACAM-5, PVRL2, PD-1, CTLA-4, BTLA, KIR, LAG3, TIM3, A2aR, CD244/2B4, CD160, TIGIT, LAIR-1, PVRIG/CD112R, or any combination thereof. In certain embodiments, an immune checkpoint inhibitor may be an antibody, a peptide, an RNAi agent, or a small molecule. An antibody specific for CTLA-4 may be ipilimumab or tremelimumab. An antibody specific for PD-1 may be pidilizumab, nivolumab, or pembrolizumab. An antibody specific for PD-L1 may be durvalumab, atezolizumab, or avelumab.

Exemplary chemotherapeutics for use in conjunction with the chimeric Tim4 receptor compositions described herein may include an alkylating agent, a platinum based agent, a cytotoxic agent, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor.

A chemotherapeutic includes non-specific cytotoxic agents that inhibit mitosis or cell division, as well as molecularly targeted therapy that blocks the growth and spread of cancer cells by targeting specific molecules that are involved in tumor growth, progression, and metastasis (e.g., oncogenes). Exemplary non-specific chemotherapeutics for use in conjunction with the tandem expression cassette compositions described herein may include an alkylating agent, a platinum based agent, a cytotoxic agent, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor.

Examples of chemotherapeutic agents considered for use in combination therapies contemplated herein include vemurafenib, dabrafenib, trametinib, cobimetinib, anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), fdabra tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), ibrutinib, venetoclax, crizotinib, alectinib, brigatinib, ceritinib, and vinorelbine (Navelbine®).

Exemplary alkylating agents for use in combination therapies contemplated herein include nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents for use in combination therapies contemplated herein include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary platinum based agents for use in combination therapies contemplated herein include carboplatin, cisplatin, oxaliplatin, nedaplatin, picoplatin, satraplatin, phenanthriplatin, and triplatin tetranitrate.

Exemplary molecularly targeted inhibitors for use in conjunction with the chimeric Tim4 receptor compositions described herein include small molecules that target molecules involved in cancer cell growth and survival, including for example, hormone antagonists, signal transduction inhibitors, gene expression inhibitors (e.g., translation inhibitors), apoptosis inducers, angiogenesis inhibitors (e.g., a VEGF pathway inhibitor), tyrosine kinase inhibitors (e.g., an EGF/EGFR pathway inhibitor), growth factor inhibitors, GTPase inhibitors, serine/threonine kinase inhibitors, transcription factor inhibitors, inhibitors of driver mutations associated with cancer, B-Raf inhibitors, a MEK inhibitors, mTOR inhibitors, adenosine pathway inhibitors, EGFR inhibitors, PI3K inhibitors, BCL2 inhibitors, VEGFR inhibitors, MET inhibitors, MYC inhibitors, BCR-ABL inhibitors, HER2 inhibitors, H-RAS inhibitors, K-RAS inhibitors, PDGFR inhibitors, ALK inhibitors, ROS1 inhibitors, and BTK inhibitors. In certain embodiments, use of molecularly targeted therapy comprises administering a molecularly targeted therapy specific for the molecular target to a subject identified as having a tumor that possesses the molecular target (e.g., driver oncogene). In certain embodiments, the molecular target has an activating mutation. In certain embodiments, use of chimeric Tim4 receptor modified cells in combination with a molecularly targeted inhibitor increases the magnitude of anti-tumor response, the durability of anti-tumor response, or both. In certain embodiments, a lower than typical dose of molecularly targeted therapy is used in combination with chimeric Tim4 receptor modified cells.

Exemplary angiogenesis inhibitors for use in conjunction with the chimeric Tim4 receptor compositions described herein may include, without limitation A6 (Angstrom Pharmaceuticals), ABT-510 (Abbott Laboratories), ABT-627 (Atrasentan) (Abbott Laboratories/Xinlay), ABT-869 (Abbott Laboratories), Actimid (CC4047, Pomalidomide) (Celgene Corporation), AdGVPEDF.11D (GenVec), ADH-1 (Exherin) (Adherex Technologies), AEE788 (Novartis), AG-013736 (Axitinib) (Pfizer), AG3340 (Prinomastat)

(Agouron Pharmaceuticals), AGX1053 (AngioGenex), AGX51 (AngioGenex), ALN-VSP (ALN-VSP O2) (Alnylam Pharmaceuticals), AMG 386 (Amgen), AMG706 (Amgen), Apatinib (YN968D1) (Jiangsu Hengrui Medicine), AP23573 (Ridaforolimus/MK8669) (Ariad Pharmaceuticals), AQ4N (Novavea), ARQ 197 (ArQule), ASA404 (Novartis/Antisoma), Atiprimod (Callisto Pharmaceuticals), ATN-161 (Attenuon), AV-412 (Aveo Pharmaceuticals), AV-951 (Aveo Pharmaceuticals), Avastin (Bevacizumab) (Genentech), AZD2171 (Cediranib/Recentin) (AstraZeneca), BAY 57-9352 (Telatinib) (Bayer), BEZ235 (Novartis), BIBF1120 (Boehringer Ingelheim Pharmaceuticals), BIBW 2992 (Boehringer Ingelheim Pharmaceuticals), BMS-275291 (Bristol-Myers Squibb), BMS-582664 (Brivanib) (Bristol-Myers Squibb), BMS-690514 (Bristol-Myers Squibb), Calcitriol, CCI-779 (Torisel) (Wyeth), CDP-791 (ImClone Systems), Ceflatonin (Homoharringtonine/HHT) (ChemGenex Therapeutics), Celebrex (Celecoxib) (Pfizer), CEP-7055 (Cephalon/Sanofi), CHIR-265 (Chiron Corporation), NGR-TNF, COL-3 (Metastat) (Collagenex Pharaceuticals), Combretastatin (Oxigene), CP-751,871 (Figitumumab) (Pfizer), CP-547,632 (Pfizer), CS-7017 (Daiichi Sankyo Pharma), CT-322 (Angiocept) (Adnexus), Curcumin, Dalteparin (Fragmin) (Pfizer), Disulfiram (Antabuse), E7820 (Eisai Limited), E7080 (Eisai Limited), EMD 121974 (Cilengitide) (EMD Pharmaceuticals), ENMD-1198 (EntreMed), ENMD-2076 (EntreMed), Endostar (Simcere), Erbitux (ImClone/Bristol-Myers Squibb), EZN-2208 (Enzon Pharmaceuticals), EZN-2968 (Enzon Pharmaceuticals), GC1008 (Genzyme), Genistein, GSK1363089 (Foretinib) (GlaxoSmithKline), GW786034 (Pazopanib) (GlaxoSmithKline), GT-111 (Vascular Biogenics Ltd.), IMC-1121B (Ramucirumab) (ImClone Systems), IMC-18F1 (ImClone Systems), IMC-3G3 (ImClone LLC), INCB007839 (Incyte Corporation), INGN 241 (Introgen Therapeutics), Iressa (ZD1839/Gefitinib), LBH589 (Faridak/Panobinostst) (Novartis), Lucentis (Ranibizumab) (Genentech/Novartis), LY317615 (Enzastaurin) (Eli Lilly and Company), Macugen (Pegaptanib) (Pfizer), MEDI522 (Abegrin) (MedImmune), MLN518 (Tandutinib) (Millennium), Neovastat (AE941/Benefin) (Aeterna Zentaris), Nexavar (Bayer/Onyx), NM-3 (Genzyme Corporation), Noscapine (Cougar Biotechnology), NPI-2358 (Nereus Pharmaceuticals), OSI-930 (OSI), Palomid 529 (Paloma Pharmaceuticals, Inc.), Panzem Capsules (2ME2) (EntreMed), Panzem NCD (2ME2) (EntreMed), PF-02341066 (Pfizer), PF-04554878 (Pfizer), PI-88 (Progen Industries/Medigen Biotechnology), PKC412 (Novartis), Polyphenon E (Green Tea Extract) (Polypheno E International, Inc), PPI-2458 (Praecis Pharmaceuticals), PTC299 (PTC Therapeutics), PTK787 (Vatalanib) (Novartis), PXD101 (Belinostat) (CuraGen Corporation), RAD001 (Everolimus) (Novartis), RAF265 (Novartis), Regorafenib (BAY73-4506) (Bayer), Revlimid (Celgene), Retaane (Alcon Research), SN38 (Liposomal) (Neopharm), SNS-032 (BMS-387032) (Sunesis), SOM230 (Pasireotide) (Novartis), Squalamine (Genaera), Suramin, Sutent (Pfizer), Tarceva (Genentech), TB-403 (Thrombogenics), Tempostatin (Collard Biopharmaceuticals), Tetrathiomolybdate (Sigma-Aldrich), TG100801 (TargeGen), Thalidomide (Celgene Corporation), Tinzaparin Sodium, TKI258 (Novartis), TRC093 (Tracon Pharmaceuticals Inc.), VEGF Trap (Aflibercept) (Regeneron Pharmaceuticals), VEGF Trap-Eye (Regeneron Pharmaceuticals), Veglin (VasGene Therapeutics), Bortezomib (Millennium), XL184 (Exelixis), XL647 (Exelixis), XL784 (Exelixis), XL820 (Exelixis), XL999 (Exelixis), ZD6474 (AstraZeneca), Vorinostat (Merck), and ZSTK474.

Exemplary Vascular Endothelial Growth Factor (VEGF) receptor inhibitors for use in conjunction with the chimeric Tim4 receptor compositions described herein may include, but are not limited to, Bevacizumab (Avastin®), axitinib (Inlyta®); Brivanib alaninate (BMS-582664, (S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate); Sorafenib (Nexavar®); Pazopanib (Votrient®); Sunitinib malate (Sutent®); Cediranib (AZD2171, CAS 288383-20-1); Vargatef (BIBF1120, CAS 928326-83-4); Foretinib (GSK1363089); Telatinib (BAY57-9352, CAS 332012-40-5); Apatinib (YN968D1, CAS 811803-05-1); Imatinib (Gleevec®); Ponatinib (AP24534, CAS 943319-70-8); Tivozanib (AV951, CAS 475108-18-0); Regorafenib (BAY73-4506, CAS 755037-03-7); Vatalanib dihydrochloride (PTK787, CAS 212141-51-0); Brivanib (BMS-540215, CAS 649735-46-6); Vandetanib (Caprelsa® or AZD6474); Motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470); Dovitinib dilactic acid (TKI258, CAS 852433-84-2); Linfanib (ABT869, CAS 796967-16-3); Cabozantinib (XL184, CAS 849217-68-1); Lestaurtinib (CAS 111358-88-4); N-[5-[[[5-(1,1-Dimethylethyl)-2-oxazolyl]methyl]thio]-2-thiazolyl]-4-piperidinecarboxamide (BMS38703, CAS 345627-80-7); (3R,4R)-4-Amino-1-((4-((3-methoxyphenyl)amino)pyrrolo[2,1-f][1,2,4]triazin-5-yl)methyl)piperidin-3-ol (BMS690514); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); 4-Methyl-3-[[1-methyl-6-(3-pyridinyl)-1H-pyrazolo[3,4-d]pyrimidin-4-yl]amino]-N-[3-(trifluoromethyl)phenyl]-benzamide (BHG712, CAS 940310-85-0); and Aflibercept (Eylea®).

Exemplary EGF pathway inhibitors for use in conjunction with the chimeric Tim4 receptor compositions described herein may include, without limitation tyrphostin 46, EKB-569, erlotinib (Tarceva®), gefitinib (Iressa®), erbitux, nimotuzumab, lapatinib (Tykerb®), cetuximab (anti-EGFR mAb), [188]Re-labeled nimotuzumab (anti-EGFR mAb), and those compounds that are generically and specifically disclosed in WO 97/02266, EP 0 564 409, WO 99/03854, EP 0 520 722, EP 0 566 226, EP 0 787 722, EP 0 837 063, U.S. Pat. No. 5,747,498, WO 98/10767, WO 97/30034, WO 97/49688, WO 97/38983 and WO 96/33980. Exemplary EGFR antibodies include, but are not limited to, Cetuximab (Erbitux®); Panitumumab (Vectibix®); Matuzumab (EMD-72000); Trastuzumab (Herceptin®); Nimotuzumab (hR3); Zalutumumab; TheraCIM h-R3; MDX0447 (CAS 339151-96-1); and ch806 (mAb-806, CAS 946414-09-1). Exemplary Epidermal growth factor receptor (EGFR) inhibitors include, but not limited to, Osimertinib (Tagrisso®), Erlotinib hydrochloride (Tarceva®), Gefitnib (Iressa®); N-[4-[(3-Chloro-4-fluorophenyl)amino]-7-[[(3"S")-tetrahydro-3-furanyl]oxy]-6-quinazolinyl]-4(dimethylamino)-2-butenamide, Tovok®); Vandetanib (Caprelsa®); Lapatinib (Tykerb®); (3R,4R)-4-Amino-1-((4-((3-methoxyphenyl)amino)pyrrolo[2,1-f][1,2,4]triazin-5-yl)methyl)piperidin-3-ol (BMS690514); Canertinib dihydrochloride (CI-1033); 6-[4-[(4-Ethyl-1-piperazinyl)methyl]phenyl]-N-[(1R)-1-phenylethyl]-7H-Pyrrolo[2,3-d]pyrimidin-4-amine (AEE788, CAS 497839-62-0); Mubritinib (TAK165); Pelitinib (EKB569); Afatinib (BIBW2992); Neratinib (HKI-272); N-[4-[[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS599626); N-(3,4-Dichloro-2-fluorophenyl)-6-methoxy-7-[[(3aα,5β,6aα)- octahydro-2-methylcyclopenta[c]pyrrol-5-yl]methoxy]-4-quinazolinamine (XL647, CAS 781613-23-8); and 4-[4-[[(1R)-1-Phenylethyl]amino]-7H-pyrrolo[2,3-d]pyrimidin-6-yl]-phenol (PKI166, CAS 187724-61-4).

Exemplary mTOR inhibitors for use in conjunction with the chimeric Tim4 receptor compositions described herein may include, without limitation, rapamycin (Rapamune®), and analogs and derivatives thereof; SDZ-RAD; Temsirolimus (Torisel®; also known as CCI-779); Ridaforolimus (formally known as deferolimus, (1R,2R,4S)-4-[(2R)-2[(1R, 9S,12S,15R,16E,18R,19R,21R,23 S,24E,26E,28Z,30S,32S, 35R)-1,18-dihydroxy-19,30-dimethoxy-15,17,21,23,29,35-hexamethyl-2,3,10,14,20-pentaoxo-11,36-dioxa-4-azatricyclo[30.3.1.0$^{4,9}$]hexatriaconta-16,24,26,28-tetraen-12-yl]propyl]-2-methoxycyclohexyl dimethylphosphinate, also known as AP23573 and MK8669, and described in PCT Publication No. WO 03/064383); Everolimus (Afinitor® or RAD001); Rapamycin (AY22989, Sirolimus®); Simapimod (CAS 164301-51-3); (5-{2,4-Bis[(3 S)-3-methylmorpholin-4-yl]pyrido[2,3-d]pyrimidin-7-yl}-2-methoxyphenyl) methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502, CAS 1013101-36-4); and N$^2$-[1,4-dioxo-[[4-(4-oxo-8-phenyl-4H-1-benzopyran-2-yl)morpholinium-4-yl]methoxy]butyl]R-arginylglycyl-L-α-aspartylL-serine-, inner salt (SF1126, CAS 936487-67-1).

Exemplary Phosphoinositide 3-kinase (PI3K) inhibitors for use in conjunction with the chimeric Tim4 receptor compositions described herein may include, but are not limited to, 4-[2-(1H-Indazol-4-yl)-6-[[4-(methylsulfonyl) piperazin-1-yl]methyl]thieno[3,2-d]pyrimidin-4-yl]morpholine (also known as GDC 0941 and described in PCT Publication Nos. WO 09/036082 and WO 09/055730); 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806); 4-(trifluoromethyl)-5-(2, 6-dimorpholinopyrimidin-4-yl)pyridin-2-amine (also known as BKM120 or NVP-BKM120, and described in PCT Publication No. WO2007/084786); Tozasertib (VX680 or MK-0457, CAS 639089-54-6); (5Z)-5-[[4-(4-Pyridinyl)-6-quinolinyl]methylene]-2,4-thiazolidinedione (GSK1059615, CAS 958852-01-2); (1E,4S,4aR,5R,6aS, 9aR)-5-(Acetyloxy)-1-[(di-2-propenylamino)methylene]-4, 4a,5,6,6a,8,9,9a-octahydro-11-hydroxy-4-(methoxymethyl)-4a,6a-dimethyl-cyclopenta[5,6]naphtho[1,2-c]pyran-2,7,10(1H)-trione (PX866, CAS 502632-66-8); and 8-Phenyl-2-(morpholin-4-yl)-chromen-4-one (LY294002, CAS 154447-36-6). Exemplary Protein Kinase B (PKB) or AKT inhibitors include, but are not limited to. 8-[4-(1-Aminocyclobutyl)phenyl]-9-phenyl-1,2,4-triazolo[3,4-f][1, 6]naphthyridin-3(2H)-one (MK-2206, CAS 1032349-93-1); Perifosine (KRX0401); 4-Dodecyl-N-1,3,4-thiadiazol-2-yl-benzenesulfonamide (PHT-427, CAS 1191951-57-1); 4-[2-(4-Amino-1,2,5-oxadiazol-3-yl)-1-ethyl-7-[(3S)-3-piperidinylmethoxy]-1H-imidazo[4,5-c]pyridin-4-yl]-2-methyl-3-butyn-2-ol (GSK690693, CAS 937174-76-0); 8-(1-Hydroxyethyl)-2-methoxy-3-[(4-methoxyphenyl)methoxy]-6H-dibenzo[b,d]pyran-6-one (palomid 529, P529, or SG-00529); Tricirbine (6-Amino-4-methyl-8-(β-D-ribofuranosyl)-4H,8H-pyrrolo[4,3,2-de]pyrimido[4,5-c]pyridazine); (αS)-α-[[[5-(3-Methyl-1H-indazol-5-yl)-3-pyridinyl]oxy] methyl]-benzeneethanamine (A674563, CAS 552325-73-2); 4-[(4-Chlorophenyl)methyl]-1-(7H-pyrrolo[2,3-d]pyrimidin-4-yl)-4-piperidinamine (CCT128930, CAS 885499-61-6); 4-(4-Chlorophenyl)-4-[4-(1H pyrazol-4-yl)phenyl]-piperidine (AT7867, CAS 857531-00-1); and Archexin (RX-0201, CAS 663232-27-7).

In certain embodiments, a tyrosine kinase inhibitor used in combination with chimeric Tim4 receptor modified cells is an anaplastic lymphoma kinase (ALK) inhibitor. Exemplary ALK inhibitors include crizotinib, ceritinib, alectinib, brigatinib, dalantercept, entrectinib, and lorlatinib.

In certain embodiments where chimeric Tim4 receptor modified cells are administered in combination with one or more additional therapies, the one or more additional therapies may be administered at a dose that might otherwise be considered subtherapeutic if administered as a monotherapy. In such embodiments, the chimeric Tim4 receptor composition may provide an additive or synergistic effect such that the one or more additional therapies can be administered at a lower dose. Combination therapy includes administration of a chimeric Tim4 receptor compositions as described herein before an additional therapy (e.g., 1 day to 30 days or more before the additional therapy), concurrently with an additional therapy (on the same day), or after an additional therapy (e.g., 1 day-30 days or more after the additional therapy). In certain embodiments, the chimeric Tim4 receptor modified cells are administered after administration of the one or more additional therapies. In further embodiments, the chimeric Tim4 receptor modified cells are administered 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days after administration of the one or more additional therapies. In still further embodiments, the chimeric Tim4 receptor modified cells are administered within 4 weeks, within 3 weeks, within 2 weeks, or within 1 week after administration of the one or more additional therapies. Where the one or more additional therapies involves multiple doses, the chimeric Tim4 receptor modified cells may be administered after the initial dose of the one or more additional therapies, after the final dose of the one or more additional therapies, or in between multiple doses of the one or more additional therapies.

In certain embodiments, methods of the present disclosure include a depletion step. A depletion step to remove chimeric Tim4 receptors from the subject may occur after a sufficient amount of time for therapeutic benefit in order to mitigate toxicity to a subject. In such embodiments, the chimeric Tim4 receptor vector may include an inducible suicide gene, such as iCASP9, inducible Fas, or HSV-TK. Similarly, a chimeric Tim4 receptor vector may be designed for expression of a known cell surface antigen such as CD20 or truncated EGFR (SEQ ID NO:52) that facilitates depletion of transduced cells through infusion of an associated monoclonal antibody (mAb), for example, Rituximab for CD20 or Cetuximab for EGFR. Alemtuzumab, which targets CD52 present on the surface of mature lymphocytes, may also be used to deplete transduced B cells, T cells, or natural killer cells.

Subjects that can be treated by the compositions and methods of the present disclosure include animals, such as humans, primates, cows, horses, sheep, dogs, cats, mice, rats, rabbits, guinea pigs, or pigs. The subject may be male or female, and can be any suitable age, including infant, juvenile, adolescent, adult, and geriatric subjects.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including U.S. Provisional Patent Application No. 62/649,491, filed Mar. 28, 2018, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A chimeric Tim4 receptor comprising a single chain chimeric protein, the single chain chimeric protein comprising:
   a receptor binding domain comprising a Tim4 binding domain;
   an intracellular signaling domain comprising a CD28 costimulatory signaling domain and a CD3ζ signaling domain; and
   a transmembrane domain positioned between and connecting the receptor binding domain and the intracellular signaling domain.

2. The chimeric Tim4 receptor of claim 1, wherein the Tim4 binding domain comprises the amino acid sequence of SEQ ID NO:2 or amino acids 25-314 of SEQ ID NO:2.

3. The chimeric Tim4 receptor of claim 1, wherein the receptor binding domain further comprises an extracellular spacer domain positioned between the Tim4 binding domain and the transmembrane domain.

4. The chimeric Tim4 receptor of claim 3, wherein the extracellular spacer domain comprises an immunoglobulin hinge region, a hinge region of a type 1 membrane protein, a stalk region of a type II C-lectin, an immunoglobulin constant domain, or a fragment thereof.

5. The chimeric Tim4 receptor of claim 4, wherein the extracellular spacer domain comprises:
   (a) an IgG1, IgG2, IgG3, IgG4, IgA, or IgD hinge region;
   (b) a modified IgG4 hinge region comprising the amino acid sequence of SEQ ID NO: 3;
   (c) a stalk region of a type II C-lectin selected from CD23, CD69, CD72, CD94, NKG2A, and NKG2D;
   (d) a hinge region of a type 1 membrane protein selected from CD8a, CD4, CD28 and CD7; or
   (e) an immunoglobulin constant region domain selected from a CH1 domain, a CH2 domain, a CH3 domain, or any combination thereof.

6. The chimeric Tim4 receptor of claim 1, wherein the transmembrane domain comprises a Tim4, CD27, CD28, CD8, 4-1BB, OX40, CD30, CD40, PD-1, ICOS, lymphocyte function-associated antigen-1 (LFA-1), CD2, CD7, LIGHT, NKG2C, or B7-H3 transmembrane domain.

7. The chimeric Tim4 receptor of claim 6, wherein the transmembrane domain comprises a Tim4 transmembrane domain comprising the amino acid sequence of SEQ ID NO:28, a CD27 transmembrane domain comprising the amino acid sequence of SEQ ID NO:32, a CD28 transmembrane domain comprising the amino acid sequence of SEQ ID NO:29, a 4-1BB transmembrane domain comprising the amino acid sequence of SEQ ID NO:30, an OX40 transmembrane domain comprising the amino acid sequence of SEQ ID NO:31, a CD30 transmembrane domain comprising the amino acid sequence of SEQ ID NO:36, a CD40 transmembrane domain comprising the amino acid sequence of SEQ ID NO:37, a PD-1 transmembrane domain comprising the amino acid sequence of SEQ ID NO:38, an ICOS transmembrane domain comprising the amino acid sequence of SEQ ID NO: 33, a LFA-1 transmembrane domain comprising the amino acid sequence of SEQ ID NO: 35, a CD2 transmembrane domain comprising the amino acid sequence of SEQ ID NO:34, or a CD7 transmembrane domain comprising the amino acid sequence of SEQ ID NO:39, a LIGHT transmembrane domain comprising the amino acid sequence of SEQ ID NO:40, a NKG2C transmembrane domain comprising the amino acid sequence of SEQ ID NO:41, or a B7-H3 transmembrane domain comprising the amino acid sequence of SEQ ID NO:42=.

8. The chimeric Tim4 receptor of claim 1, wherein the CD28 costimulatory signaling domain comprises the amino acid sequence of SEQ ID NO:4 or 62.

9. The chimeric Tim4 receptor of claim 1, wherein the transmembrane domain is a CD28 transmembrane domain.

10. The chimeric Tim4 receptor of claim 1, wherein the CD3ζ signaling domain comprises the amino acid sequence of SEQ ID NO: 63 or 19.

11. The chimeric Tim4 receptor of claim 1, wherein:
the chimeric Tim4 receptor comprises the amino acid sequence of SEQ ID NO: 69 or amino acids 25-495 of SEQ ID NO:69.

* * * * *

SEQUENCE LISTING

<160> NUMBER OF SEQ ID NOS: 69

<210> SEQ ID NO 1
<211> LENGTH: 378
<212> TYPE: PRT
<213> ORGANISM: Homo sapiens
<220> FEATURE:
<223> OTHER INFORMATION: Tim4 from UniProt Ref. Q96H15-1

<400> SEQUENCE: 1

Met Ser Lys Glu Pro Leu Ile Leu Trp Leu Met Ile Glu Phe Trp Trp
1               5                   10                  15

Leu Tyr Leu Thr Pro Val Thr Ser Glu Thr Val Val Thr Glu Val Leu
                20                  25                  30

Gly His Arg Val Thr Leu Pro Cys Leu Tyr Ser Ser Trp Ser His Asn
            35                  40                  45

Ser Asn Ser Met Cys Trp Gly Lys Asp Gln Cys Pro Tyr Ser Gly Cys
    50                  55                  60

Lys Glu Ala Leu Ile Arg Thr Asp Gly Met Arg Val Thr Ser Arg Lys
65                  70                  75                  80

Ser Ala Lys Tyr Arg Leu Gln Gly Thr Ile Pro Arg Gly Asp Val Ser
                85                  90                  95

Leu Thr Ile Leu Asn Pro Ser Glu Ser Asp Ser Gly Val Tyr Cys Cys
            100                 105                 110

Arg Ile Glu Val Pro Gly Trp Phe Asn Asp Val Lys Ile Asn Val Arg
        115                 120                 125

Leu Asn Leu Gln Arg Ala Ser Thr Thr Thr His Arg Thr Ala Thr Thr
    130                 135                 140

Thr Thr Arg Arg Thr Thr Thr Thr Ser Pro Thr Thr Thr Arg Gln Met
145                 150                 155                 160

Thr Thr Thr Pro Ala Ala Leu Pro Thr Thr Val Val Thr Thr Pro Asp
                165                 170                 175

Leu Thr Thr Gly Thr Pro Leu Gln Met Thr Thr Ile Ala Val Phe Thr
            180                 185                 190

Thr Ala Asn Thr Cys Leu Ser Leu Thr Pro Ser Thr Leu Pro Glu Glu
        195                 200                 205

Ala Thr Gly Leu Leu Thr Pro Glu Pro Ser Lys Glu Gly Pro Ile Leu
    210                 215                 220

Thr Ala Glu Ser Glu Thr Val Leu Pro Ser Asp Ser Trp Ser Ser Val
225                 230                 235                 240

Glu Ser Thr Ser Ala Asp Thr Val Leu Leu Thr Ser Lys Glu Ser Lys
                245                 250                 255

Val Trp Asp Leu Pro Ser Thr Ser His Val Ser Met Trp Lys Thr Ser
            260                 265                 270

Asp Ser Val Ser Ser Pro Gln Pro Gly Ala Ser Asp Thr Ala Val Pro
        275                 280                 285

Glu Gln Asn Lys Thr Thr Lys Thr Gly Gln Met Asp Gly Ile Pro Met
    290                 295                 300

Ser Met Lys Asn Glu Met Pro Ile Ser Gln Leu Leu Met Ile Ile Ala
305                 310                 315                 320

Pro Ser Leu Gly Phe Val Leu Phe Ala Leu Phe Val Ala Phe Leu Leu
                325                 330                 335

Arg Gly Lys Leu Met Glu Thr Tyr Cys Ser Gln Lys His Thr Arg Leu
            340                 345                 350

Asp Tyr Ile Gly Asp Ser Lys Asn Val Leu Asn Asp Val Gln His Gly

```
                     355                 360                 365
Arg Glu Asp Glu Asp Gly Leu Phe Thr Leu
                370                 375

<210> SEQ ID NO 2
<211> LENGTH: 314
<212> TYPE: PRT
<213> ORGANISM: Homo sapiens
<220> FEATURE:
<223> OTHER INFORMATION: Tim4 binding domain, amino acids 1-24 signal
      peptide

<400> SEQUENCE: 2

Met Ser Lys Glu Pro Leu Ile Leu Trp Leu Met Ile Glu Phe Trp Trp
1               5                   10                  15

Leu Tyr Leu Thr Pro Val Thr Ser Glu Thr Val Val Thr Glu Val Leu
            20                  25                  30

Gly His Arg Val Thr Leu Pro Cys Leu Tyr Ser Ser Trp Ser His Asn
        35                  40                  45

Ser Asn Ser Met Cys Trp Gly Lys Asp Gln Cys Pro Tyr Ser Gly Cys
    50                  55                  60

Lys Glu Ala Leu Ile Arg Thr Asp Gly Met Arg Val Thr Ser Arg Lys
65                  70                  75                  80

Ser Ala Lys Tyr Arg Leu Gln Gly Thr Ile Pro Arg Gly Asp Val Ser
                85                  90                  95

Leu Thr Ile Leu Asn Pro Ser Glu Ser Asp Ser Gly Val Tyr Cys Cys
            100                 105                 110

Arg Ile Glu Val Pro Gly Trp Phe Asn Asp Val Lys Ile Asn Val Arg
        115                 120                 125

Leu Asn Leu Gln Arg Ala Ser Thr Thr Thr His Arg Thr Ala Thr Thr
    130                 135                 140

Thr Thr Arg Arg Thr Thr Thr Thr Ser Pro Thr Thr Thr Arg Gln Met
145                 150                 155                 160

Thr Thr Thr Pro Ala Ala Leu Pro Thr Thr Val Val Thr Thr Pro Asp
                165                 170                 175

Leu Thr Thr Gly Thr Pro Leu Gln Met Thr Thr Ile Ala Val Phe Thr
            180                 185                 190

Thr Ala Asn Thr Cys Leu Ser Leu Thr Pro Ser Thr Leu Pro Glu Glu
        195                 200                 205

Ala Thr Gly Leu Leu Thr Pro Glu Pro Ser Lys Glu Gly Pro Ile Leu
    210                 215                 220

Thr Ala Glu Ser Glu Thr Val Leu Pro Ser Asp Ser Trp Ser Ser Val
225                 230                 235                 240

Glu Ser Thr Ser Ala Asp Thr Val Leu Leu Thr Ser Lys Glu Ser Lys
                245                 250                 255

Val Trp Asp Leu Pro Ser Thr Ser His Val Ser Met Trp Lys Thr Ser
            260                 265                 270

Asp Ser Val Ser Ser Pro Gln Pro Gly Ala Ser Asp Thr Ala Val Pro
        275                 280                 285

Glu Gln Asn Lys Thr Thr Lys Thr Gly Gln Met Asp Gly Ile Pro Met
    290                 295                 300

Ser Met Lys Asn Glu Met Pro Ile Ser Gln
305                 310

<210> SEQ ID NO 3
<211> LENGTH: 12
```

```
<212> TYPE: PRT
<213> ORGANISM: Homo sapiens
<220> FEATURE:
<223> OTHER INFORMATION: modified IgG4 hinge

<400> SEQUENCE: 3

Glu Ser Lys Tyr Gly Pro Pro Cys Pro Pro Cys Pro
1               5                   10

<210> SEQ ID NO 4
<211> LENGTH: 41
<212> TYPE: PRT
<213> ORGANISM: Homo sapiens
<220> FEATURE:
<223> OTHER INFORMATION: wildtype CD28 costimulatory signaling domain

<400> SEQUENCE: 4

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 5
<211> LENGTH: 42
<212> TYPE: PRT
<213> ORGANISM: Homo sapiens
<220> FEATURE:
<223> OTHER INFORMATION: OX40 costimulatory signaling domain from
      UniProt Ref. P43489, cytoplasmic domain

<400> SEQUENCE: 5

Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
            20                  25                  30

Ala Asp Ala His Ser Thr Leu Ala Lys Ile
        35                  40

<210> SEQ ID NO 6
<211> LENGTH: 116
<212> TYPE: PRT
<213> ORGANISM: Homo sapiens
<220> FEATURE:
<223> OTHER INFORMATION: CD2 costimulatory signaling domain from UniProt
      Ref. P06729, cytoplasmic domain

<400> SEQUENCE: 6

Lys Arg Lys Lys Gln Arg Ser Arg Arg Asn Asp Glu Glu Leu Glu Thr
1               5                   10                  15

Arg Ala His Arg Val Ala Thr Glu Glu Arg Gly Arg Lys Pro His Gln
            20                  25                  30

Ile Pro Ala Ser Thr Pro Gln Asn Pro Ala Thr Ser Gln His Pro Pro
        35                  40                  45

Pro Pro Pro Gly His Arg Ser Gln Ala Pro Ser His Arg Pro Pro Pro
    50                  55                  60

Pro Gly His Arg Val Gln His Gln Pro Gln Lys Arg Pro Pro Ala Pro
65                  70                  75                  80

Ser Gly Thr Gln Val His Gln Gln Lys Gly Pro Pro Leu Pro Arg Pro
                85                  90                  95

Arg Val Gln Pro Lys Pro Pro His Gly Ala Ala Glu Asn Ser Leu Ser
```

-continued

```
               100                 105                 110
Pro Ser Ser Asn
        115

<210> SEQ ID NO 7
<211> LENGTH: 42
<212> TYPE: PRT
<213> ORGANISM: Homo sapiens
<220> FEATURE:
<223> OTHER INFORMATION: 4-1BB costimulatory signaling domain

<400> SEQUENCE: 7

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 8
<211> LENGTH: 48
<212> TYPE: PRT
<213> ORGANISM: Homo sapiens
<220> FEATURE:
<223> OTHER INFORMATION: CD27 costimulatory signaling domain from
      UniProt Ref. P26842, cytoplasmic domain

<400> SEQUENCE: 8

Gln Arg Arg Lys Tyr Arg Ser Asn Lys Gly Glu Ser Pro Val Glu Pro
1               5                   10                  15

Ala Glu Pro Cys His Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45

<210> SEQ ID NO 9
<211> LENGTH: 29
<212> TYPE: PRT
<213> ORGANISM: Homo sapiens
<220> FEATURE:
<223> OTHER INFORMATION: ICAM-1 costimulatory signaling domain from
      UniProt Ref. P05362, cytoplasmic domain

<400> SEQUENCE: 9

Asn Arg Gln Arg Lys Ile Lys Lys Tyr Arg Leu Gln Gln Ala Gln Lys
1               5                   10                  15

Gly Thr Pro Met Lys Pro Asn Thr Gln Ala Thr Pro Pro
            20                  25

<210> SEQ ID NO 10
<211> LENGTH: 46
<212> TYPE: PRT
<213> ORGANISM: Homo sapiens
<220> FEATURE:
<223> OTHER INFORMATION: LFA-1 costimulatory signaling domain from
      UniProt Ref. P05107, cytoplasmic domain

<400> SEQUENCE: 10

Lys Ala Leu Ile His Leu Ser Asp Leu Arg Glu Tyr Arg Arg Phe Glu
1               5                   10                  15

Lys Glu Lys Leu Lys Ser Gln Trp Asn Asn Asp Asn Pro Leu Phe Lys
            20                  25                  30

Ser Ala Thr Thr Thr Val Met Asn Pro Lys Phe Ala Glu Ser
```

<210> SEQ ID NO 11
<211> LENGTH: 38
<212> TYPE: PRT
<213> ORGANISM: Homo sapiens
<220> FEATURE:
<223> OTHER INFORMATION: COS costimulatory signaling domain from UniProt
       Ref. Q9Y6W8, cytoplasmic domain

<400> SEQUENCE: 11

Cys Trp Leu Thr Lys Lys Lys Tyr Ser Ser Ser Val His Asp Pro Asn
1               5                   10                  15

Gly Glu Tyr Met Phe Met Arg Ala Val Asn Thr Ala Lys Lys Ser Arg
            20                  25                  30

Leu Thr Asp Val Thr Leu
        35

<210> SEQ ID NO 12
<211> LENGTH: 188
<212> TYPE: PRT
<213> ORGANISM: Homo sapiens
<220> FEATURE:
<223> OTHER INFORMATION: CD30 costimulatory signaling domain from
       UniProt Ref. P28908, cytoplasmic domain

<400> SEQUENCE: 12

His Arg Arg Ala Cys Arg Lys Arg Ile Arg Gln Lys Leu His Leu Cys
1               5                   10                  15

Tyr Pro Val Gln Thr Ser Gln Pro Lys Leu Glu Leu Val Asp Ser Arg
            20                  25                  30

Pro Arg Arg Ser Ser Thr Gln Leu Arg Ser Gly Ala Ser Val Thr Glu
        35                  40                  45

Pro Val Ala Glu Glu Arg Gly Leu Met Ser Gln Pro Leu Met Glu Thr
    50                  55                  60

Cys His Ser Val Gly Ala Ala Tyr Leu Glu Ser Leu Pro Leu Gln Asp
65                  70                  75                  80

Ala Ser Pro Ala Gly Gly Pro Ser Ser Pro Arg Asp Leu Pro Glu Pro
                85                  90                  95

Arg Val Ser Thr Glu His Thr Asn Asn Lys Ile Glu Lys Ile Tyr Ile
            100                 105                 110

Met Lys Ala Asp Thr Val Ile Val Gly Thr Val Lys Ala Glu Leu Pro
        115                 120                 125

Glu Gly Arg Gly Leu Ala Gly Pro Ala Glu Pro Glu Leu Glu Glu Glu
    130                 135                 140

Leu Glu Ala Asp His Thr Pro His Tyr Pro Glu Gln Glu Thr Glu Pro
145                 150                 155                 160

Pro Leu Gly Ser Cys Ser Asp Val Met Leu Ser Val Glu Glu Glu Gly
                165                 170                 175

Lys Glu Asp Pro Leu Pro Thr Ala Ala Ser Gly Lys
            180                 185

<210> SEQ ID NO 13
<211> LENGTH: 62
<212> TYPE: PRT
<213> ORGANISM: Homo sapiens
<220> FEATURE:
<223> OTHER INFORMATION: D40 costimulatory signaling domain from UniProt
       Ref. P25942, cytoplasmic domain

<400> SEQUENCE: 13

```
Lys Lys Val Ala Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
                20                  25                  30

Ala Ala Pro Val Gln Glu Thr Leu His Gly Cys Gln Pro Val Thr Gln
                35                  40                  45

Glu Asp Gly Lys Glu Ser Arg Ile Ser Val Gln Glu Arg Gln
        50                  55                  60

<210> SEQ ID NO 14
<211> LENGTH: 97
<212> TYPE: PRT
<213> ORGANISM: Homo sapiens
<220> FEATURE:
<223> OTHER INFORMATION: PD-1 costimulatory signaling domain from
      UniProt Ref. Q15116, cytoplasmic domain

<400> SEQUENCE: 14

Cys Ser Arg Ala Ala Arg Gly Thr Ile Gly Ala Arg Arg Thr Gly Gln
1               5                   10                  15

Pro Leu Lys Glu Asp Pro Ser Ala Val Pro Val Phe Ser Val Asp Tyr
                20                  25                  30

Gly Glu Leu Asp Phe Gln Trp Arg Glu Lys Thr Pro Glu Pro Pro Val
            35                  40                  45

Pro Cys Val Pro Glu Gln Thr Glu Tyr Ala Thr Ile Val Phe Pro Ser
    50                  55                  60

Gly Met Gly Thr Ser Ser Pro Ala Arg Arg Gly Ser Ala Asp Gly Pro
65              70                  75                  80

Arg Ser Ala Gln Pro Leu Arg Pro Glu Asp Gly His Cys Ser Trp Pro
                85                  90                  95

Leu

<210> SEQ ID NO 15
<211> LENGTH: 39
<212> TYPE: PRT
<213> ORGANISM: Homo sapiens
<220> FEATURE:
<223> OTHER INFORMATION: CD7 costimulatory signaling domain from UniProt
      Ref. P09564, cytoplasmic domain

<400> SEQUENCE: 15

Arg Thr Gln Ile Lys Lys Leu Cys Ser Trp Arg Asp Lys Asn Ser Ala
1               5                   10                  15

Ala Cys Val Val Tyr Glu Asp Met Ser His Ser Arg Cys Asn Thr Leu
                20                  25                  30

Ser Ser Pro Asn Gln Tyr Gln
        35

<210> SEQ ID NO 16
<211> LENGTH: 37
<212> TYPE: PRT
<213> ORGANISM: Homo sapiens
<220> FEATURE:
<223> OTHER INFORMATION: LIGHT costimulatory signaling domain from
      UniProt Ref. O43557, cytoplasmic domain

<400> SEQUENCE: 16

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
```

-continued

```
                    20                  25                  30

Cys Ser Val Ala Arg
        35

<210> SEQ ID NO 17
<211> LENGTH: 70
<212> TYPE: PRT
<213> ORGANISM: Homo sapiens
<220> FEATURE:
<223> OTHER INFORMATION: NKG2C costimulatory signaling domain from
      UniProt Ref. P26717, cytoplasmic domain

<400> SEQUENCE: 17

Met Ser Lys Gln Arg Gly Thr Phe Ser Glu Val Ser Leu Ala Gln Asp
1               5                   10                  15

Pro Lys Arg Gln Gln Arg Lys Pro Lys Gly Asn Lys Ser Ser Ile Ser
            20                  25                  30

Gly Thr Glu Gln Glu Ile Phe Gln Val Glu Leu Asn Leu Gln Asn Pro
        35                  40                  45

Ser Leu Asn His Gln Gly Ile Asp Lys Ile Tyr Asp Cys Gln Gly Leu
    50                  55                  60

Leu Pro Pro Pro Glu Lys
65                  70

<210> SEQ ID NO 18
<211> LENGTH: 47
<212> TYPE: PRT
<213> ORGANISM: Homo sapiens
<220> FEATURE:
<223> OTHER INFORMATION: B7-H3 costimulatory signaling domain from
      UniProt Ref. Q5ZPR3, cytoplasmic domain

<400> SEQUENCE: 18

Cys Trp Arg Lys Ile Lys Gln Ser Cys Glu Glu Glu Asn Ala Gly Ala
1               5                   10                  15

Glu Asp Gln Asp Gly Glu Gly Glu Gly Ser Lys Thr Ala Leu Gln Pro
            20                  25                  30

Leu Lys His Ser Asp Ser Lys Glu Asp Asp Gly Gln Glu Ile Ala
        35                  40                  45

<210> SEQ ID NO 19
<211> LENGTH: 112
<212> TYPE: PRT
<213> ORGANISM: Homo sapiens
<220> FEATURE:
<223> OTHER INFORMATION: mutated human CD3zeta ITAM-containing
      activating domain

<400> SEQUENCE: 19

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
            85                  90                  95
```

Thr Lys Asp Thr Tyr Asp Ala Leu His Met Gln Ala Leu Pro Pro Arg
            100                 105                 110

<210> SEQ ID NO 20
<211> LENGTH: 45
<212> TYPE: PRT
<213> ORGANISM: Homo sapiens
<220> FEATURE:
<223> OTHER INFORMATION: CD3gamma ITAM-containing activating domain from
      UniProt Ref. P09693, cytoplasmic domain

<400> SEQUENCE: 20

Gly Gln Asp Gly Val Arg Gln Ser Arg Ala Ser Asp Lys Gln Thr Leu
1               5                   10                  15

Leu Pro Asn Asp Gln Leu Tyr Gln Pro Leu Lys Asp Arg Glu Asp Asp
            20                  25                  30

Gln Tyr Ser His Leu Gln Gly Asn Gln Leu Arg Arg Asn
        35                  40                  45

<210> SEQ ID NO 21
<211> LENGTH: 45
<212> TYPE: PRT
<213> ORGANISM: Homo sapiens
<220> FEATURE:
<223> OTHER INFORMATION: CD3delta ITAM-containing activating domain from
      UniProt Ref. P04234, cytoplasmic domain

<400> SEQUENCE: 21

Gly His Glu Thr Gly Arg Leu Ser Gly Ala Ala Asp Thr Gln Ala Leu
1               5                   10                  15

Leu Arg Asn Asp Gln Val Tyr Gln Pro Leu Arg Asp Arg Asp Asp Ala
            20                  25                  30

Gln Tyr Ser His Leu Gly Gly Asn Trp Ala Arg Asn Lys
        35                  40                  45

<210> SEQ ID NO 22
<211> LENGTH: 55
<212> TYPE: PRT
<213> ORGANISM: Homo sapiens
<220> FEATURE:
<223> OTHER INFORMATION: CD3epsilon ITAM-containing activating domain
      from UniProt Ref. P07766, cytoplasmic domain

<400> SEQUENCE: 22

Lys Asn Arg Lys Ala Lys Ala Lys Pro Val Thr Arg Gly Ala Gly Ala
1               5                   10                  15

Gly Gly Arg Gln Arg Gly Gln Asn Lys Glu Arg Pro Pro Pro Val Pro
            20                  25                  30

Asn Pro Asp Tyr Glu Pro Ile Arg Lys Gly Gln Arg Asp Leu Tyr Ser
        35                  40                  45

Gly Leu Asn Gln Arg Arg Ile
    50                  55

<210> SEQ ID NO 23
<211> LENGTH: 93
<212> TYPE: PRT
<213> ORGANISM: Homo sapiens
<220> FEATURE:
<223> OTHER INFORMATION: CD5 ITAM-containing activating domain from
      UniProt Ref. P06127, cytoplasmic domain

<400> SEQUENCE: 23

Lys Lys Leu Val Lys Lys Phe Arg Gln Lys Lys Gln Arg Gln Trp Ile

```
                1               5                  10                 15
Gly Pro Thr Gly Met Asn Gln Asn Met Ser Phe His Arg Asn His Thr
                20                  25                  30
Ala Thr Val Arg Ser His Ala Glu Asn Pro Thr Ala Ser His Val Asp
                35                  40                  45
Asn Glu Tyr Ser Gln Pro Pro Arg Asn Ser His Leu Ser Ala Tyr Pro
         50                  55                  60
Ala Leu Glu Gly Ala Leu His Arg Ser Ser Met Gln Pro Asp Asn Ser
65                  70                  75                  80
Ser Asp Ser Asp Tyr Asp Leu His Gly Ala Gln Arg Leu
                85                  90

<210> SEQ ID NO 24
<211> LENGTH: 141
<212> TYPE: PRT
<213> ORGANISM: Homo sapiens
<220> FEATURE:
<223> OTHER INFORMATION: CD22 ITAM-containing activating domain from
      UniProt Ref. P20273, cytoplasmic domain

<400> SEQUENCE: 24

Lys Leu Gln Arg Arg Trp Lys Arg Thr Gln Ser Gln Gln Gly Leu Gln
1               5                  10                  15
Glu Asn Ser Ser Gly Gln Ser Phe Phe Val Arg Asn Lys Lys Val Arg
                20                  25                  30
Arg Ala Pro Leu Ser Glu Gly Pro His Ser Leu Gly Cys Tyr Asn Pro
            35                  40                  45
Met Met Glu Asp Gly Ile Ser Tyr Thr Thr Leu Arg Phe Pro Glu Met
50                  55                  60
Asn Ile Pro Arg Thr Gly Asp Ala Glu Ser Ser Glu Met Gln Arg Pro
65                  70                  75                  80
Pro Pro Asp Cys Asp Asp Thr Val Thr Tyr Ser Ala Leu His Lys Arg
                85                  90                  95
Gln Val Gly Asp Tyr Glu Asn Val Ile Pro Asp Phe Pro Glu Asp Glu
                100                 105                 110
Gly Ile His Tyr Ser Glu Leu Ile Gln Phe Gly Val Gly Glu Arg Pro
            115                 120                 125
Gln Ala Gln Glu Asn Val Asp Tyr Val Ile Leu Lys His
        130                 135                 140

<210> SEQ ID NO 25
<211> LENGTH: 61
<212> TYPE: PRT
<213> ORGANISM: Homo sapiens
<220> FEATURE:
<223> OTHER INFORMATION: CD79a ITAM-containing activating domain

<400> SEQUENCE: 25

Arg Lys Arg Trp Gln Asn Glu Lys Leu Gly Leu Asp Ala Gly Asp Glu
1               5                  10                  15
Tyr Glu Asp Glu Asn Leu Tyr Glu Gly Leu Asn Leu Asp Asp Cys Ser
                20                  25                  30
Met Tyr Glu Asp Ile Ser Arg Gly Leu Gln Gly Thr Tyr Gln Asp Val
            35                  40                  45
Gly Ser Leu Asn Ile Gly Asp Val Gln Leu Glu Lys Pro
        50                  55                  60

<210> SEQ ID NO 26
```

```
<211> LENGTH: 24
<212> TYPE: PRT
<213> ORGANISM: Homo sapiens
<220> FEATURE:
<223> OTHER INFORMATION: DAP10 ITAM-containing activating domain

<400> SEQUENCE: 26

Leu Cys Ala Arg Pro Arg Arg Ser Pro Ala Gln Glu Asp Gly Lys Val
1               5                   10                  15

Tyr Ile Asn Met Pro Gly Arg Gly
            20

<210> SEQ ID NO 27
<211> LENGTH: 76
<212> TYPE: PRT
<213> ORGANISM: Homo sapiens
<220> FEATURE:
<223> OTHER INFORMATION: CD66d ITAM-containing activating domain

<400> SEQUENCE: 27

Ala Lys Thr Gly Arg Thr Ser Ile Gln Arg Asp Leu Lys Glu Gln Gln
1               5                   10                  15

Pro Gln Ala Leu Ala Pro Gly Arg Gly Pro Ser His Ser Ser Ala Phe
            20                  25                  30

Ser Met Ser Pro Leu Ser Thr Ala Gln Ala Pro Leu Pro Asn Pro Arg
        35                  40                  45

Thr Ala Ala Ser Ile Tyr Glu Glu Leu Leu Lys His Asp Thr Asn Ile
    50                  55                  60

Tyr Cys Arg Met Asp His Lys Ala Glu Val Ala Ser
65                  70                  75

<210> SEQ ID NO 28
<211> LENGTH: 21
<212> TYPE: PRT
<213> ORGANISM: Homo sapiens
<220> FEATURE:
<223> OTHER INFORMATION: Tim4 transmembrane domain

<400> SEQUENCE: 28

Leu Leu Met Ile Ile Ala Pro Ser Leu Gly Phe Val Leu Phe Ala Leu
1               5                   10                  15

Phe Val Ala Phe Leu
            20

<210> SEQ ID NO 29
<211> LENGTH: 27
<212> TYPE: PRT
<213> ORGANISM: Homo sapiens
<220> FEATURE:
<223> OTHER INFORMATION: CD28 transmembrane domain

<400> SEQUENCE: 29

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 30
<211> LENGTH: 27
<212> TYPE: PRT
<213> ORGANISM: Homo sapiens
<220> FEATURE:
<223> OTHER INFORMATION: 4-1BB transmembrane domain
```

```
<400> SEQUENCE: 30

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25

<210> SEQ ID NO 31
<211> LENGTH: 21
<212> TYPE: PRT
<213> ORGANISM: Homo sapiens
<220> FEATURE:
<223> OTHER INFORMATION: OX40 transmembrane domain from UniProt Ref.
      P43489

<400> SEQUENCE: 31

Val Ala Ala Ile Leu Gly Leu Gly Leu Val Leu Gly Leu Leu Gly Pro
1               5                   10                  15

Leu Ala Ile Leu Leu
            20

<210> SEQ ID NO 32
<211> LENGTH: 21
<212> TYPE: PRT
<213> ORGANISM: Homo sapiens
<220> FEATURE:
<223> OTHER INFORMATION: CD27 transmembrane domain from UniProt Ref.
      P26842

<400> SEQUENCE: 32

Ile Leu Val Ile Phe Ser Gly Met Phe Leu Val Phe Thr Leu Ala Gly
1               5                   10                  15

Ala Leu Phe Leu His
            20

<210> SEQ ID NO 33
<211> LENGTH: 21
<212> TYPE: PRT
<213> ORGANISM: Homo sapiens
<220> FEATURE:
<223> OTHER INFORMATION: ICOS transmembrane domain from UniProt Ref.
      Q9Y6W8

<400> SEQUENCE: 33

Phe Trp Leu Pro Ile Gly Cys Ala Ala Phe Val Val Val Cys Ile Leu
1               5                   10                  15

Gly Cys Ile Leu Ile
            20

<210> SEQ ID NO 34
<211> LENGTH: 26
<212> TYPE: PRT
<213> ORGANISM: Homo sapiens
<220> FEATURE:
<223> OTHER INFORMATION: CD2 transmembrane domain from UniProt Ref.
      P06729

<400> SEQUENCE: 34

Ile Tyr Leu Ile Ile Gly Ile Cys Gly Gly Gly Ser Leu Leu Met Val
1               5                   10                  15

Phe Val Ala Leu Leu Val Phe Tyr Ile Thr
            20                  25

<210> SEQ ID NO 35
<211> LENGTH: 23
```

```
<212> TYPE: PRT
<213> ORGANISM: Homo sapiens
<220> FEATURE:
<223> OTHER INFORMATION: LFA-1 transmembrane domain from UniProt Ref.
      P05107

<400> SEQUENCE: 35

Ile Ala Ala Ile Val Gly Gly Thr Val Ala Gly Ile Val Leu Ile Gly
1               5                   10                  15

Ile Leu Leu Leu Val Ile Trp
            20

<210> SEQ ID NO 36
<211> LENGTH: 28
<212> TYPE: PRT
<213> ORGANISM: Homo sapiens
<220> FEATURE:
<223> OTHER INFORMATION: CD30 transmembrane domain from UniProt Ref.
      P28908

<400> SEQUENCE: 36

Pro Val Leu Asp Ala Gly Pro Val Leu Phe Trp Val Ile Leu Val Leu
1               5                   10                  15

Val Val Val Val Gly Ser Ser Ala Phe Leu Leu Cys
            20                  25

<210> SEQ ID NO 37
<211> LENGTH: 22
<212> TYPE: PRT
<213> ORGANISM: Homo sapiens
<220> FEATURE:
<223> OTHER INFORMATION: CD40 transmembrane domain from UniProt Ref.
      P25942

<400> SEQUENCE: 37

Ala Leu Val Val Ile Pro Ile Ile Phe Gly Ile Leu Phe Ala Ile Leu
1               5                   10                  15

Leu Val Leu Val Phe Ile
            20

<210> SEQ ID NO 38
<211> LENGTH: 21
<212> TYPE: PRT
<213> ORGANISM: Homo sapiens
<220> FEATURE:
<223> OTHER INFORMATION: PD-1 transmembrane domain from UniProt Ref.
      Q15116

<400> SEQUENCE: 38

Val Gly Val Val Gly Gly Leu Leu Gly Ser Leu Val Leu Leu Val Trp
1               5                   10                  15

Val Leu Ala Val Ile
            20

<210> SEQ ID NO 39
<211> LENGTH: 21
<212> TYPE: PRT
<213> ORGANISM: Homo sapiens
<220> FEATURE:
<223> OTHER INFORMATION: CD7 transmembrane domain from UniProt Ref.
      P09564

<400> SEQUENCE: 39

Ala Ala Leu Ala Val Ile Ser Phe Leu Leu Gly Leu Gly Leu Gly Val
1               5                   10                  15
```

Ala Cys Val Leu Ala
            20

<210> SEQ ID NO 40
<211> LENGTH: 21
<212> TYPE: PRT
<213> ORGANISM: Homo sapiens
<220> FEATURE:
<223> OTHER INFORMATION: LIGHT transmembrane domain from UniProt Ref.
      O43557

<400> SEQUENCE: 40

Val Gly Leu Gly Leu Leu Leu Leu Met Gly Ala Gly Leu Ala Val
1               5                   10                  15

Gln Gly Trp Phe Leu
            20

<210> SEQ ID NO 41
<211> LENGTH: 23
<212> TYPE: PRT
<213> ORGANISM: Homo sapiens
<220> FEATURE:
<223> OTHER INFORMATION: NKG2C transmembrane domain from UniProt Ref.
      P26717

<400> SEQUENCE: 41

Leu Thr Ala Glu Val Leu Gly Ile Ile Cys Ile Val Leu Met Ala Thr
1               5                   10                  15

Val Leu Lys Thr Ile Val Leu
            20

<210> SEQ ID NO 42
<211> LENGTH: 21
<212> TYPE: PRT
<213> ORGANISM: Homo sapiens
<220> FEATURE:
<223> OTHER INFORMATION: B7-H3 transmembrane domain from UniProt Ref.
      Q5ZPR3

<400> SEQUENCE: 42

Leu Trp Val Thr Val Gly Leu Ser Val Cys Leu Ile Ala Leu Leu Val
1               5                   10                  15

Ala Leu Ala Phe Val
            20

<210> SEQ ID NO 43
<211> LENGTH: 347
<212> TYPE: PRT
<213> ORGANISM: Artificial Sequence
<220> FEATURE:
<223> OTHER INFORMATION: Tim4 binding domain-CD28 transmembrane-CD28
      costimulatory signaling domain, amino acids 1-22
      are signal peptide

<400> SEQUENCE: 43

Met Ser Lys Gly Leu Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
        50                  55                  60

Asn Ala Glu Leu Leu Arg Thr Asp Gly Thr Arg Ile Ile Ser Arg Lys

```
                65                  70                  75                  80
        Ser Thr Lys Tyr Thr Leu Leu Gly Lys Val Gln Phe Gly Glu Val Ser
                        85                  90                  95

Leu Thr Ile Ser Asn Thr Asn Arg Gly Asp Ser Gly Val Tyr Cys Cys
                        100                 105                 110

Arg Ile Glu Val Pro Gly Trp Phe Asn Asp Val Lys Lys Asn Val Arg
                        115                 120                 125

Leu Glu Leu Arg Arg Ala Thr Thr Lys Lys Pro Thr Thr Thr Thr Thr
                        130                 135                 140

Arg Pro Thr Thr Thr Pro Tyr Val Thr Thr Thr Pro Glu Leu Leu
        145                 150                 155                 160

Pro Thr Thr Val Met Thr Thr Ser Val Leu Pro Thr Thr Pro Pro
                        165                 170                 175

Gln Thr Leu Ala Thr Thr Ala Phe Ser Thr Ala Val Thr Cys Pro
                        180                 185                 190

Ser Thr Thr Pro Gly Ser Phe Ser Gln Glu Thr Thr Lys Gly Ser Ala
                        195                 200                 205

Phe Thr Thr Glu Ser Glu Thr Leu Pro Ala Ser Asn His Ser Gln Arg
                        210                 215                 220

Ser Met Met Thr Ile Ser Thr Asp Ile Ala Val Leu Arg Pro Thr Gly
        225                 230                 235                 240

Ser Asn Pro Gly Ile Leu Pro Ser Thr Ser Gln Leu Thr Thr Gln Lys
                        245                 250                 255

Thr Thr Leu Thr Thr Ser Glu Ser Leu Gln Lys Thr Thr Lys Ser His
                        260                 265                 270

Gln Ile Asn Ser Arg Gln Thr Phe Trp Val Leu Val Val Val Gly Gly
                        275                 280                 285

Val Leu Ala Cys Tyr Ser Leu Leu Val Thr Val Ala Phe Ile Ile Phe
                        290                 295                 300

Trp Val Arg Ser Lys Arg Ser Arg Gly Gly His Ser Asp Tyr Met Asn
        305                 310                 315                 320

Met Thr Pro Arg Arg Pro Gly Pro Thr Arg Lys His Tyr Gln Pro Tyr
                        325                 330                 335

Ala Pro Pro Arg Asp Phe Ala Ala Tyr Arg Ser
                        340                 345

<210> SEQ ID NO 44
<211> LENGTH: 341
<212> TYPE: PRT
<213> ORGANISM: Artificial Sequence
<220> FEATURE:
<223> OTHER INFORMATION: Tim4 binding domain-Tim4 transmembrane-CD28
      costimulatory signaling domain, amino acids 1-22
      are signal peptide

<400> SEQUENCE: 44

Met Ser Lys Gly Leu Leu Leu Leu Trp Leu Val Thr Glu Leu Trp Trp
        1               5                   10                  15

Leu Tyr Leu Thr Pro Ala Ala Ser Glu Asp Thr Ile Ile Gly Phe Leu
                        20                  25                  30

Gly Gln Pro Val Thr Leu Pro Cys His Tyr Leu Ser Trp Ser Gln Ser
                        35                  40                  45

Arg Asn Ser Met Cys Trp Gly Lys Gly Ser Cys Pro Asn Ser Lys Cys
                        50                  55                  60

Asn Ala Glu Leu Leu Arg Thr Asp Gly Thr Arg Ile Ile Ser Arg Lys
        65                  70                  75                  80
```

Ser Thr Lys Tyr Thr Leu Leu Gly Lys Val Gln Phe Gly Glu Val Ser
            85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
            115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
            165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
            210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
            245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ile Ala Cys Cys Val Gly
            275                 280                 285

Phe Val Leu Met Val Leu Leu Phe Leu Ala Phe Leu Arg Ser Lys Arg
            290                 295                 300

Ser Arg Gly Gly His Ser Asp Tyr Met Asn Met Thr Pro Arg Arg Pro
305                 310                 315                 320

Gly Pro Thr Arg Lys His Tyr Gln Pro Tyr Ala Pro Pro Arg Asp Phe
            325                 330                 335

Ala Ala Tyr Arg Ser
            340

<210> SEQ ID NO 45
<211> LENGTH: 454
<212> TYPE: PRT
<213> ORGANISM: Artificial Sequence
<220> FEATURE:
<223> OTHER INFORMATION: Tim4 binding domain-Tim4 transmembrane-4-1BB
      costimulatory signaling domain-CD3zeta ITAM
      containing activating domain, amino acids 1-22 are
      signal peptide

<400> SEQUENCE: 45

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
            50                  55                  60

Asn Ala Glu Leu Leu Arg Thr Asp Gly Thr Arg Ile Ile Ser Arg Lys
65                  70                  75                  80

```
Ser Thr Lys Tyr Thr Leu Leu Gly Lys Val Gln Phe Gly Glu Val Ser
             85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
            210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
            275                 280                 285

Phe Val Leu Met Val Leu Leu Phe Leu Ala Phe Leu Lys Arg Gly Arg
            290                 295                 300

Lys Lys Leu Leu Tyr Ile Phe Lys Gln Pro Phe Met Arg Pro Val Gln
305                 310                 315                 320

Thr Thr Gln Glu Glu Asp Gly Cys Ser Cys Arg Phe Pro Glu Glu Glu
                325                 330                 335

Glu Gly Gly Cys Glu Leu Arg Val Lys Phe Ser Arg Ser Ala Asp Ala
            340                 345                 350

Pro Ala Tyr Gln Gln Gly Gln Asn Gln Leu Tyr Asn Glu Leu Asn Leu
            355                 360                 365

Gly Arg Arg Glu Glu Tyr Asp Val Leu Asp Lys Arg Arg Gly Arg Asp
            370                 375                 380

Pro Glu Met Gly Gly Lys Pro Arg Arg Lys Asn Pro Gln Glu Gly Leu
385                 390                 395                 400

Tyr Asn Glu Leu Gln Lys Asp Lys Met Ala Glu Ala Tyr Ser Glu Ile
                405                 410                 415

Gly Met Lys Gly Glu Arg Arg Arg Gly Lys Gly His Asp Gly Leu Tyr
            420                 425                 430

Gln Gly Leu Ser Thr Ala Thr Lys Asp Thr Tyr Asp Ala Leu His Met
            435                 440                 445

Gln Ala Leu Pro Pro Arg
    450

<210> SEQ ID NO 46
<211> LENGTH: 22
<212> TYPE: PRT
<213> ORGANISM: Homo sapiens
<220> FEATURE:
```

<223> OTHER INFORMATION: GM-CSF signal peptide sequence

<400> SEQUENCE: 46

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 47
<211> LENGTH: 24
<212> TYPE: PRT
<213> ORGANISM: Homo sapiens
<220> FEATURE:
<223> OTHER INFORMATION: Tim4 signal peptide sequence

<400> SEQUENCE: 47

Met Ser Lys Glu Pro Leu Ile Leu Trp Leu Met Ile Glu Phe Trp Trp
1               5                   10                  15

Leu Tyr Leu Thr Pro Val Thr Ser
            20

<210> SEQ ID NO 48
<211> LENGTH: 18
<212> TYPE: PRT
<213> ORGANISM: Artificial Sequence
<220> FEATURE:
<223> OTHER INFORMATION: T2A self-cleaving peptide

<400> SEQUENCE: 48

Glu Gly Arg Gly Ser Leu Leu Thr Cys Gly Asp Val Glu Glu Asn Pro
1               5                   10                  15

Gly Pro

<210> SEQ ID NO 49
<211> LENGTH: 19
<212> TYPE: PRT
<213> ORGANISM: Artificial Sequence
<220> FEATURE:
<223> OTHER INFORMATION: P2A self-cleaving peptide

<400> SEQUENCE: 49

Ala Thr Asn Phe Ser Leu Leu Lys Gln Ala Gly Asp Val Glu Glu Asn
1               5                   10                  15

Pro Gly Pro

<210> SEQ ID NO 50
<211> LENGTH: 20
<212> TYPE: PRT
<213> ORGANISM: Artificial Sequence
<220> FEATURE:
<223> OTHER INFORMATION: E2A self-cleaving peptide

<400> SEQUENCE: 50

Gln Cys Thr Asn Tyr Ala Leu Leu Lys Leu Ala Gly Asp Val Glu Ser
1               5                   10                  15

Asn Pro Gly Pro
            20

<210> SEQ ID NO 51
<211> LENGTH: 22
<212> TYPE: PRT
<213> ORGANISM: Artificial Sequence
<220> FEATURE:
<223> OTHER INFORMATION: F2A self-cleaving peptide

<400> SEQUENCE: 51

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 52
<211> LENGTH: 285
<212> TYPE: PRT
<213> ORGANISM: Homo sapiens
<220> FEATURE:
<223> OTHER INFORMATION: truncated EGFR

<400> SEQUENCE: 52

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His
        275                 280                 285

<210> SEQ ID NO 53
<211> LENGTH: 192
<212> TYPE: PRT
<213> ORGANISM: Homo sapiens
<220> FEATURE:

<223> OTHER INFORMATION: Rac1

<400> SEQUENCE: 53

```
Met Gln Ala Ile Lys Cys Val Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30

Ile Pro Thr Val Phe Asp Asn Tyr Ser Ala Asn Val Met Val Asp Gly
        35                  40                  45

Lys Pro Val Asn Leu Gly Leu Trp Asp Thr Ala Gly Gln Glu Asp Tyr
    50                  55                  60

Asp Arg Leu Arg Pro Leu Ser Tyr Pro Gln Thr Asp Val Phe Leu Ile
65                  70                  75                  80

Cys Phe Ser Leu Val Ser Pro Ala Ser Phe Glu Asn Val Arg Ala Lys
                85                  90                  95

Trp Tyr Pro Glu Val Arg His His Cys Pro Asn Thr Pro Ile Ile Leu
            100                 105                 110

Val Gly Thr Lys Leu Asp Leu Arg Asp Asp Lys Asp Thr Ile Glu Lys
        115                 120                 125

Leu Lys Glu Lys Leu Thr Pro Ile Thr Tyr Pro Gln Gly Leu Ala
    130                 135                 140

Met Ala Lys Glu Ile Gly Ala Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Pro Pro Val Lys Lys Arg Lys Arg Lys Cys Leu Leu Leu
            180                 185                 190
```

<210> SEQ ID NO 54
<211> LENGTH: 215
<212> TYPE: PRT
<213> ORGANISM: Homo sapiens
<220> FEATURE:
<223> OTHER INFORMATION: Rab5

<400> SEQUENCE: 54

```
Met Ala Ser Arg Gly Ala Thr Arg Pro Asn Gly Pro Asn Thr Gly Asn
1               5                   10                  15

Lys Ile Cys Gln Phe Lys Leu Val Leu Leu Gly Glu Ser Ala Val Gly
            20                  25                  30

Lys Ser Ser Leu Val Leu Arg Phe Val Lys Gly Gln Phe His Glu Phe
        35                  40                  45

Gln Glu Ser Thr Ile Gly Ala Ala Phe Leu Thr Gln Thr Val Cys Leu
    50                  55                  60

Asp Asp Thr Thr Val Lys Phe Glu Ile Trp Asp Thr Ala Gly Gln Glu
65                  70                  75                  80

Arg Tyr His Ser Leu Ala Pro Met Tyr Tyr Arg Gly Ala Gln Ala Ala
                85                  90                  95

Ile Val Val Tyr Asp Ile Thr Asn Glu Glu Ser Phe Ala Arg Ala Lys
            100                 105                 110

Asn Trp Val Lys Glu Leu Gln Arg Gln Ala Ser Pro Asn Ile Val Ile
        115                 120                 125

Ala Leu Ser Gly Asn Lys Ala Asp Leu Ala Asn Lys Arg Ala Val Asp
    130                 135                 140

Phe Gln Glu Ala Gln Ser Tyr Ala Asp Asp Asn Ser Leu Leu Phe Met
145                 150                 155                 160
```

Glu Thr Ser Ala Lys Thr Ser Met Asn Val Asn Gly Ile Phe Met Ala
                165                 170                 175

Ile Ala Lys Lys Leu Pro Lys Asn Glu Pro Gln Asn Pro Gly Ala Asn
            180                 185                 190

Ser Ala Arg Gly Arg Gly Val Asp Leu Thr Glu Pro Thr Gln Pro Thr
            195                 200                 205

Arg Asn Gln Cys Cys Ser Asn
            210             215

<210> SEQ ID NO 55
<211> LENGTH: 207
<212> TYPE: PRT
<213> ORGANISM: Homo sapiens
<220> FEATURE:
<223> OTHER INFORMATION: Rab7

<400> SEQUENCE: 55

Met Thr Ser Arg Lys Lys Val Leu Leu Lys Val Ile Ile Leu Gly Asp
1               5                   10                  15

Ser Gly Val Gly Lys Thr Ser Leu Met Asn Gln Tyr Val Asn Lys Lys
            20                  25                  30

Phe Ser Asn Gln Tyr Lys Ala Thr Ile Gly Ala Asp Phe Leu Thr Lys
        35                  40                  45

Glu Val Met Val Asp Asp Arg Leu Val Thr Met Gln Ile Trp Asp Thr
    50                  55                  60

Ala Gly Gln Glu Arg Phe Gln Ser Leu Gly Val Ala Phe Tyr Arg Gly
65                  70                  75                  80

Ala Asp Cys Cys Val Leu Val Phe Asp Val Thr Ala Pro Asn Thr Phe
                85                  90                  95

Lys Thr Leu Asp Ser Trp Arg Asp Glu Phe Leu Ile Gln Ala Ser Pro
            100                 105                 110

Arg Asp Pro Glu Asn Phe Pro Phe Val Val Leu Gly Asn Lys Ile Asp
        115                 120                 125

Leu Glu Asn Arg Gln Val Ala Thr Lys Arg Ala Gln Ala Trp Cys Tyr
    130                 135                 140

Ser Lys Asn Asn Ile Pro Tyr Phe Glu Thr Ser Ala Lys Glu Ala Ile
145                 150                 155                 160

Asn Val Glu Gln Ala Phe Gln Thr Ile Ala Arg Asn Ala Leu Lys Gln
                165                 170                 175

Glu Thr Glu Val Glu Leu Tyr Asn Glu Phe Pro Glu Pro Ile Lys Leu
            180                 185                 190

Asp Lys Asn Asp Arg Ala Lys Ala Ser Ala Glu Ser Cys Ser Cys
        195                 200                 205

<210> SEQ ID NO 56
<211> LENGTH: 184
<212> TYPE: PRT
<213> ORGANISM: Homo sapiens
<220> FEATURE:
<223> OTHER INFORMATION: Rap1

<400> SEQUENCE: 56

Met Arg Glu Tyr Lys Leu Val Val Leu Gly Ser Gly Gly Val Gly Lys
1               5                   10                  15

Ser Ala Leu Thr Val Gln Phe Val Gln Gly Ile Phe Val Glu Lys Tyr
            20                  25                  30

Asp Pro Thr Ile Glu Asp Ser Tyr Arg Lys Gln Val Glu Val Asp Cys

```
                   35                  40                  45
Gln Gln Cys Met Leu Glu Ile Leu Asp Thr Ala Gly Thr Glu Gln Phe
 50                  55                  60

Thr Ala Met Arg Asp Leu Tyr Met Lys Asn Gly Gln Gly Phe Ala Leu
65                  70                  75                  80

Val Tyr Ser Ile Thr Ala Gln Ser Thr Phe Asn Asp Leu Gln Asp Leu
                 85                  90                  95

Arg Glu Gln Ile Leu Arg Val Lys Asp Thr Glu Asp Val Pro Met Ile
            100                 105                 110

Leu Val Gly Asn Lys Cys Asp Leu Glu Asp Glu Arg Val Val Gly Lys
        115                 120                 125

Glu Gln Gly Gln Asn Leu Ala Arg Gln Trp Cys Asn Cys Ala Phe Leu
    130                 135                 140

Glu Ser Ser Ala Lys Ser Lys Ile Asn Val Asn Glu Ile Phe Tyr Asp
145                 150                 155                 160

Leu Val Arg Gln Ile Asn Arg Lys Thr Pro Val Glu Lys Lys Lys Pro
                165                 170                 175

Lys Lys Lys Ser Cys Leu Leu Leu
            180

<210> SEQ ID NO 57
<211> LENGTH: 193
<212> TYPE: PRT
<213> ORGANISM: Homo sapiens
<220> FEATURE:
<223> OTHER INFORMATION: RhoA

<400> SEQUENCE: 57

Met Ala Ala Ile Arg Lys Lys Leu Val Ile Val Gly Asp Gly Ala Cys
1               5                   10                  15

Gly Lys Thr Cys Leu Leu Ile Val Phe Ser Lys Asp Gln Phe Pro Glu
                20                  25                  30

Val Tyr Val Pro Thr Val Phe Glu Asn Tyr Val Ala Asp Ile Glu Val
            35                  40                  45

Asp Gly Lys Gln Val Glu Leu Ala Leu Trp Asp Thr Ala Gly Gln Glu
 50                 55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95

Glu Lys Trp Thr Pro Glu Val Lys His Phe Cys Pro Asn Val Pro Ile
            100                 105                 110

Ile Leu Val Gly Asn Lys Lys Asp Leu Arg Asn Asp Glu His Thr Arg
        115                 120                 125

Arg Glu Leu Ala Lys Met Lys Gln Glu Pro Val Lys Pro Glu Glu Gly
    130                 135                 140

Arg Asp Met Ala Asn Arg Ile Gly Ala Phe Gly Tyr Met Glu Cys Ser
145                 150                 155                 160

Ala Lys Thr Lys Asp Gly Val Arg Glu Val Phe Glu Met Ala Thr Arg
                165                 170                 175

Ala Ala Leu Gln Ala Arg Arg Gly Lys Lys Lys Ser Gly Cys Leu Val
            180                 185                 190

Leu

<210> SEQ ID NO 58
```

```
<211> LENGTH: 191
<212> TYPE: PRT
<213> ORGANISM: Homo sapiens
<220> FEATURE:
<223> OTHER INFORMATION: CDC42

<400> SEQUENCE: 58

Met Gln Thr Ile Lys Cys Val Val Val Gly Asp Gly Ala Val Gly Lys
1               5                   10                  15

Thr Cys Leu Leu Ile Ser Tyr Thr Thr Asn Lys Phe Pro Ser Glu Tyr
            20                  25                  30

Val Pro Thr Val Phe Asp Asn Tyr Ala Val Thr Val Met Ile Gly Gly
        35                  40                  45

Glu Pro Tyr Thr Leu Gly Leu Phe Asp Thr Ala Gly Gln Glu Asp Tyr
    50                  55                  60

Asp Arg Leu Arg Pro Leu Ser Tyr Pro Gln Thr Asp Val Phe Leu Val
65                  70                  75                  80

Cys Phe Ser Val Val Ser Pro Ser Ser Phe Glu Asn Val Lys Glu Lys
                85                  90                  95

Trp Val Pro Glu Ile Thr His His Cys Pro Lys Thr Pro Phe Leu Leu
            100                 105                 110

Val Gly Thr Gln Ile Asp Leu Arg Asp Asp Pro Ser Thr Ile Glu Lys
        115                 120                 125

Leu Ala Lys Asn Lys Gln Lys Pro Ile Thr Pro Glu Thr Ala Glu Lys
    130                 135                 140

Leu Ala Arg Asp Leu Lys Ala Val Lys Tyr Val Glu Cys Ser Ala Leu
145                 150                 155                 160

Thr Gln Lys Gly Leu Lys Asn Val Phe Asp Glu Ala Ile Leu Ala Ala
                165                 170                 175

Leu Glu Pro Pro Glu Pro Lys Lys Ser Arg Arg Cys Val Leu Leu
            180                 185                 190

<210> SEQ ID NO 59
<211> LENGTH: 21
<212> TYPE: PRT
<213> ORGANISM: Mus musculus
<220> FEATURE:
<223> OTHER INFORMATION: Tim4 transmembrane domain

<400> SEQUENCE: 59

Ile Leu Ile Ile Ala Cys Cys Val Gly Phe Val Leu Met Val Leu Leu
1               5                   10                  15

Phe Leu Ala Phe Leu
            20

<210> SEQ ID NO 60
<211> LENGTH: 279
<212> TYPE: PRT
<213> ORGANISM: Mus musculus
<220> FEATURE:
<223> OTHER INFORMATION: Tim4 binding domain, amino acids 1-22 are
      signal peptide

<400> SEQUENCE: 60

Met Ser Lys Gly Leu Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45
```

Arg Asn Ser Met Cys Trp Gly Lys Gly Ser Cys Pro Asn Ser Lys Cys
            50                  55                  60

Asn Ala Glu Leu Leu Arg Thr Asp Gly Thr Arg Ile Ile Ser Arg Lys
 65                  70                  75                  80

Ser Thr Lys Tyr Thr Leu Leu Gly Lys Val Gln Phe Gly Glu Val Ser
                 85                  90                  95

Leu Thr Ile Ser Asn Thr Asn Arg Gly Asp Ser Gly Val Tyr Cys Cys
                100                 105                 110

Arg Ile Glu Val Pro Gly Trp Phe Asn Asp Val Lys Lys Asn Val Arg
                115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
                180                 185                 190

Ser Thr Thr Pro Gly Ser Phe Ser Gln Glu Thr Thr Lys Gly Ser Ala
                195                 200                 205

Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
                260                 265                 270

Gln Ile Asn Ser Arg Gln Thr
                275

<210> SEQ ID NO 61
<211> LENGTH: 22
<212> TYPE: PRT
<213> ORGANISM: Mus musculus
<220> FEATURE:
<223> OTHER INFORMATION: Tim4 signal peptide

<400> SEQUENCE: 61

Met Ser Lys Gly Leu Leu Leu Trp Leu Val Thr Glu Leu Trp Trp
1               5                   10                  15

Leu Tyr Leu Thr Pro Ala
            20

<210> SEQ ID NO 62
<211> LENGTH: 41
<212> TYPE: PRT
<213> ORGANISM: Artificial Sequence
<220> FEATURE:
<223> OTHER INFORMATION: human CD28 costimulatory signaling domain with
      L186G/L187G substitutions (positions reference to
      full length protein)

<400> SEQUENCE: 62

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

```
Pro Arg Asp Phe Ala Ala Tyr Arg Ser
        35                  40

<210> SEQ ID NO 63
<211> LENGTH: 113
<212> TYPE: PRT
<213> ORGANISM: Homo sapiens
<220> FEATURE:
<223> OTHER INFORMATION: wildtype CD3zeta activating domain

<400> SEQUENCE: 63

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 64
<211> LENGTH: 23
<212> TYPE: PRT
<213> ORGANISM: Artificial Sequence
<220> FEATURE:
<223> OTHER INFORMATION: T2A self-cleaving peptide variant

<400> SEQUENCE: 64

Leu Glu Gly Gly Gly Glu Gly Arg Gly Ser Leu Leu Thr Cys Gly Asp
1               5                   10                  15

Val Glu Glu Asn Pro Gly Pro
            20

<210> SEQ ID NO 65
<211> LENGTH: 19
<212> TYPE: PRT
<213> ORGANISM: Artificial Sequence
<220> FEATURE:
<223> OTHER INFORMATION: T2A self-cleaving peptide variant

<400> SEQUENCE: 65

Glu Gly Arg Gly Ser Leu Leu Thr Cys Gly Asp Val Glu Glu Asn Pro
1               5                   10                  15

Gly Pro Arg

<210> SEQ ID NO 66
<211> LENGTH: 24
<212> TYPE: PRT
<213> ORGANISM: Artificial Sequence
<220> FEATURE:
<223> OTHER INFORMATION: T2A self-cleaving peptide variant

<400> SEQUENCE: 66

Leu Glu Gly Gly Gly Glu Gly Arg Gly Ser Leu Leu Thr Cys Gly Asp
```

```
1               5                   10                  15
Val Glu Glu Asn Pro Gly Pro Arg
            20
```

<210> SEQ ID NO 67
<211> LENGTH: 27
<212> TYPE: PRT
<213> ORGANISM: Artificial Sequence
<220> FEATURE:
<223> OTHER INFORMATION: P2A self-cleaving peptide variant

<400> SEQUENCE: 67

```
Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro
            20                  25
```

<210> SEQ ID NO 68
<211> LENGTH: 382
<212> TYPE: PRT
<213> ORGANISM: Artificial Sequence
<220> FEATURE:
<223> OTHER INFORMATION: Tim4 binding domain-CD28 TM-CD28 costim
      (SEQ ID NO:2 + 29 + 4)

<400> SEQUENCE: 68

```
Met Ser Lys Glu Pro Leu Ile Leu Trp Leu Met Ile Glu Phe Trp Trp
1               5                   10                  15

Leu Tyr Leu Thr Pro Val Thr Ser Glu Thr Val Val Thr Glu Val Leu
            20                  25                  30

Gly His Arg Val Thr Leu Pro Cys Leu Tyr Ser Ser Trp Ser His Asn
        35                  40                  45

Ser Asn Ser Met Cys Trp Gly Lys Asp Gln Cys Pro Tyr Ser Gly Cys
    50                  55                  60

Lys Glu Ala Leu Ile Arg Thr Asp Gly Met Arg Val Thr Ser Arg Lys
65                  70                  75                  80

Ser Ala Lys Tyr Arg Leu Gln Gly Thr Ile Pro Arg Gly Asp Val Ser
                85                  90                  95

Leu Thr Ile Leu Asn Pro Ser Glu Ser Asp Ser Gly Val Tyr Cys Cys
            100                 105                 110

Arg Ile Glu Val Pro Gly Trp Phe Asn Asp Val Lys Ile Asn Val Arg
        115                 120                 125

Leu Asn Leu Gln Arg Ala Ser Thr Thr Thr His Arg Thr Ala Thr Thr
    130                 135                 140

Thr Thr Arg Arg Thr Thr Thr Ser Pro Thr Thr Thr Arg Gln Met Thr
145                 150                 155                 160

Thr Thr Thr Pro Ala Ala Leu Pro Thr Thr Val Val Thr Thr Pro Asp
                165                 170                 175

Leu Thr Thr Gly Thr Pro Leu Gln Met Thr Thr Ile Ala Val Phe Thr
            180                 185                 190

Thr Ala Asn Thr Cys Leu Ser Leu Thr Pro Ser Thr Leu Pro Glu Glu
        195                 200                 205

Ala Thr Gly Leu Leu Thr Pro Glu Pro Ser Lys Glu Gly Pro Ile Leu
    210                 215                 220

Thr Ala Glu Ser Glu Thr Val Leu Pro Ser Asp Ser Trp Ser Ser Val
225                 230                 235                 240

Glu Ser Thr Ser Ala Asp Thr Val Leu Leu Thr Ser Lys Glu Ser Lys
                245                 250                 255
```

```
Val Trp Asp Leu Pro Ser Thr Ser His Val Ser Met Trp Lys Thr Ser
            260                 265                 270

Asp Ser Val Ser Ser Pro Gln Pro Gly Ala Ser Asp Thr Ala Val Pro
                275                 280                 285

Glu Gln Asn Lys Thr Thr Lys Thr Gly Gln Met Asp Gly Ile Pro Met
290                 295                 300

Ser Met Lys Asn Glu Met Pro Ile Ser Gln Phe Trp Val Leu Val Val
305                 310                 315                 320

Val Gly Gly Val Leu Ala Cys Tyr Ser Leu Leu Val Thr Val Ala Phe
                325                 330                 335

Ile Ile Phe Trp Val Arg Ser Lys Arg Ser Arg Leu Leu His Ser Asp
                340                 345                 350

Tyr Met Asn Met Thr Pro Arg Arg Pro Gly Pro Thr Arg Lys His Tyr
                355                 360                 365

Gln Pro Tyr Ala Pro Pro Arg Asp Phe Ala Ala Tyr Arg Ser
                370                 375                 380

<210> SEQ ID NO 69
<211> LENGTH: 495
<212> TYPE: PRT
<213> ORGANISM: Artificial Sequence
<220> FEATURE:
<223> OTHER INFORMATION: Tim4 binding domain-CD28 TM-CD28 costim-CD3z
      (SEQ ID NO:2 + 29 + 4 + 63)

<400> SEQUENCE: 69

Met Ser Lys Glu Pro Leu Ile Leu Trp Leu Met Ile Glu Phe Trp Trp
1               5                   10                  15

Leu Tyr Leu Thr Pro Val Thr Ser Glu Thr Val Val Thr Glu Val Leu
                20                  25                  30

Gly His Arg Val Thr Leu Pro Cys Leu Tyr Ser Ser Trp Ser His Asn
            35                  40                  45

Ser Asn Ser Met Cys Trp Gly Lys Asp Gln Cys Pro Tyr Ser Gly Cys
    50                  55                  60

Lys Glu Ala Leu Ile Arg Thr Asp Gly Met Arg Val Thr Ser Arg Lys
65                  70                  75                  80

Ser Ala Lys Tyr Arg Leu Gln Gly Thr Ile Pro Arg Gly Asp Val Ser
                85                  90                  95

Leu Thr Ile Leu Asn Pro Ser Glu Ser Asp Ser Gly Val Tyr Cys Cys
            100                 105                 110

Arg Ile Glu Val Pro Gly Trp Phe Asn Asp Val Lys Ile Asn Val Arg
        115                 120                 125

Leu Asn Leu Gln Arg Ala Ser Thr Thr Thr His Arg Thr Ala Thr Thr
    130                 135                 140

Thr Thr Arg Arg Thr Thr Thr Thr Ser Pro Thr Thr Thr Arg Gln Met
145                 150                 155                 160

Thr Thr Thr Pro Ala Ala Leu Pro Thr Thr Val Val Thr Thr Pro Asp
                165                 170                 175

Leu Thr Thr Gly Thr Pro Leu Gln Met Thr Thr Ile Ala Val Phe Thr
            180                 185                 190

Thr Ala Asn Thr Cys Leu Ser Leu Thr Pro Ser Thr Leu Pro Glu Glu
        195                 200                 205

Ala Thr Gly Leu Leu Thr Pro Glu Pro Ser Lys Glu Gly Pro Ile Leu
    210                 215                 220

Thr Ala Glu Ser Glu Thr Val Leu Pro Ser Asp Ser Trp Ser Ser Val
```

```
                225                 230                 235                 240
            Glu Ser Thr Ser Ala Asp Thr Val Leu Leu Thr Ser Lys Glu Ser Lys
                            245                 250                 255

Val Trp Asp Leu Pro Ser Thr Ser His Val Ser Met Trp Lys Thr Ser
                            260                 265                 270

Asp Ser Val Ser Ser Pro Gln Pro Gly Ala Ser Asp Thr Ala Val Pro
                        275                 280                 285

Glu Gln Asn Lys Thr Thr Lys Thr Gly Gln Met Asp Gly Ile Pro Met
                    290                 295                 300

Ser Met Lys Asn Glu Met Pro Ile Ser Gln Phe Trp Val Leu Val Val
            305                 310                 315                 320

Val Gly Gly Val Leu Ala Cys Tyr Ser Leu Leu Val Thr Val Ala Phe
                            325                 330                 335

Ile Ile Phe Trp Val Arg Ser Lys Arg Ser Arg Leu Leu His Ser Asp
                        340                 345                 350

Tyr Met Asn Met Thr Pro Arg Arg Pro Gly Pro Thr Arg Lys His Tyr
                        355                 360                 365

Gln Pro Tyr Ala Pro Pro Arg Asp Phe Ala Ala Tyr Arg Ser Arg Val
                    370                 375                 380

Lys Phe Ser Arg Ser Ala Asp Ala Pro Ala Tyr Gln Gln Gly Gln Asn
            385                 390                 395                 400

Gln Leu Tyr Asn Glu Leu Asn Leu Gly Arg Arg Glu Glu Tyr Asp Val
                            405                 410                 415

Leu Asp Lys Arg Arg Gly Arg Asp Pro Glu Met Gly Gly Lys Pro Gln
                        420                 425                 430

Arg Arg Lys Asn Pro Gln Glu Gly Leu Tyr Asn Glu Leu Gln Lys Asp
                    435                 440                 445

Lys Met Ala Glu Ala Tyr Ser Glu Ile Gly Met Lys Gly Glu Arg Arg
                    450                 455                 460

Arg Gly Lys Gly His Asp Gly Leu Tyr Gln Gly Leu Ser Thr Ala Thr
            465                 470                 475                 480

Lys Asp Thr Tyr Asp Ala Leu His Met Gln Ala Leu Pro Pro Arg
                            485                 490                 495
```